(12) United States Patent
Konno

(10) Patent No.: US 8,993,754 B2
(45) Date of Patent: Mar. 31, 2015

(54) IRIDIUM COMPLEX AND LIGHT EMITTING MATERIAL FORMED FROM SAME

(75) Inventor: Hideo Konno, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 33 days.

(21) Appl. No.: 13/392,402

(22) PCT Filed: Aug. 23, 2010

(86) PCT No.: PCT/JP2010/064140
§ 371 (c)(1),
(2), (4) Date: May 3, 2012

(87) PCT Pub. No.: WO2011/024737
PCT Pub. Date: Mar. 3, 2011

(65) Prior Publication Data
US 2012/0208999 A1    Aug. 16, 2012

(30) Foreign Application Priority Data

Aug. 27, 2009  (JP) .................................. 2009-196405

(51) Int. Cl.
| | | |
|---|---|---|
| C07D 403/12 | (2006.01) |
| C07D 403/14 | (2006.01) |
| C07D 239/30 | (2006.01) |
| C07D 239/34 | (2006.01) |
| C07D 239/02 | (2006.01) |
| C07F 15/00 | (2006.01) |
| C09K 11/06 | (2006.01) |
| H01L 51/00 | (2006.01) |
| H05B 33/14 | (2006.01) |
| F21K 2/00 | (2006.01) |
| H01L 51/50 | (2006.01) |

(52) U.S. Cl.
CPC ............ C07F 15/0033 (2013.01); C09K 11/06 (2013.01); *C09K 2211/1029* (2013.01); *C09K 2211/185* (2013.01); H01L 51/0085 (2013.01); *H01L 51/5016* (2013.01); H05B 33/14 (2013.01)
USPC ............................ 544/242; 544/296; 544/335

(58) Field of Classification Search
USPC ......................................... 544/296, 335, 242
See application file for complete search history.

(56) References Cited

U.S. PATENT DOCUMENTS

2012/0223276 A1 * 9/2012 Parham et al. ................ 252/500

FOREIGN PATENT DOCUMENTS

| EP | 2 471 889 | 7/2012 |
|---|---|---|
| JP | 2001-247859 | 9/2001 |
| JP | 2003-81988 | 3/2003 |
| JP | 2004-503059 | 1/2004 |
| JP | 2005-516040 | 6/2005 |
| JP | 2006-8688 | 1/2006 |
| JP | 2008-74921 | 4/2008 |
| JP | 2009-40728 | 2/2009 |
| JP | 2011-68638 | 4/2011 |
| WO | WO-02/02714 | 1/2002 |
| WO | WO-2012/008493 | 1/2012 |

OTHER PUBLICATIONS

Hackh's Chemical Dictionary, 3$^{rd}$ Ed., 1944, p. 18, "acyl."*
Wikipedia, Acyl, last modified Mar. 11, 2012l.*
IUPAC, http://www.iupac.org/goldbook/A00123.pdf, downloaded Oct. 29, 2010.*
Hawley's Condensed Chem. Dict. 14$^{th}$ Ed., 2002.*
Grushin, V.V.. et al., (2001). "New, efficient electroluminescent materials based on organometallic Ir complexes," *Chem Communication* 16:1494-1495.
Ge, G., et al. (2009). "Polymer-based blue electrophosphorescent light-emitting diodes based on a new iridium (III) diazine complex," *Synthetic Metals* 159:1178-1182.
Lin, C. et al. (2009). "Synthesis and characterization of cyclometalated iridium(III) complexes containing pyrimidine-based ligands," *Journal of Organometallic Chemistry* 694:2757-2769.
Search Report mailed Oct. 26, 2010, directed to International Application No. PCT/JP2010/064140; 2 pages.
Extended Search Report dated Mar. 8, 2013, directed to EP Application No. 10811787.0; 7 pages.

* cited by examiner

*Primary Examiner* — Deepak Rao
*Assistant Examiner* — Cecilia M Jaisle
(74) *Attorney, Agent, or Firm* — Morrison & Foerster LLP

(57) ABSTRACT

Provided is an iridium complex having a substructure represented by the following formula (1), which is a luminescent element material capable of luminescence with high brightness/high efficiency and excellent in durability and can be used in a luminescent element, etc.

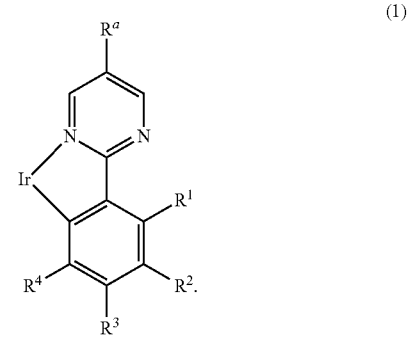

(1)

14 Claims, 3 Drawing Sheets

IRIDIUM COMPLEX AND LIGHT EMITTING MATERIAL FORMED FROM SAME

TECHNICAL FIELD

The present invention relates to an iridium complex useful as materials for organic electroluminescent elements, electrochemiluminescence (ECL) element materials, luminescent sensors, oxygen sensor, photosensitizers, displays, materials for photographs, laser dyes, dyes for color filters, optical communications, color conversion filters, backlights, illumination, photosensitizing dyes, luminescent probes for cell imaging, various light sources, etc., and a luminescent material comprising the compound.

BACKGROUND ART

Organic electroluminescent elements have received attention as next-generation display elements, and the development of various organic materials used in the luminescent elements has been promoted actively in recent years. Particularly, attention has been focused on phosphorescent materials that utilize luminescence from an excited triplet state, as luminescent materials from the viewpoint of improvement in luminous efficiency.

In the case of using luminescence from an excited singlet state, the limit of external quantum efficiency is allegedly 5% because the generation ratio between a singlet exciton and a triplet exciton is 1:3 and thus the generation probability of luminescent excited species is 25% and because light extraction efficiency is approximately 20%. On the other hand, if even an excited triplet state can be utilized in this, luminous efficiency becomes four times in principle compared with the case of the excited singlet because the upper limit of internal quantum efficiency becomes 100%; thus the development of phosphorescent materials has been performed actively. Although iridium complexes having a 2-phenylpyridine-based ligand have received attention so far as typical phosphorescent materials, the development of novel phosphorescent materials has been demanded with the future objective of further improvement in luminous efficiency and durability.

Iridium complexes having a 2-phenylpyrimidine-based ligand similar to a compound of the present invention are described in Patent Literatures 1 to 7 and Non Patent Literatures 1 to 3. However, the problems to be solved, such as luminous efficiency or durability, still remain, and more thermally stable materials exhibiting high luminous efficiency have been demanded. Moreover, according to the findings of the present inventor, there were problems about the iridium complexes having a 2-phenylpyrimidine-based ligand compared with 2-phenylpyridine-based iridium complexes: solubility in a solvent was low and workability and operability were significantly poor.

Although an iridium complex in which a trifluoromethyl group is introduced in position 5 of the pyrimidine ring (see a diagram below) of a 2-phenylpyrimidine ligand (formula (A)) is disclosed in Non Patent Literature 1, its thermal stability is low (see [0171]) and in addition, its luminescence is limited to a green color (λmax=525 nm).

[Chemical Formula 4]

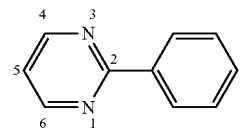

[Chemical Formula 5]

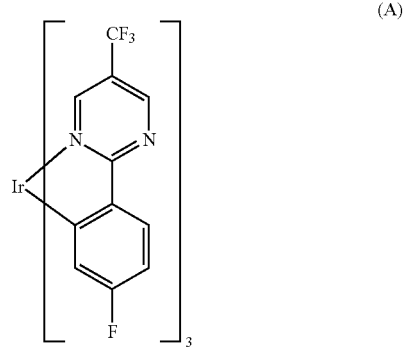

(A)

An iridium complex in which a phenyl group or a thienyl group is introduced in position 5 of the pyrimidine ring of a 2-phenylpyrimidine ligand (e.g., formula (B)) is disclosed in Non Patent Literature 2. However, the emission wavelengths of these iridium complexes are 522 to 558 nm and their colors of luminescence are limited to green to orange regions. Particularly, for the iridium complex of the skeleton described in Non Patent Literature 2, it is difficult to emit light in a blue region. Moreover, according to Non Patent Literature 2, there are problems: the emission quantum yields of these iridium complexes in toluene are 0.052 to 0.34 and are still low.

[Chemical Formula 6]

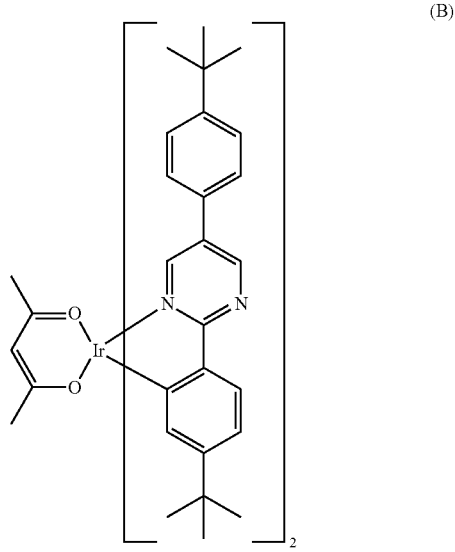

(B)

An iridium complex in which a methyl group is introduced in position 4 of the pyrimidine ring of a 2-phenylpyrimidine ligand (formula (C)) is disclosed in Patent Literature 7. However, using the ligand of this type, there is the possibility that isomers are generated depending on coordination patterns to iridium (see a diagram below), and there are problems: it is difficult to synthesize the intended iridium complex with high purity. Also, there is the possibility that contamination with various isomers have adverse effect on luminescent elements.

[Chemical Formula 7]

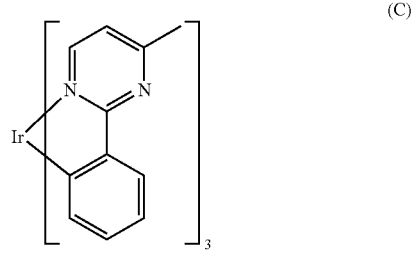

(C)

[Chemical Formula 8]

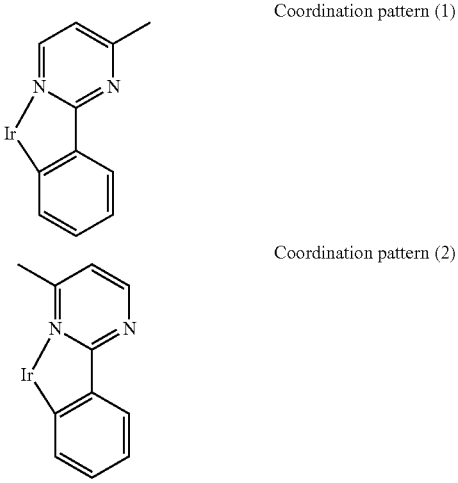

Coordination pattern (1)

Coordination pattern (2)

Moreover, phosphorescent materials exhibiting a high emission quantum yield in a solid state are preferable for solid devices such as organic electroluminescent elements, and further, phosphorescent materials highly soluble in a solvent have been desired strongly in the case of producing films of these phosphorescent materials by a coating method. As described above, the 2-phenylpyrimidine-based iridium complexes described in Patent Literatures 1 to 7 and Non Patent Literatures 1 to 3 still have room for improvement from the viewpoints described above. Although search for novel phosphorescent materials has been performed in such technical background, there is no description about the luminescence properties of an iridium complex in which an alkyl group having 2 to 30 carbon atoms which may have a substituent is introduced in position 5 of the pyrimidine ring of a 2-phenylpyrimidine ligand, and the properties of a luminescent element using it.

CITATION LIST

Patent Literature

Patent Literature 1: Japanese Patent Application Laid-Open Publication No. 2001-247859
Patent Literature 2: Japanese Patent Application Laid-Open Publication No. 2003-81988
Patent Literature 3: Japanese Patent Application Laid-Open Publication No. 2006-8688
Patent Literature 4: Japanese Patent Application Laid-Open Publication No. 2008-74921
Patent Literature 5: Japanese Unexamined Patent Application Publication No. 2004-503059
Patent Literature 6: Japanese Unexamined Patent Application Publication No. 2005-516040
Patent Literature 7: Japanese Patent Application Laid-Open Publication No. 2009-40728

Non Patent Literature

Non Patent Literature 1: Chemical Communications, 2001, p. 1494
Non Patent Literature 2: J. Organomet. Chem., 2009, vol. 694, p. 2757
Non Patent Literature 3: Synthetic Metals, 2009, vol. 159, p. 1178

SUMMARY OF INVENTION

Technical Problem

An object of the present invention is to provide a luminescent element capable of luminescence with high brightness/high efficiency and excellent in durability, and a novel iridium complex that can be used in the luminescent element and can also be applied to organic electroluminescent element materials, electrochemiluminescence (ECL) element materials, luminescent sensors, oxygen sensors, photosensitizers, displays, materials for photographs, laser dyes, dyes for color filters, optical communications, color conversion filters, backlights, illumination, photosensitizing dyes, luminescent probes for cell imaging, various light sources, etc.

Solution to Problem

As a result of repeating diligent studies in consideration of the circumstances described above, the present inventors have completed the present invention by finding that a novel iridium complex represented by formula (1) or (2) is very thermally stable compared with conventional compounds in which a substituent is not introduced in $R^a$, has excellent luminescence properties, particularly in a solid state, in the visible light region, is further highly soluble in a solvent and excellent in workability, and is useful as luminescent materials for various applications.

Specifically, according to this application, the following invention is provided:

<1> An iridium complex having a substructure represented by the following formula (1):

[Chemical Formula 1]

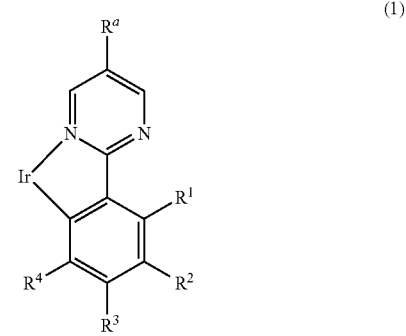

(1)

wherein N represents a nitrogen atom; $R^a$ represents an alkyl group having 2 to 30 carbon atoms which may have a substituent; $R^1$ to $R^4$ each independently represent a hydrogen atom or an alkyl group having 1 to 30 carbon atoms which may have a substituent, an aryl group having 6 to 60 carbon atoms which may have a substituent, an alkenyl group having 2 to 30 carbon atoms which may have a substituent, an alkynyl group having 2 to 30 carbon atoms which may have a substituent, an amino group having 0 to 30 carbon atoms which may have a substituent, a heterocyclic group having 1 to 60 carbon atoms which may have a substituent, an alkoxy group having 1 to 30 carbon atoms which may have a substituent, an alkylthio group having 1 to 30 carbon atoms which may have a substituent, an aryloxy group having 6 to 60 carbon atoms which may have a substituent, an arylthio group having 6 to 60 carbon atoms which may have a substituent, a heterocyclic oxy group having 1 to 60 carbon atoms which may have a substituent, a heterocyclic thio group having 1 to 60 carbon atoms which may have a substituent, an acyl group, an acyloxy group, an amide group, an acid imide group, an imine residue, a substituted silyl group, a substituted silyloxy group, a substituted silylthio group, a substituted silylamino group, a halogen atom, a cyano group, a carboxyl group, or a trifluoromethyl group; and adjacent substituents may be bonded to form a ring structure.

<2> An iridium complex represented by the following formula (2):

[Chemical Formula 2]

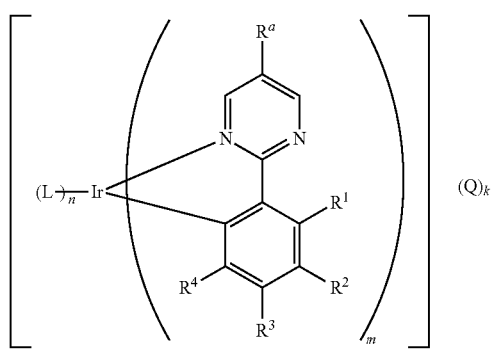

(2)

wherein N represents a nitrogen atom; m represents an integer of 1 to 3; n represents an integer of 0 to 2; m+n=3; $R^a$ represents an alkyl group having 2 to 30 carbon atoms which may have a substituent; $R^1$ to $R^4$ each independently represent a hydrogen atom or an alkyl group having 1 to 30 carbon atoms which may have a substituent, an aryl group having 6 to 60 carbon atoms which may have a substituent, an alkenyl group having 2 to 30 carbon atoms which may have a substituent, an alkynyl group having 2 to 30 carbon atoms which may have a substituent, an amino group having 0 to 30 carbon atoms which may have a substituent, a heterocyclic group having 1 to 60 carbon atoms which may have a substituent, an alkoxy group having 1 to 30 carbon atoms which may have a substituent, an alkylthio group having 1 to 30 carbon atoms which may have a substituent, an aryloxy group having 6 to 60 carbon atoms which may have a substituent, an arylthio group having 6 to 60 carbon atoms which may have a substituent, a heterocyclic oxy group having 1 to 60 carbon atoms which may have a substituent, a heterocyclic thio group having 1 to 60 carbon atoms which may have a substituent, an acyl group, an acyloxy group, an amide group, an acid imide group, an imine residue, a substituted silyl group, a substituted silyloxy group, a substituted silylthio group, a substituted silylamino group, a halogen atom, a cyano group, a carboxyl group, or a trifluoromethyl group; Q represents a counter ion; k represents an integer of 0 to 2; L represents a bidentate ligand; and adjacent substituents may be bonded to form a ring structure.

<3> The iridium complex according to <2> above, wherein L is represented by any of formulas (3) to (11):

[Chemical Formula 3]

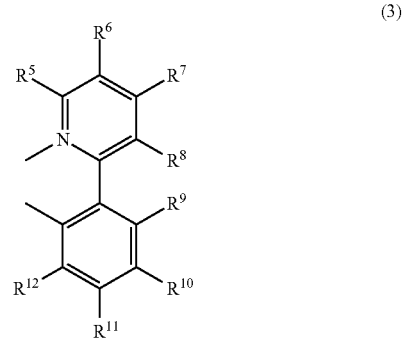

(3)

(4)

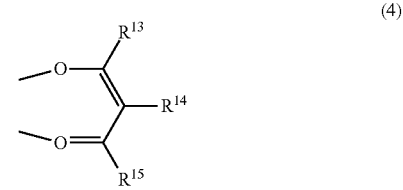

(5)

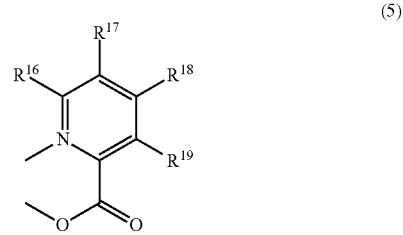

(6)

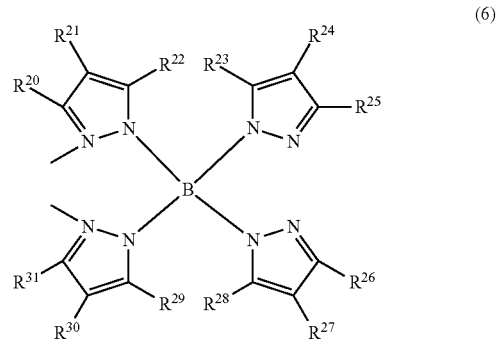

(7)

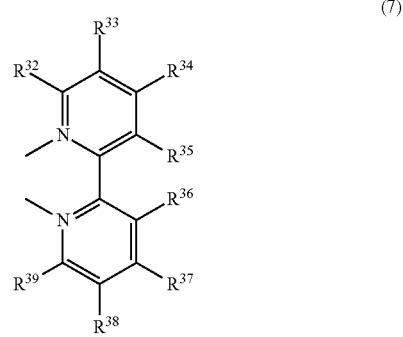

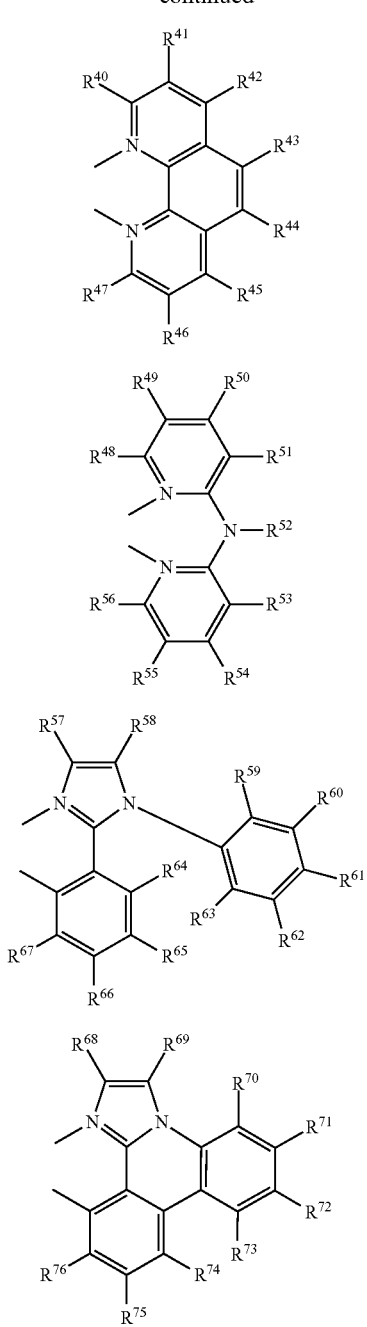

wherein $R^5$ to $R^{76}$ each independently represent a hydrogen atom or an alkyl group having 1 to 30 carbon atoms which may have a substituent, an aryl group having 6 to 60 carbon atoms which may have a substituent, an alkenyl group having 2 to 30 carbon atoms which may have a substituent, an alkynyl group having 2 to 30 carbon atoms which may have a substituent, an amino group having 0 to 30 carbon atoms which may have a substituent, a heterocyclic group having 1 to 60 carbon atoms which may have a substituent, an alkoxy group having 1 to 30 carbon atoms which may have a substituent, an alkylthio group having 1 to 30 carbon atoms which may have a substituent, an aryloxy group having 6 to 60 carbon atoms which may have a substituent, an arylthio group having 6 to 60 carbon atoms which may have a substituent, a heterocyclic oxy group having 1 to 60 carbon atoms which may have a substituent, a heterocyclic thio group having 1 to 60 carbon atoms which may have a substituent, an acyl group, an aryloxy group, an amide group, an acid imide group, an imine residue, a substituted silyl group, a substituted silyloxy group, a substituted silylthio group, a substituted silylamino group, a halogen atom, a cyano group, a carboxyl group, or a trifluoromethyl group; and adjacent substituents may be bonded to form a ring structure.

<4> The iridium complex according to any of <1> to <3> above, wherein $R^1$ is a hydrogen atom or a fluorine atom.

<5> The iridium complex according to any of <1> to <4> above, wherein $R^2$ is a hydrogen atom, an alkyl group having 1 to 30 carbon atoms which may have a substituent, or an aryl group having 6 to 60 carbon atoms which may have a substituent.

<6> The iridium complex according to any of <1> to <4> above, wherein $R^2$ is a trifluoromethyl group.

<7> The iridium complex according to any of <1> to <6> above, wherein $R^3$ is a hydrogen atom, an alkyl group having 1 to 30 carbon atoms which may have a substituent, or an aryl group having 6 to 60 carbon atoms which may have a substituent.

<8> The iridium complex according to any of <1> to <6> above, wherein $R^3$ is a fluorine atom.

<9> The iridium complex according to any of <1> to <8> above, wherein any of 1e to $R^4$ is substituted by at least one dendron.

<10> The iridium complex according to any of <1> to <9> above, wherein $R^a$ is an alkyl group having 2 to 30 carbon atoms.

<11> The iridium complex according to any of <1> to <9> above, wherein $R^a$ is an n-decyl group.

<12> The iridium complex according to any of <2> and <4> to <11> above, wherein m=3 and n=0.

<13> The iridium complex according to any of <2> to <11> above, wherein m=2 and n=1.

<14> The iridium complex according to any of <2> to <11> above, wherein m=1 and n=2.

<15> A luminescent material comprising an iridium complex according to any of <1> to <14> above.

<16> A luminescent element using a luminescent material according to <15> above.

Advantageous Effects of Invention

Since a novel iridium complex of the present invention efficiently exhibits highly bright luminescence in the visible light region with low power consumption, a luminescent element using the compound is suitable for fields such as display elements, displays, backlights, electrophotography, illumination light sources, recording light sources, exposing light sources, readout light sources, signs, sigh boards, and interiors. Moreover, the iridium complex of the present invention can also be applied to medical use, oxygen sensors, materials for photographs, UV absorbing materials, laser dyes, dyes for color filters, color conversion filters, luminescent probes for cell imaging, optical communications, etc.

DESCRIPTION OF EMBODIMENTS

Figure 1:
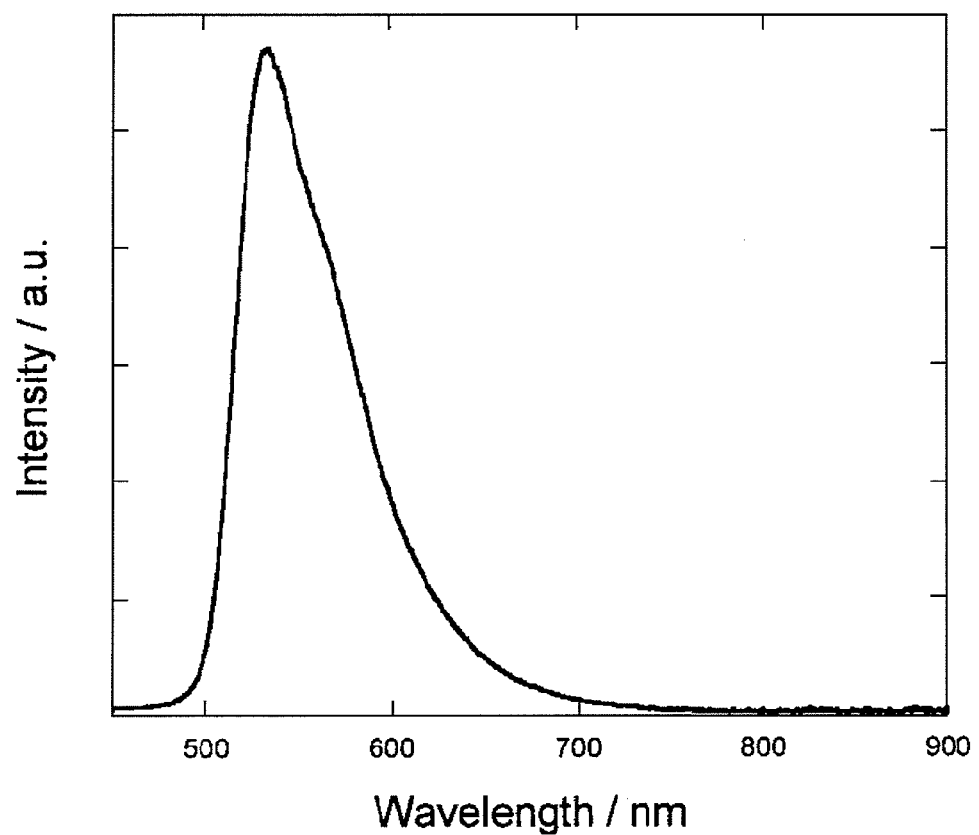
FIG. 1 It is the luminescence spectrum of compound (43) of the present invention in THF at room temperature under an argon atmosphere. Excitation light is 350 nm.
Figure 2:
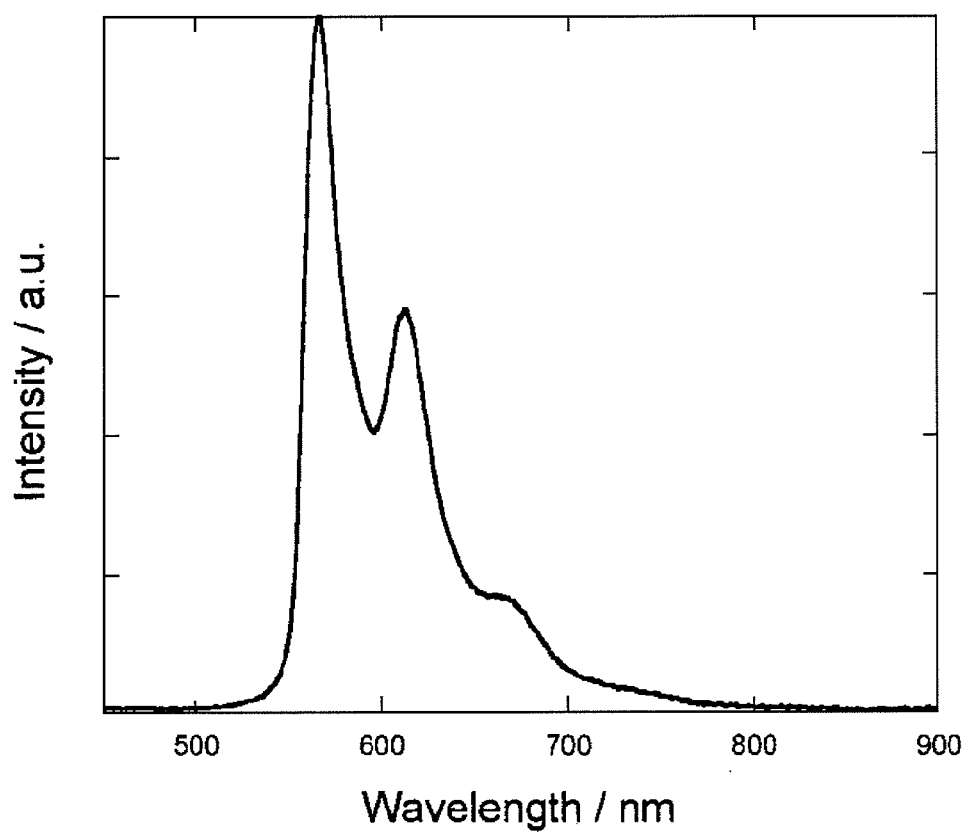
FIG. 2 It is the luminescence spectrum of compound (53) of the present invention in THF at room temperature under an argon atmosphere. Excitation light is 350 nm.
Figure 3:
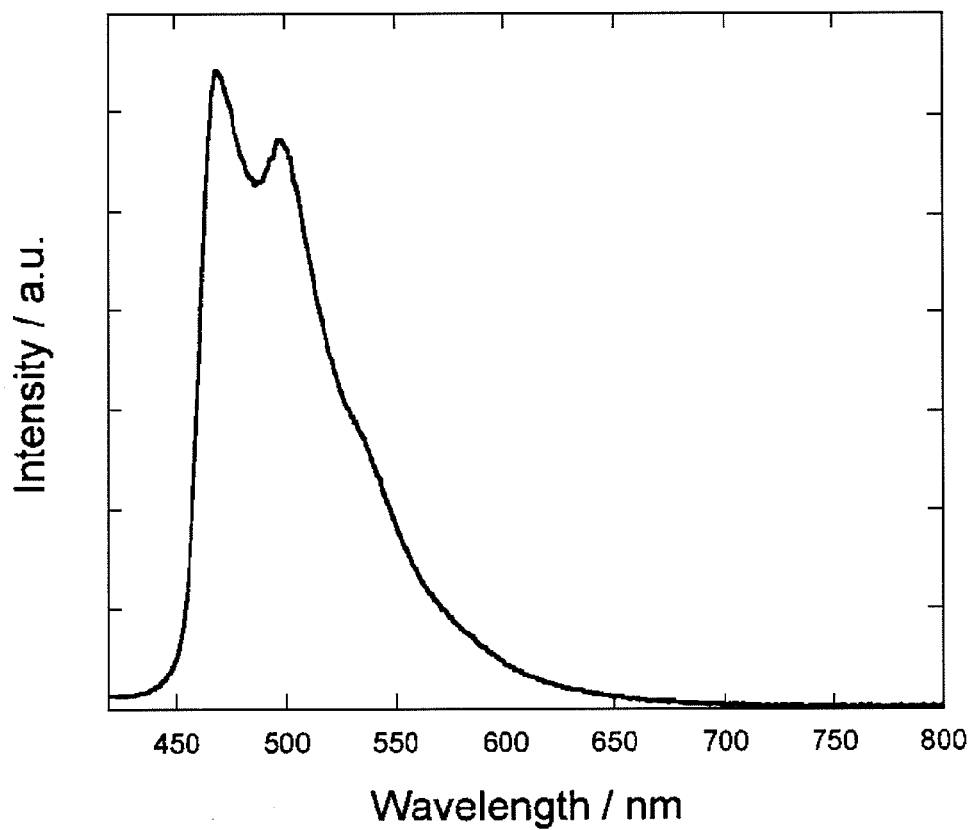
FIG. 3 It is the luminescence spectrum of compound (82) of the present invention in THF at room temperature under an argon atmosphere. Excitation light is 350 nm.

An iridium complex according to the present invention has a substructure represented by formula (1) and, preferably, is represented by formula (2), and a luminescent element exhibiting excellent luminescence in the visible light region is obtained by allowing these iridium complexes to be contained in a luminescent layer or a plurality of organic compound layers including a luminescent layer in the luminescent element.

Hereinafter, the present invention will be described in more detail.

The iridium complex according to the present invention is characterized by having a 2-phenylpyrimidine-based ligand of a particular structure. The present inventor has found that the thermal stability and, particularly the emission quantum yield in a solid state, of the iridium complex largely increase by introducing an alkyl group having 2 to 30 carbon atoms which may have a substituent in $R^a$ described in formula (1) or (2).

When the 2-phenylpyrimidine-based ligand and iridium, which is a central metal, form a bond, intersystem crossing from an excited singlet state to an excited triplet state is promoted by heavy atom effect and as a result, the iridium complex of the present invention efficiently exhibits phosphorescence emission in the visible light region.

The iridium complex according to the present invention may contain an isomer (e.g., facial forms, meridional forms, and isomers described in Japanese Patent Application Laid-Open Publication No. 2006-278781 or Japanese Patent Application Laid-Open Publication No. 2008-288254).

Moreover, the iridium complex according to the present invention is neutral or ionic, more preferably neutral or cationic, particularly preferably a neutral iridium complex.

Among the iridium complexes according to the present invention, one in which the emission quantum yield in a solution (under air, under an inert gas atmosphere, or under deaeration, preferably under in an inert gas atmosphere or under deaeration) at room temperature is 0.01 or more is preferable, one in which it is 0.1 or more is more preferable, one in which it is 0.4 or more is particularly preferable, and one in which it is 0.5 or more is most preferable. Moreover, among the iridium complexes of the present invention, one in which the emission quantum yield in a solid state is 0.01 or more is preferable, one in which it is 0.05 or more is more preferable, one in which it is 0.1 or more is particularly preferable, and one in which it is 0.3 or more is most preferable. Here, the emission quantum yield in a solid state is a value determined by directly irradiating the iridium complex in a solid state with excitation light without doping with a host material or the like and measuring the luminescence.

For removing dissolved oxygen, it is preferred that the measurement of the emission quantum yield in a solution should be performed after aerating inert gas (argon gas or nitrogen gas) to a solution in which the iridium complex is dissolved or should be performed after freezing/deaerating a solution in which the iridium complex is dissolved. Any of an absolute method and a relative method may be used as a measurement method for the emission quantum yield. The relative method can measure the emission quantum yield by the comparison of a luminescence spectrum with a reference substance (kinin sulfate, etc.). In the absolute method, the measurement of the emission quantum yield in a solution or in a solid state is possible by using a commercially available apparatus (absolute PL quantum yield measurement apparatus (C9920) manufactured by Hamamatsu Photonics K.K.). Although the emission quantum yield in a solution can be measured using various solvents, the iridium complex according to the present invention needs only to achieve the emission quantum yield described above in any of arbitrary solvents.

Among the iridium complexes of the present invention, one in which the emission maximum wavelength of a luminescence spectrum in a solution or in a solid state is in the range of 300 nm to 900 nm is preferable, and one in which it is in the range of 400 nm to 800 nm is more preferable.

In regard to the number of valence of iridium, trivalence or tetravalence is preferable, and trivalence is more preferable.

The symbols (m, n, Q, k, L, $R^a$, and $R^1$ to $R^{76}$) described in formulas (1) to (11) will be described below.

m represents an integer of 1 to 3, n represents an integer of 0 to 2, and m+n=3. m=2 or 3 is preferable, and n=0 or 1 is preferable. In m=3 and n=0, facial forms and meridional forms exist as geometric isomers, with facial forms preferred.

Q represents a counter ion. There is no particular limitation as a counter ion, which is however, for example, an alkali metal ion, an alkaline earth metal ion, a halogen ion, a perchlorate ion, a $PF_6$ ion, an ammonium ion, a $CF_3CF_2CF_2COO$ ion, a $SbF_6$ ion, a dicyanamide ion, a bis(trifluoromethanesulfonyl)amide ion, a borate ion, a trifluoroacetic acid ion, a trifluoromethanesulfonate ion, a phosphonium ion, or a tetrakis[3,5-bis(trifluoromethyl)phenyl]borate ion, and one that is preferred is a halogen ion, a perchlorate ion, a $PF_6$ ion, a $CF_3CF_2CF_2COO$ ion, a $SbF_6$ ion, a dicyanamide ion, a bis(trifluoromethanesulfonyl)amide ion, a borate ion, a trifluoroacetic acid ion, a trifluoromethanesulfonate ion, or a tetrakis[3,5-bis(trifluoromethyl)phenyl]borate ion.

k represents an integer of 0 to 2. k is preferably 0 or 1, more preferably 0.

L is a bidentate ligand, a neutral bidentate ligand or anionic bidentate ligand is preferable, and an anionic bidentate ligand is more preferable, with a monoanionic bidentate ligand particularly preferred.

Moreover, it is preferred that L should be a bidentate ligand forming a Ir-nitrogen bond and a Ir-carbon bond, a bidentate ligand forming a Ir-nitrogen bond and a Ir-oxygen bond, a bidentate ligand forming two Ir-oxygen bonds, or a bidentate ligand forming two Ir-nitrogen bonds.

The bidentate ligand forming a Ir-nitrogen bond and a Ir-carbon bond is, for example, a 2-phenylpyridine derivative, a 2-phenylpyrimidine derivative, a 2-phenylquinoline derivative, a 1-phenylisoquinoline derivative, a 3-phenylisoquinoline derivative, a 2-(2-benzothiophenyl)pyridine derivative, a 2-thienylpyridine derivative, a 1-phenylpyrazole derivative, a 1-phenyl-1H-indazole derivative, a 2-phenylbenzothiazole derivative, a 2-phenylthiazole derivative, a 2-phenylbenzoxazole derivative, a 2-phenyloxazole derivative, a 2-furanylpyridine derivative, a 2-(2-benzofuranyl)pyridine derivative, a 7,8-benzoquinoline derivative, a 7,8-benzoquinoxaline derivative, a dibenzo[f,h]quinoline derivative, a dibenzo[f,h]quinoxaline derivative, a benzo[h]-5,6-dihydroquinoline derivative, a 9-(2-pyridyl)carbazole derivative, a 1-(2-pyridyl)indole derivative, a 1-(1-naphthyl)isoquinoline derivative, a 1-(2-naphthyl)isoquinoline derivative, a 2-(2-naphthyl)quinoline derivative, a 2-(1-naphthyl)quinoline derivative, a 3-(1-naphthyl)isoquinoline derivative, a 3-(2-naphthyl)isoquinoline derivative, a 2-(1-naphthyl)pyridine derivative, a 2-(2-naphthyl)pyridine derivative, a 6-phenylphenanthridine derivative, a 6-(1-naphthyl)phenanthridine derivative, a 6-(2-naphthyl)phenanthridine derivative, a benzo[c]acridine derivative, a benzo[c]phenazine derivative, a dibenzo[a,c]acridine derivative, a dibenzo[a,c]phenazine derivative, a 2-phenylquinoxaline derivative, a 2,3-diphenylquinoxaline derivative, a 2-benzylpyridine derivative, a 2-phenylbenzimidazole derivative, a 3-phenylpyrazole derivative, a 4-phenylimidazole derivative, a 1-phenylimidazole derivative, a 4-phenyltriazole derivative, a 5-phenyltetrazole derivative, a 2-alkenylpyridine derivative, a 5-phenyl-1,2,4-triazole derivative, an imidazo[1,2-f]phenanthridine derivative, a [1,2,4]triazolo[1,5-f]phenanthridine derivative, a [1,2,4]triazolo[4,3-f]phenanthridine derivative, a 1,2-diphenylimidazole derivative, a 1,5-diphenyl-1,2,4-triazole derivative, or a 3,4-diphenyl-1,2,4-triazole derivative, preferably a 2-phenylpyridine derivative, a 2-phenylpyrimidine derivative, a 2-phenylquinoline derivative, a 1-phenylisoquinoline derivative, a 1-phenylimidazole derivative, a 5-phenyl-1,2,4-triazole derivative, an imidazo[1,2-f]phenanthridine derivative, a [1,2,4]triazolo[1,5-f]phenanthridine derivative, a [1,2,4]triazolo[4,3-f]phenanthridine derivative, a 1,2-diphenylimidazole derivative, a 1,5-diphenyl-1,2,4-triazole derivative, or a 3,4-diphenyl-1,2,4-triazole derivative, more preferably a 2-phenylpyridine derivative, a 2-phenylpyrimidine derivative, a 2-phenylquinoline derivative, a 1-phenylisoquinoline derivative, an imidazo[1,2-f]phenanthridine derivative, or a 1,2-diphenylimidazole derivative.

Specifically, there is description in International Publication No. WO2004-085450, International Publication No. WO2006-075905, International Publication No. WO2002-44189, International Publication No. WO2002-45466, International Publication No. WO2006-046980, International Publication No. WO2006-059758, Japanese Patent Application Laid-Open Publication No. 2006-182772, Japanese Patent Application Laid-Open Publication No. 2006-151888, Japanese Patent Application Laid-Open Publication No. 2006-151887, Japanese Patent Application Laid-Open Publication No. 2006-93665, Japanese Patent Application Laid-Open Publication No. 2006-100393, International Publication No. WO2004-101707, International Publication No. WO2005-073339, International Publication No. WO2005-056719, International Publication No. WO2005-056716, International Publication No. WO2005-056715, International Publication No. WO2005-048315, International Publication No. WO2005-033244, International Publication No. WO2004-081019, International Publication No. WO2004-045000, International Publication No. WO2004-044089, International Publication No. WO2004-026886, Japanese Patent Application Laid-Open Publication No. 2002-234894, Japanese Patent Application Laid-Open Publication No. 2002-226495, Japanese Patent Application Laid-Open Publication No. 2003-59667, Japanese Patent Application Laid-Open Publication No. 2001-345183, Japanese Patent Application Laid-Open Publication No. 2001-247859, Japanese Patent Application Laid-Open Publication No. 2003-7469, Japanese Patent Application Laid-Open Publication No. 2003-73388, Japanese Patent Application Laid-Open Publication No. 2003-109758, Japanese Patent Application Laid-Open Publication No. 2003-123982, Japanese Patent Application Laid-Open Publication No. 2003-133074, Japanese Patent Application Laid-Open Publication No. 2003-131464, Japanese Patent Application Laid-Open Publication No. 2003-131463, Japanese Patent Application Laid-Open Publication No. 2004-107441, Japanese Patent Application Laid-Open Publication No. 2004-67658, Japanese Patent Application Laid-Open Publication No. 2003-342284, Japanese Patent Application Laid-Open Publication No. 2005-29784, Japanese Patent Application Laid-Open Publication No. 2005-29783, Japanese Patent Application Laid-Open Publication No. 2005-29782, Japanese Patent Application Laid-Open Publication No. 2005-23072, Japanese Patent Application Laid-Open Publication No. 2005-23071, Japanese Patent Application Laid-Open Publication No. 2005-23070, Japanese Patent Application Laid-Open Publication No. 2005-2101, Japanese Patent Application Laid-Open Publication No. 2005-2053, Japanese Patent Application Laid-Open Publication No. 2005-78996, Japanese Patent Application Laid-Open Publication No. 2005-68110, Japanese Patent Application Laid-Open Publication No. 2005-60374, Japanese Patent Application Laid-Open Publication No. 2005-44802, Japanese Patent Application Laid-Open Publication No. 2005-29785, Japanese Patent Application Laid-Open Publication No. 2005-104843, Japanese Patent Application Laid-Open Publication No. 2005-97549, Japanese Patent Application Laid-Open Publication No. 2005-220136, Japanese Patent Application Laid-Open Publication No. 2005-213348, Japanese Patent Application Laid-Open Publication No. 2005-170851, Japanese Patent Application Laid-Open Publication No. 2005-163036, Japanese Patent Application Laid-Open Publication No. 2005-154396, Japanese Patent Application Laid-Open Publication No. 2005-272411, Japanese Patent Application Laid-Open Publication No. 2005-327526, Japanese Patent Application Laid-Open Publication No. 2005-325048, Japanese Patent Application Laid-Open Publication No. 2005-314663, Japanese Patent Application Laid-Open Publication No. 2006-13222, Japanese Patent Application Laid-Open Publication No. 2006-8688, Japanese Patent Application Laid-Open Publication No. 2006-80419, Japanese Patent Application Laid-Open Publication No. 2006-76969, International Publication No. WO2002-15645, International Publication No. WO2002-02714, International Publication No. WO2002-064700, International Publication No. WO2003-033617, International Publication No. WO2003-000661, International Publication No. WO2002-081488, U.S. Patent No. 2006-0251923, Japanese Patent Application Laid-Open Publication No. 2007-137872, International Publication No. WO2010-061989, International Publication No. WO2008-156879, International Publication No. WO2010-068876, International Publication No. WO2009-061926, International Publication No. WO2008-054584, International Publication No. WO2006-046980, etc.

Although examples of the structural formula of the bidentate ligand forming a Ir-nitrogen bond and a Ir-carbon bond are shown in Table 1 to Table 2, the present invention is not limited to this. R in Table 1 to Table 2 is a hydrogen atom or a substituent, and the desirable range is the same as $R^1$ to $R^{76}$ described later. * in Table 1 and Table 2 represents a binding site for iridium.

TABLE 1

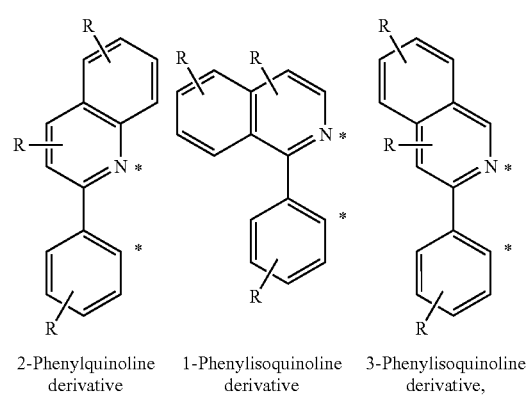

2-Phenylquinoline derivative    1-Phenylisoquinoline derivative    3-Phenylisoquinoline derivative,

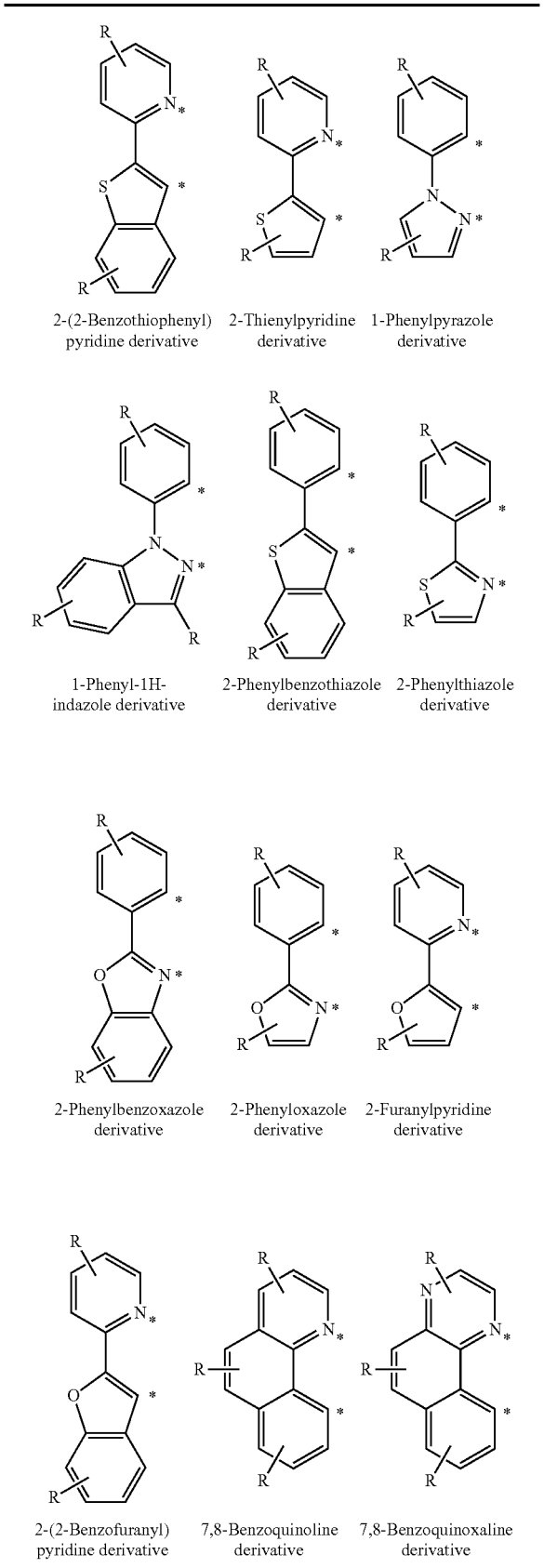
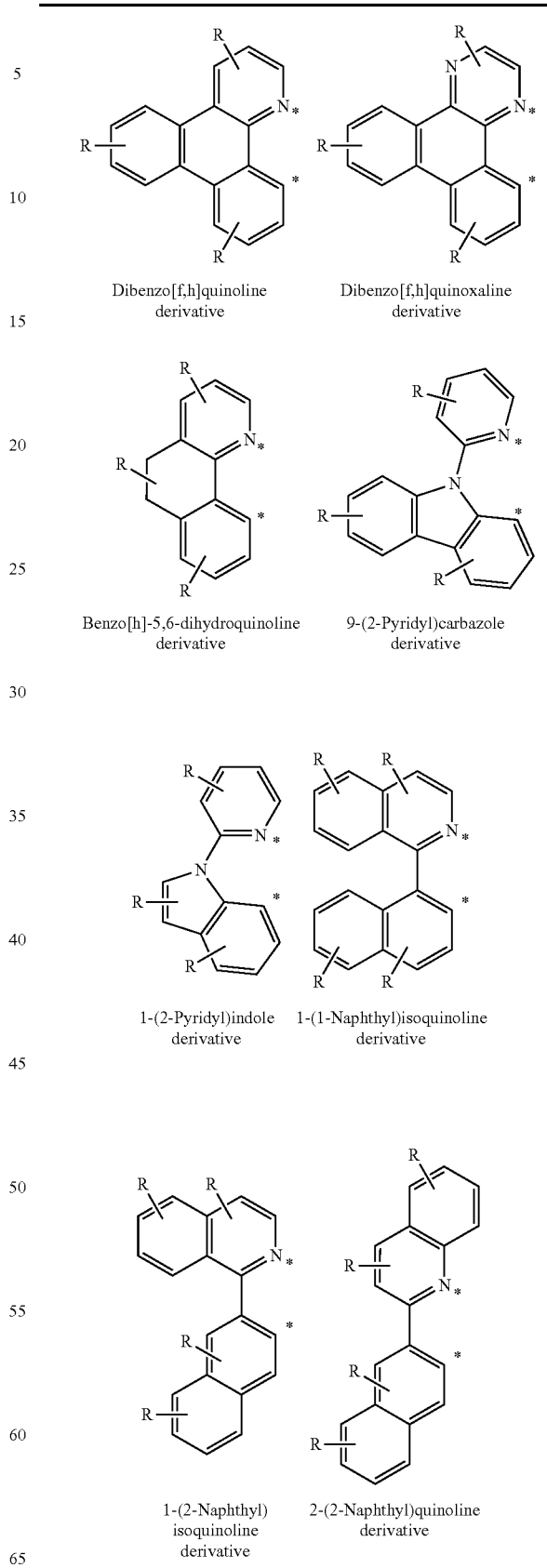

TABLE 1-continued

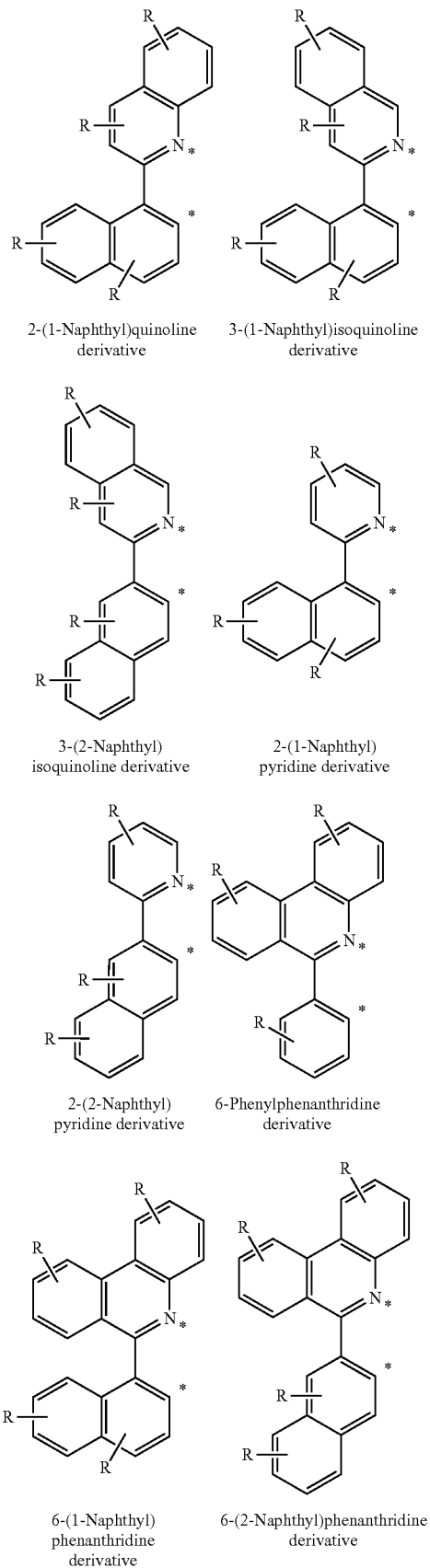

2-(1-Naphthyl)quinoline derivative 3-(1-Naphthyl)isoquinoline derivative 3-(2-Naphthyl) isoquinoline derivative 2-(1-Naphthyl) pyridine derivative 2-(2-Naphthyl) pyridine derivative 6-Phenylphenanthridine derivative 6-(1-Naphthyl) phenanthridine derivative 6-(2-Naphthyl)phenanthridine derivative TABLE 1-continued

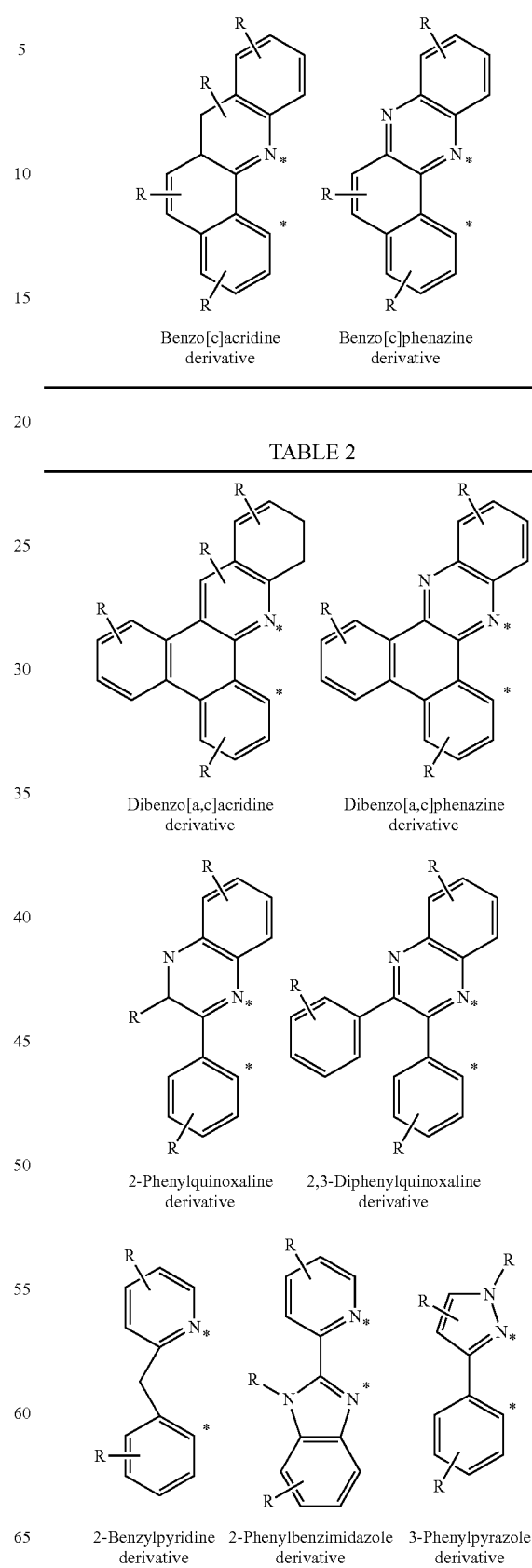

Benzo[c]acridine derivative

Benzo[c]phenazine derivative

TABLE 2

Dibenzo[a,c]acridine derivative

Dibenzo[a,c]phenazine derivative

2-Phenylquinoxaline derivative 2,3-Diphenylquinoxaline derivative

2-Benzylpyridine derivative

2-Phenylbenzimidazole derivative

3-Phenylpyrazole derivative

TABLE 2-continued

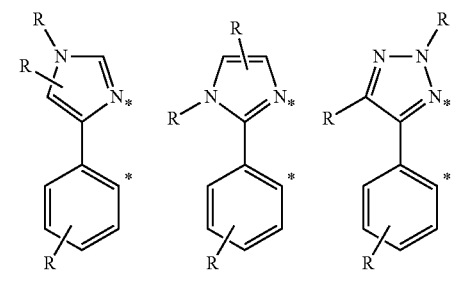

4-Phenylimidazole derivative    1-Phenylimidazole derivative    4-Phenyltriazole derivative

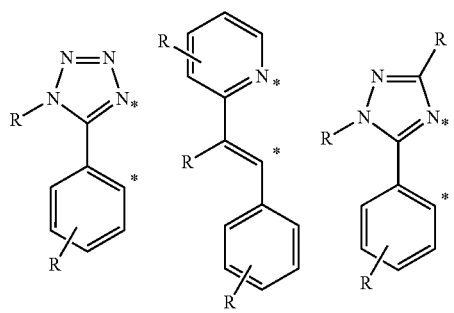

5-Phenyltetrazole derivative    2-Alkenylpyridine derivative    5-Phenyl-1,2,4-triazole derivative

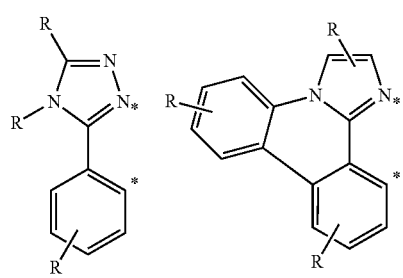

3-Phenyl-1,2,4-triazole derivative    Imidazo[1,2-f]phenanthridine derivative

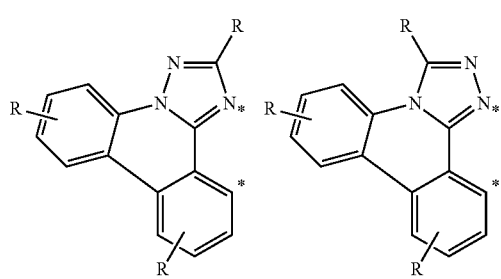

[1,2,4]Triazolo[1,5-f]phenanthridine derivative    [1,2,4]Triazolo[4,3-f]phenanthridine derivative

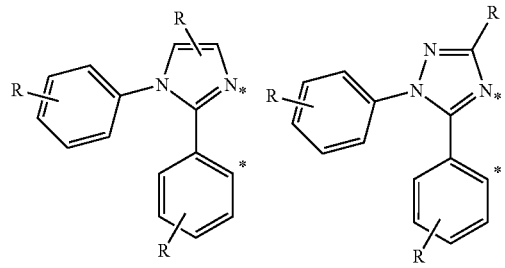

1,2-Diphenylimidazole derivative    1,5-Diphenyl-1,2,4-triazole derivative

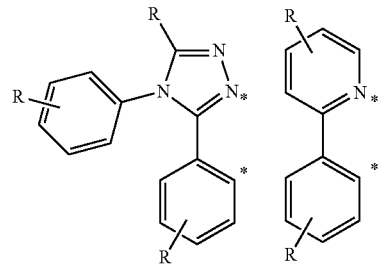

3,4-Diphenyl-1,2,4-triazole derivative    2-Phenylpyridine derivative

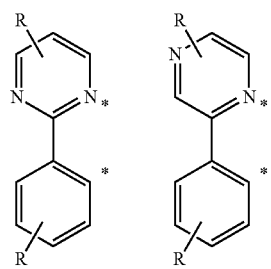

2-Phenylpyrimidine derivative    2-Phenylpyrazine derivative

The bidentate ligand forming a Ir-nitrogen bond and a Ir-oxygen bond is, for example, a picolinic acid derivative, a pyridinesulfonic acid derivative, a quinolinesulfonic acid derivative, or a quinolinecarboxylic acid derivative, and a picolinic acid derivative is preferable. Specifically, there is description in Japanese Patent Application Laid-Open Publication No. 2006-16394, Japanese Patent Application Laid-Open Publication No. 2006-307210, Japanese Patent Application Laid-Open Publication No. 2006-298900, International Publication No. WO2006-028224, International Publication No. WO2006-097717, Japanese Patent Application Laid-Open Publication No. 2004-111379, Japanese Patent Application Laid-Open Publication No. 2005-29785, etc.

The bidentate ligand forming two Ir-oxygen bonds is, for example, a β-diketone derivative, a carboxylic acid derivative, or a tropolone derivative, and a β-diketone derivative is preferable. Specifically, there is description in Japanese Patent Application Laid-Open Publication No. 2005-35902, Japanese Patent Application Laid-Open Publication No. 2004-349224, Japanese Patent Application Laid-Open Publication No. 2006-28101, Japanese Patent Application Laid-Open Publication No. 2005-29785, etc.

The bidentate ligand forming two Ir-nitrogen bonds is, for example, a 2,2'-bipyridine derivative, a 1,10-phenanthroline derivative, a 2,2'-biquinoline derivative, a 2,2'-dipyridylamine derivative, an imidazole derivative, a pyrazolylborate derivative, or a pyrazole derivative. Specifically, there is description in Japanese Patent Application Laid-Open Publication No. 2005-298483, Japanese Patent Application Laid-Open Publication No. 2006-213720, Japanese Patent Application Laid-Open Publication No. 2003-133074, etc.

A structure particularly preferable as L is shown in formulas (3) to (11). Specifically, the monoanionic bidentate ligand is (3) to (6), (10), or (11), and the neutral bidentate ligand is (7) to (9).

$R^a$ is an alkyl group having 2 to 30 carbon atoms (preferably 2 to 20 carbon atoms, more preferably 3 to 20 carbon atoms, particularly preferably 5 to 20 carbon atoms, most preferably 10 to 20 carbon atoms) which may have a substituent.

A case in which the alkyl group having 2 to 30 carbon atoms which may have a substituent is introduced in $R^a$ is preferable and very preferable, particularly from the viewpoint of luminescent element preparation using a coating process, because the solubility of the iridium complex, which is the compound of the present invention, in a solvent (dichloromethane, chloroform, toluene, THF, xylene, etc.) largely increases, improving the operability of synthesis or purification.

Hereinafter, $R^a$ will be described specifically. Examples of the alkyl group which may have a substituent include an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a benzyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a 1-nitroethyl group, a 2-nitroethyl group, a 1,2-dinitroethyl group, a 2,3-dinitro-t-butyl group, a 1,2,3-trinitropropyl group, a cyclopentyl group, a cyclohexyl group, a cyclooctyl group, and a 3,5-tetramethylcyclohexyl group. Among these, one that is preferred includes an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 1-pentylhexyl group, a 1-butylpentyl group, a 1-heptyloctyl group, a cyclohexyl group, a cyclooctyl group, and a 3,5-tetramethylcyclohexyl group.

$R^1$ to $R^{76}$ each independently represent a hydrogen atom or an alkyl group having 1 to 30 carbon atoms (preferably 1 to 20 carbon atoms, more preferably 1 to 15 carbon atoms, particularly preferably 1 to 10 carbon atoms, most preferably 1 to 5 carbon atoms) which may have a substituent, an aryl group having 6 to 60 carbon atoms (preferably 6 to 30 carbon atoms, more preferably 6 to 20 carbon atoms, particularly preferably 6 to 15 carbon atoms, most preferably 6 to 12 carbon atoms) which may have a substituent, an alkenyl group having 2 to 30 carbon atoms (preferably 2 to 30 carbon atoms, more preferably 2 to 20 carbon atoms, particularly preferably 2 to 15 carbon atoms, most preferably 2 to 10 carbon atoms) which may have a substituent, an alkynyl group having 2 to 30 carbon atoms (preferably 2 to 30 carbon atoms, more preferably 2 to 20 carbon atoms, particularly preferably 2 to 10 carbon atoms) which may have a substituent, an amino group having 0 to 30 carbon atoms (preferably 0 to 30 carbon atoms, more preferably 0 to 20 carbon atoms, particularly preferably 0 to 10 carbon atoms) which may have a substituent, a heterocyclic group having 1 to 60 carbon atoms (preferably 1 to 30 carbon atoms, more preferably 1 to 20 carbon atoms, particularly preferably 1 to 12 carbon atoms) which may have a substituent, an alkoxy group or alkylthio group having 1 to 30 carbon atoms (preferably 1 to 30 carbon atoms, more preferably 1 to 20 carbon atoms, particularly preferably 1 to 10 carbon atoms) which may have a substituent, an aryloxy group or arylthio group having 6 to 60 carbon atoms (preferably 6 to 30 carbon atoms, more preferably 6 to 20 carbon atoms, particularly preferably 6 to 15 carbon atoms, most preferably 6 to 12 carbon atoms) which may have a substituent, a heterocyclic oxy group or heterocyclic thio group having 1 to 60 carbon atoms (preferably 1 to 30 carbon atoms, more preferably 1 to 20 carbon atoms, particularly preferably 1 to 12 carbon atoms) which may have a substituent, an acyl group, an acyloxy group, an amide group, an acid imide group, an imine residue, a substituted silyl group, a substituted silyloxy group, a substituted silylthio group, a substituted silylamino group, a halogen atom (preferably a chlorine atom, a bromine atom, or a fluorine atom, more preferably a fluorine atom), a cyano group, a carboxyl group, or a trifluoromethyl group.

Examples of the alkyl group having 1 to 30 carbon atoms which may have a substituent include a methyl group which may have a substituent and the alkyl groups having 2 to 30 carbon atoms which may have a substituent exemplified in the description of $R^a$. Examples of the aryl group having 6 to 60 carbon atoms which may have a substituent include a phenyl group, a biphenyl-2-yl group, a biphenyl-3-yl group, a biphenyl-4-yl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 4'-methylbiphenylyl group, a 4''-t-butyl-p-terphenyl-4-yl group, an o-cumenyl group, an m-cumenyl group, a p-cumenyl group, a 2,3-xylyl group, a 3,4-xylyl group, a 2,5-xylyl group, a mesityl group, an m-quaterphenyl group, a 1-naphthyl group, and a 2-naphthyl group. Among these, one that is preferred is a phenyl group, a biphenyl-2-yl group, a biphenyl-3-yl group, a biphenyl-4-yl group, an m-terphenyl-4-yl group, an m-terphenyl-3-yl group, an m-terphenyl-2-yl group, a p-tolyl group, a 3,4-xylyl group, or an m-quaterphenyl-2-yl group, and one that is particularly preferred is a phenyl group, wherein these aryl groups may have a substituent. In addition, for example, dendron residues of the following formula described in Japanese Patent Application Laid-Open Publication No. 2009-149617 are included:

[Chemical Formula 09]

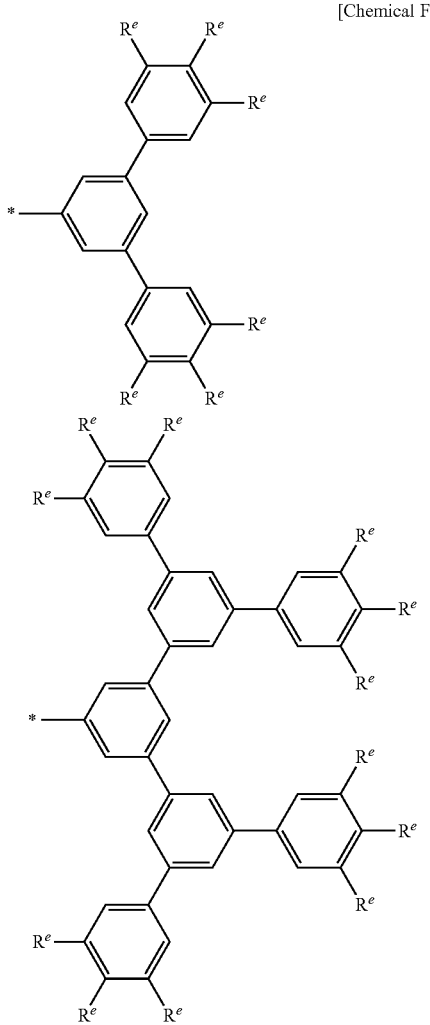

[Chemical Formula 10]

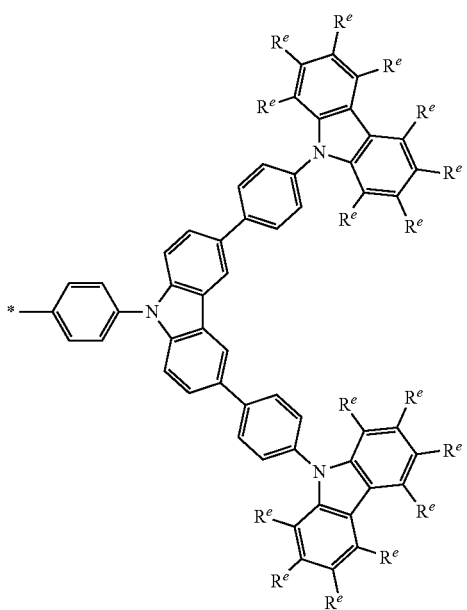

-continued

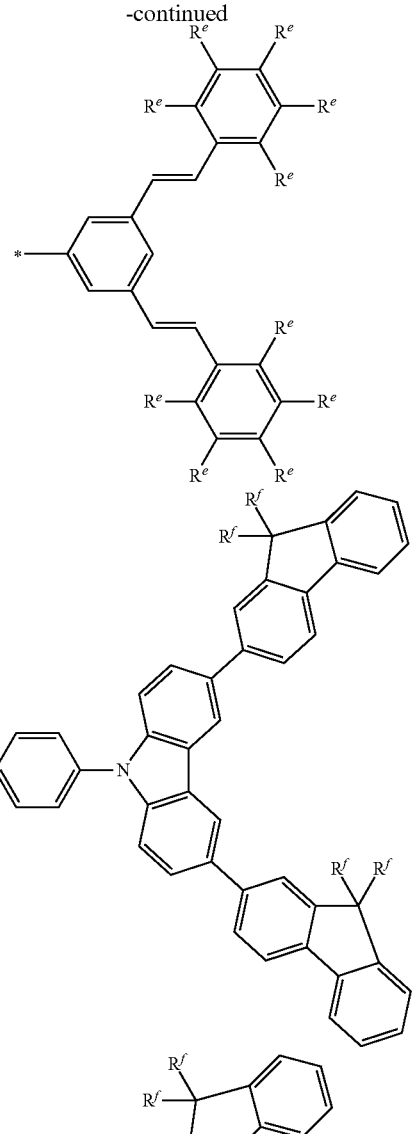

In the above formulas, $R^e$ represents a hydrogen atom, an alkyl group having 1 to 10 carbon atoms, or an alkoxy group having 1 to 10 carbon atoms, and some of hydrogen atoms in these substituents may be substituted by halogen atoms. A plurality of $R^e$s present may be the same or different, provided that at least one of $R^e$s is an alkyl group having 1 to 10 carbon atoms or an alkoxy group having 1 to 10 carbon atoms. Moreover, $R^f$ represents a linear or branched alkyl group having 1 to 10 carbon atoms. A plurality of R''s present may be the same or different. * represents a binding site for le to $R^{76}$ above.

Examples of the alkenyl group which may have a substituent include a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group, and one that is preferred includes a styryl group, a 2,2-diphenylvinyl group, and a 1,2-diphenylvinyl group.

Examples of the alkynyl group which may have a substituent include propargyl, 3-pentynyl, an ethynyl group, a methylethynyl group, a 1-propynyl group, a 2-propylenyl group, a heptynyl group, a cyclohexylethynyl group, a 2-propynyl group, a 1-butynyl group, a 2-butynyl group, a 1-pentynyl group, a 2-pentynyl group, a 1-hexynyl group, a 2-hexynyl group, and a 1-octynyl group. Diynyl groups such as a 1,3-butadiynyl group are also included in such an alkynyl group.

Examples of the amino group which may have a substituent include an amino group, a dibenzylamino group, a ditolylamino group, a methylamino group, a dimethylamino group, an ethylamino group, a diethylamino group, an n-propylamino group, a di-n-propylamino group, an isopropylamino group, a diisopropylamino group, an n-butylamino group, an s-butylamino group, an isobutylamino group, a t-butylamino group, an n-pentylamino group, an n-hexylamino group, a cyclohexylamino group, an n-heptylamino group, an n-octylamino group, a 2-ethylhexylamino group, an n-nonylamino group, an n-decylamino group, a 3,7-dimethyloctylamino group, an n-laurylamino group, a cyclopentylamino group, a dicyclopentylamino group, a cyclohexylamino group, a dicyclohexylamino group, a pyrrolidinyl group, a piperidinyl group, a ditrifluoromethylamino group, a phenylamino group, a diphenylamino group, a $C_1$ to $C_{12}$ alkoxyphenylamino group, a di($C_1$ to $C_{12}$ alkoxyphenyl)amino group, a di($C_1$ to $C_{12}$ alkylphenyl)amino group, a 1-naphthylamino group, a 2-naphthylamino group, a pentafluorophenylamino group, a pyridinylamino group, a pyridazinylamino group, a pyrimidinylamino group, a pyrazinylamino group, a triazinylamino group, a phenyl-$C_1$ to $C_{12}$ alkylamino group, a $C_1$ to $C_{12}$ alkoxyphenyl-$C_1$ to $C_{12}$ alkylamino group, a $C_1$ to $C_{12}$ alkylphenyl-$C_1$ to $C_{12}$ alkylamino group, a di($C_1$ to $C_{12}$ alkoxyphenyl-$C_1$ to $C_{12}$ alkyl)amino group, a di($C_1$ to $C_{12}$ alkylphenyl-$C_1$ to $C_{12}$ alkyl)amino group, a 1-naphthyl-$C_1$ to $C_{12}$ alkylamino group, and a 2-naphthyl-$C_1$ to $C_{12}$ alkylamino group.

Examples of the heterocyclic group which may have a substituent include a 1-pyrrolyl group, a 2-pyrrolyl group, a 3-pyrrolyl group, a pyrazinyl group, a 2-pyridinyl group, a 1-imidazolyl group, a 2-imidazolyl group, a 1-pyrazolyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 2-imidazopyridinyl group, a 3-imidazopyridinyl group, a 5-imidazopyridinyl group, a 6-imidazopyridinyl group, a 7-imidazopyridinyl group, a 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, β-carbolin-1-yl, β-carbolin-3-yl, β-carbolin-4-yl, β-carbolin-5-yl, β-carbolin-6-yl, β-carbolin-7-yl, β-carbolin-6-yl, β-carbolin-9-yl, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group. Among these, one that is preferred includes a 2-pyridinyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 2-imidazopyridinyl group, a 3-imidazopyridinyl group, a 5-imidazopyridinyl group, a 6-imidazopyridinyl group, a 7-imidazopyridinyl group, a 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 1-carbazolyl group, a 2-carbazolyl group, a 3-carbazolyl group, a 4-carbazolyl group, a 9-carbazolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group.

The alkoxy group or alkylthio group which may have a substituent is a group represented by —OY or —SY, and examples of Y include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

The aryloxy group or arylthio group which may have a substituent is a group represented by —OZ or —SZ, and examples of Z include a phenyl group, $C_1$ to $C_{12}$ alkoxyphenyl groups, $C_1$ to $C_{12}$ alkylphenyl groups, a 1-naphthyl group, a 2-naphthyl group, and a pentafluorophenyl group.

One example of the aryloxy group which may have a substituent includes dendron residues of the following formula described in Japanese Patent Application Laid-Open Publication No. 2009-149617:

[Chemical Formula 11]

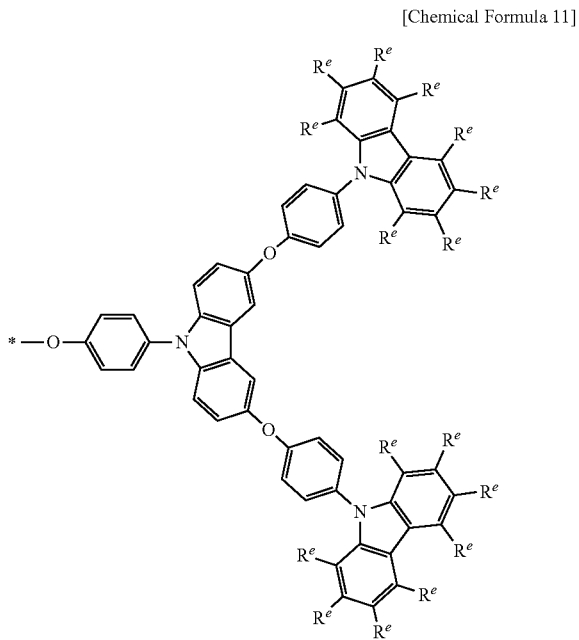

In the above formula, $R^e$ represents a hydrogen atom, an alkyl group having 1 to 10 carbon atoms, or an alkoxy group having 1 to 10 carbon atoms, and some of hydrogen atoms in these substituents may be substituted by halogen atoms. A plurality of $R^e$s present may be the same or different, provided that at least one of $R^e$s is an alkyl group having 1 to 10 carbon atoms or an alkoxy group having 1 to 10 carbon atoms. * represents a binding site for $R^1$ to $R^{76}$ above.

The heterocyclic oxy group or heterocyclic thio group which may have a substituent is a group represented by —OHet or —SHet, and examples of Het include a thienyl group, $C_1$ to $C_{12}$ alkoxythienyl groups, $C_1$ to $C_{12}$ alkylthienyl groups, a pyrrolyl group, $C_1$ to $C_{12}$ alkoxypyrrolyl groups, $C_1$ to $C_{12}$ alkylpyrrolyl group, a furyl group, $C_1$ to $C_{12}$ alkoxyfuryl groups, $C_1$ to $C_{12}$ alkylfuryl group, a pyridinyl group, $C_1$ to $C_{12}$ alkoxypyridinyl groups, $C_1$ to $C_{12}$ alkylpyridinyl group, a piperidinyl group, $C_1$ to $C_{12}$ alkoxypiperidinyl groups, $C_1$ to $C_{12}$ alkylpiperidinyl groups, a quinolyl group, and an isoquinolyl group. Of these, $C_1$ to $C_{12}$ alkoxypyridinyl groups and $C_1$ to $C_{12}$ alkylpyridinyl groups are preferable.

The number of carbon atoms in the acyl group described above is usually on the order of 2 to 20, with 2 to 18 preferred. Specific acyl groups include an acetyl group, propionyl group, a butyryl group, an isobutyryl group, a pivaloyl group, a benzoyl group, a trifluoroacetyl group, and a pentafluorobenzoyl group.

The number of carbon atoms in the acyloxy group described above is usually on the order of 2 to 20, with 2 to 18 preferred. Specific acyloxy groups include an acetoxy group, a propionyloxy group, a butyryloxy group, an isobutyryloxy group, a pivaloyloxy group, a benzoyloxy group, a trifluoroacetyloxy group, and a pentafluorobenzoyloxy group.

Examples of the substituted silyl group, substituted silyloxy group, substituted silylthio group, and substituted silylamino group described above include those in which the substituted silyl moiety is a triethylsilyl group, a triisopropylsilyl group, a t-butyldimethylsilyl group, or a t-butyldiphenylsilyl group.

The substituent which the alkyl group of $R^a$ and the alkyl group, aryl group, alkenyl group, alkynyl group, amino group, heterocyclic group, alkoxy group, alkylthio group, aryloxy group, arylthio group, heterocyclic oxy group, and heterocyclic thio group of $R^1$ to $R^{76}$ described above may have includes, in addition to those described above, further: alkyl groups such as a methyl group, an ethyl group, a propyl group, and a t-butyl group; aralkyl groups such as a benzyl group and a phenethyl group; alkoxyl groups such as a methoxyl group, an ethoxyl group, and a propoxyl group; aryl groups such as a phenyl group and a biphenyl group; heterocyclic groups such as a thienyl group, a pyrrolyl group, and a pyridinyl group; and aryloxyl groups such as a phenoxyl group; amino groups such as a dimethylamino group, a diethylamino group, a dibenzylamino group, a diphenylamino group, a ditolylamino group, and a dianisolylamino group; and a cyano group.

Hereinafter, $R^1$ to $R^{76}$ will be described further specifically.

Among those described above, a hydrogen atom, a halogen atom, an aryl group having 6 to 30 carbon atoms which may have a substituent, or an alkyl group having 1 to 20 carbon atoms which may have a substituent is more preferable as $R^1$, and a hydrogen atom, a fluorine atom, an aryl group having 6 to 12 carbon atoms which may have a substituent, or an alkyl group having 1 to 10 carbon atoms which may have a substituent is particularly preferable, with a hydrogen atom or a fluorine atom most preferred.

Among those described above, a hydrogen atom, a halogen atom, a trifluoromethyl group, a cyano group, an aryl group having 6 to 30 carbon atoms which may have a substituent, or an alkyl group having 1 to 20 carbon atoms which may have a substituent is more preferable as $R^2$, and a hydrogen atom, a trifluoromethyl group, an aryl group having 6 to 12 carbon atoms which may have a substituent, or an alkyl group having 1 to 10 carbon atoms which may have a substituent is particularly preferable.

Among those described above, a hydrogen atom, a halogen atom, an aryl group having 6 to 30 carbon atoms which may have a substituent, or an alkyl group having 1 to 20 carbon atoms which may have a substituent is more preferable as $R^3$, and a hydrogen atom, a fluorine atom, an aryl group having 6 to 12 carbon atoms which may have a substituent, or an alkyl group having 1 to 10 carbon atoms which may have a substituent is particularly preferable.

Among those described above, a hydrogen atom, a trifluoromethyl group, or an alkyl group having 1 to 10 carbon atoms which may have a substituent is more preferable as $R^4$, and a hydrogen atom or an alkyl group having 1 to 5 carbon atoms which may have a substituent is particularly preferable, with a hydrogen atom most preferred.

Among those described above, a trifluoromethyl group, an aryl group having 6 to 12 carbon atoms which may have a substituent, or an alkyl group having 1 to 10 carbon atoms which may have a substituent is more preferable as $R^{13}$ and $R^{15}$, and an alkyl group having 1 to 5 carbon atoms which may have a substituent is particularly preferable, with an alkyl group having 1 to 3 carbon atoms which may have a substituent most preferred.

Among those described above, a hydrogen atom or an alkyl group having 1 to 10 carbon atoms which may have a substituent is more preferable as $R^{14}$ and $R^{20}$ to $R^{31}$, and a hydrogen atom or an alkyl group having 1 to 5 carbon atoms which may have a substituent is particularly preferable, with a hydrogen atom most preferred.

Among those described above, a hydrogen atom, an alkyl group having 1 to 20 carbon atoms which may have a substituent, an aryl group having 6 to 30 carbon atoms which may have a substituent, or a heterocyclic group having 1 to 20 carbon atoms which may have a substituent is more preferable as $R^{52}$, and a hydrogen atom, an alkyl group having 1 to 10 carbon atoms which may have a substituent, or an aryl group having 6 to 12 carbon atoms which may have a substituent is particularly preferable.

Among those described above, a hydrogen atom, a halogen atom, a trifluoromethyl group, a cyano group, a carboxyl group, an alkyl group having 1 to 20 carbon atoms which may have a substituent, an aryl group having 6 to 30 carbon atoms which may have a substituent, or a heterocyclic group having 1 to 20 carbon atoms which may have a substituent is more preferable as $R^5$ to $R^{12}$, $R^{16}$ to $R^{19}$, $R^{32}$ to $R^{51}$, $R^{53}$ to $R^{58}$, $R^{60}$ to $R^{62}$, and $R^{64}$ to $R^{76}$, and a hydrogen atom, an alkyl group having 1 to 10 carbon atoms which may have a substituent, or an aryl group having 6 to 12 carbon atoms which may have a substituent is particularly preferable.

Among those described above, a hydrogen atom, a halogen atom, a trifluoromethyl group, a cyano group, a carboxyl group, an alkyl group having 1 to 20 carbon atoms which may have a substituent, an aryl group having 6 to 30 carbon atoms which may have a substituent, or a heterocyclic group having 1 to 20 carbon atoms which may have a substituent is more preferable as $R^{59}$ and $R^{63}$, and a hydrogen atom, an alkyl group having 1 to 10 carbon atoms which may have a substituent, or an aryl group having 6 to 12 carbon atoms which may have a substituent is particularly preferable, with an alkyl group having 1 to 5 carbon atoms which may have a substituent most preferred.

Furthermore, it is also preferred that two or more adjacent substituents of $R^1$ to $R^{76}$ should be bonded to each other to form a saturated or unsaturated carbon ring or a saturated or unsaturated heterocyclic ring. Particularly, from the viewpoint of shifting the luminescence of the iridium complex to a long-wavelength side, it is preferred that $R^1$ to $R^3$ should be bonded to form a naphthalene skeleton or acenaphthene skeleton as in the following formula. Here, $R^b$ is a hydrogen atom or a substituent, and the desirable range is also the same as $R^1$ to $R^{76}$.

[Chemical Formula 12]

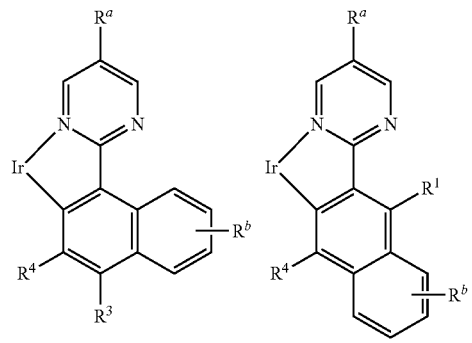

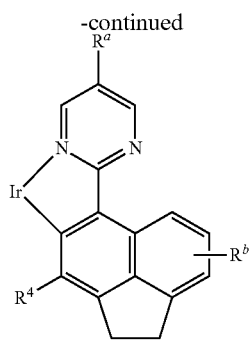

In the case where $R^2$ is an aryl group which may have a substituent, it is also preferred to adopt a dendrimer structure as described in Japanese Unexamined Patent Application Publication No. 2005-521210, Japanese Unexamined Patent Application Publication No. 2005-537321, Japanese Unexamined Patent Application Publication No. 2005-537354, Japanese Patent Application Laid-Open Publication No. 2008-174499, Japanese Unexamined Patent Application Publication No. 2008-538742, Japanese Patent Application Laid-Open Publication No. 2009-149617, etc.

In regard to the iridium complex according to the present invention, it has been revealed that it exhibits a high emission quantum yield, particularly in a solid state. The present inventor has assumed as to its reason that the alkyl group having 2 to 30 carbon atoms which may have a substituent is introduced at the particular site $R^a$, whereby the influence of concentration quenching decreases, resulting in strong luminescence even in a solid state.

Moreover, in regard to the iridium complex according to the present invention, it is possible to adjust an emission wavelength by changing L. In this field, it is considered that L does not directly contribute to the luminescence properties of a metal complex but may slightly change the luminescence properties, and it is called an ancillary ligand (see e.g., Japanese Unexamined Patent Application Publication No. 2006-513278).

Meanwhile, it is considered that the 2-phenylpyrimidine-based ligand described in formula (1) or (2) principally contributes to the luminescence properties of the iridium complex of the present invention, as described above. Thus, its emission wavelength can be changed according to application by combining the bidentate ligand with the conventionally known ancillary ligand described in the prior document.

Moreover, it is also possible to control the emission wavelength of the metal complex of the present invention by a method of introducing a substituent to $R^1$ to $R^4$. For example, luminescence shifts toward short wavelengths by introducing a fluorine atom to $R^1$ or $R^3$. Moreover, luminescence shifts toward short wavelengths by introducing a trifluoromethyl group to $R^2$ or $R^4$. These iridium complexes can be used preferably as blue luminescent materials. On the other hand, luminescence shifts toward long wavelengths by introducing an aryl group to $R^2$ or $R^3$.

Among the iridium complexes represented by formula (1), iridium complexes represented by formulas (12) to (20) are particularly preferable. Moreover, for the iridium complex represented by formula (2), it is also preferred to have the iridium complexes represented by formulas (12) to (20) as a substructure. Here, $R^c$ is a hydrogen atom or a substituent, and the desirable range is also the same as $R^1$ to $R^{76}$.

[Chemical Formula 13]

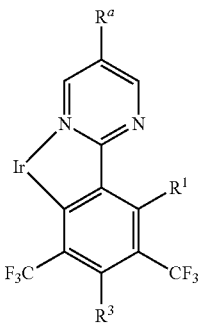

(12)

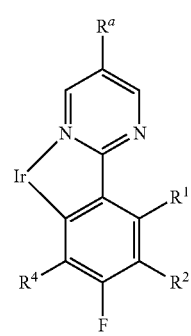

(13)

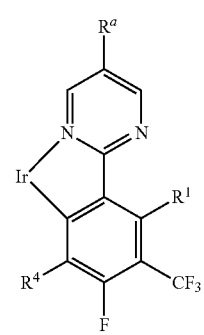

(14)

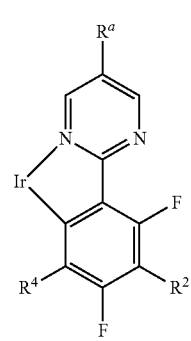

(15)

(16)
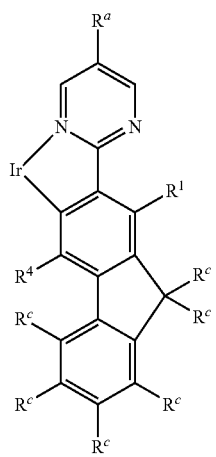

(17)
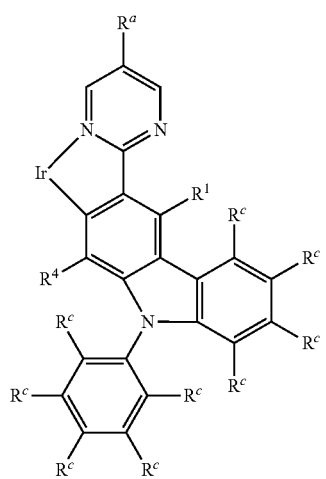

(18)
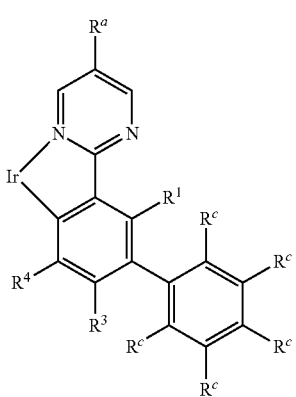

(19)
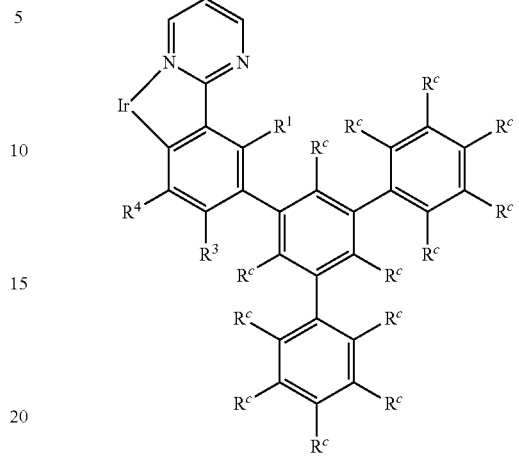

(20)
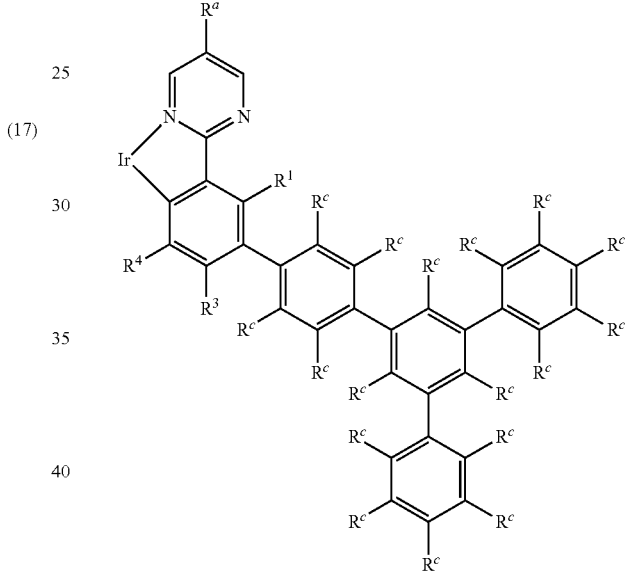

For producing the compound of the present invention represented by formula (1) or (2), synthesis can be performed with reference to known documents (Japanese Patent Application Laid-Open Publication No. 2002-105055, Japanese Patent Application Laid-Open Publication No. 2004-168755, Japanese Unexamined Patent Application Publication No. 2003-515897, Japanese Unexamined Patent Application Publication No. 2004-526700, etc.). Specifically, there are a one-step method of reacting iridium trichloride or iridium trisacetylacetonate with a 2-phenylpyrimidine-based ligand, a two-step method of first synthesizing a chlorine-bridged dimer by reacting iridium trichloride with a 2-phenylpyrimidine-based ligand, and reacting this with the ligand L, etc. For the reactions described above, it is also preferred to perform the reactions under a nitrogen atmosphere or under an argon atmosphere. Moreover, although heating means is not particularly limited, irradiation with microwave is also preferable for smoothly promoting the reactions. There is no particular limitation on the wavelength of the microwave, which is however 2000 to 3000 MHz, and one that is preferred is 2400 to 2500 MHz. Every commercially available reaction apparatus for organic synthesis or the like can be applied as a microwave oscillation apparatus. Moreover, an oil bath, mantle heater, or the like may be used as heating means.

Moreover, for further smoothly promoting the reaction that synthesizes the iridium complex according to the present invention, it is desirable to use a reaction solvent. Although there is no particular limitation as such a solvent, an alcoholic solvent, protic solvent, aprotic solvent, nitrile-based solvent, or the like is preferably used. Although the reaction temperature, the reaction pressure and the reaction time differ depending on the raw material used, the solvent, etc., usually the reaction temperature is 40 to 250° C., preferably 50 to 230° C., more preferably 60 to 220° C. and the reaction pressure is 1 to 30 atm, preferably 1 to 5 atm.

The iridium complex according to the present invention can be treated according to the usual posttreatment of synthesis reaction and then used, if necessary after being purified, or without being purified. As a method of the posttreatment, for example, extraction, cooling, crystallization by adding water or an organic solvent, an operation of distilling off the solvent from the reaction mixture, and so on can be performed alone or in combination. As a method of the purification, recrystallization, distillation, sublimation, column chromatography, and so on can be performed alone or in combination.

Although typical examples of the iridium complex represented by formula (1) or (2) according to the present invention will be shown below, the present invention is not limited to these. —$C_3H_7$, —$C_4H_9$, —$C_5H_{11}$, —$C_7H_{15}$, —$C_8H_{17}$, —$C_9H_{19}$, —$C_{10}H_{21}$, —$C_{12}H_{25}$, —$C_{15}H_{31}$, and —$C_{18}H_{37}$ described in Table 3 to Table 12 each represent a linear alkyl group, and —$OC_6H_{13}$ and —$OC_7H_{15}$ each represent a linear alkoxy group.

TABLE 3

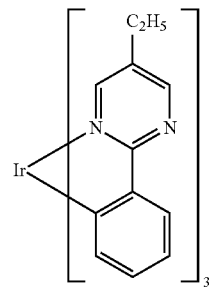
(1)

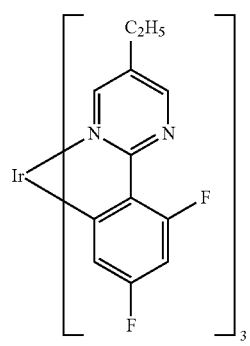
(2)

TABLE 3-continued

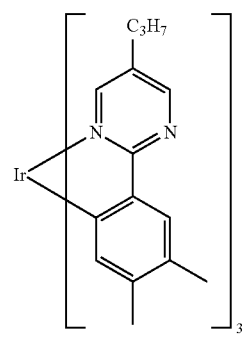
(3)

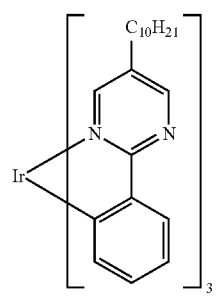
(4)

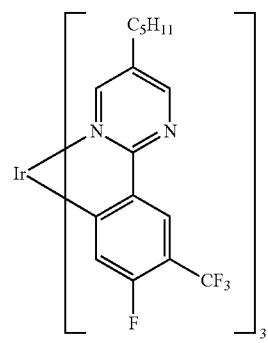
(5)

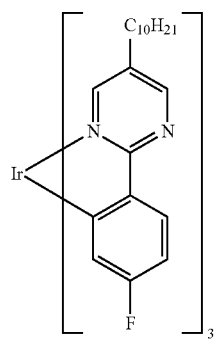
(6)

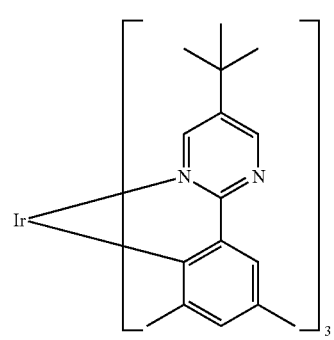
(7)

TABLE 3-continued
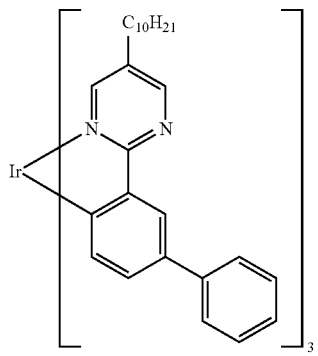 (8)
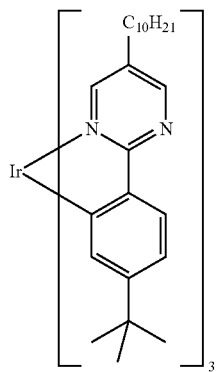 (9)
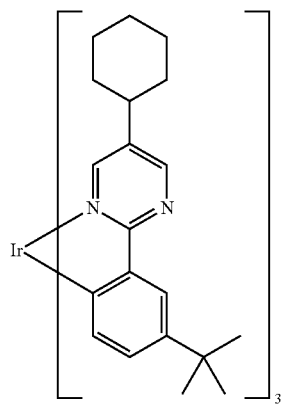 (10)
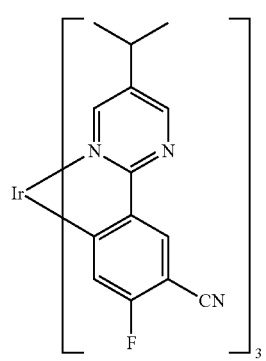 (11)
TABLE 3-continued
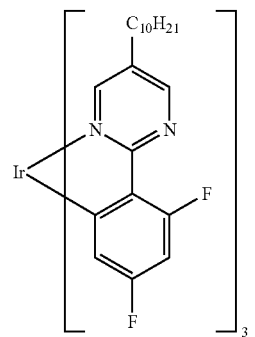 (12)
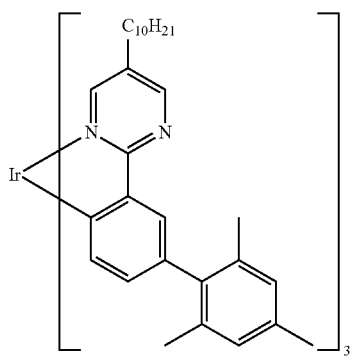 (13)
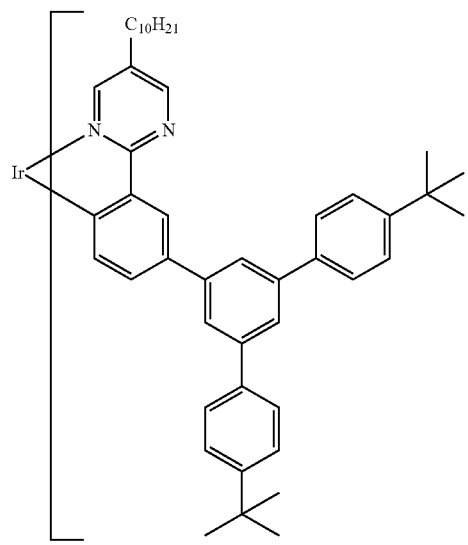 (14)
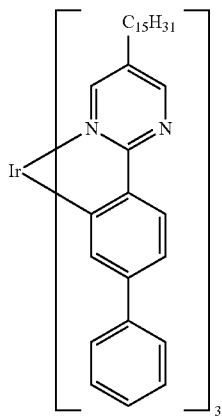 (15)

TABLE 3-continued
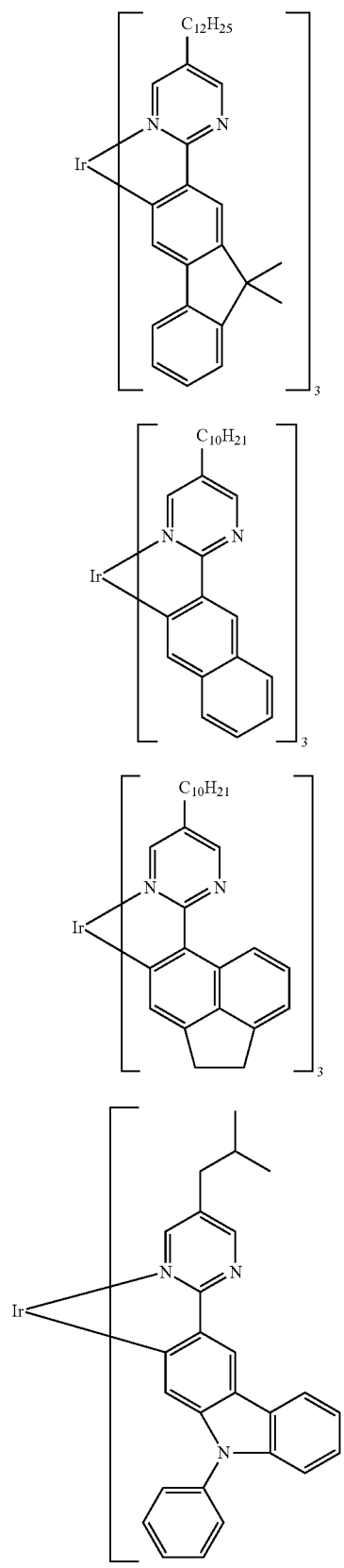
TABLE 3-continued
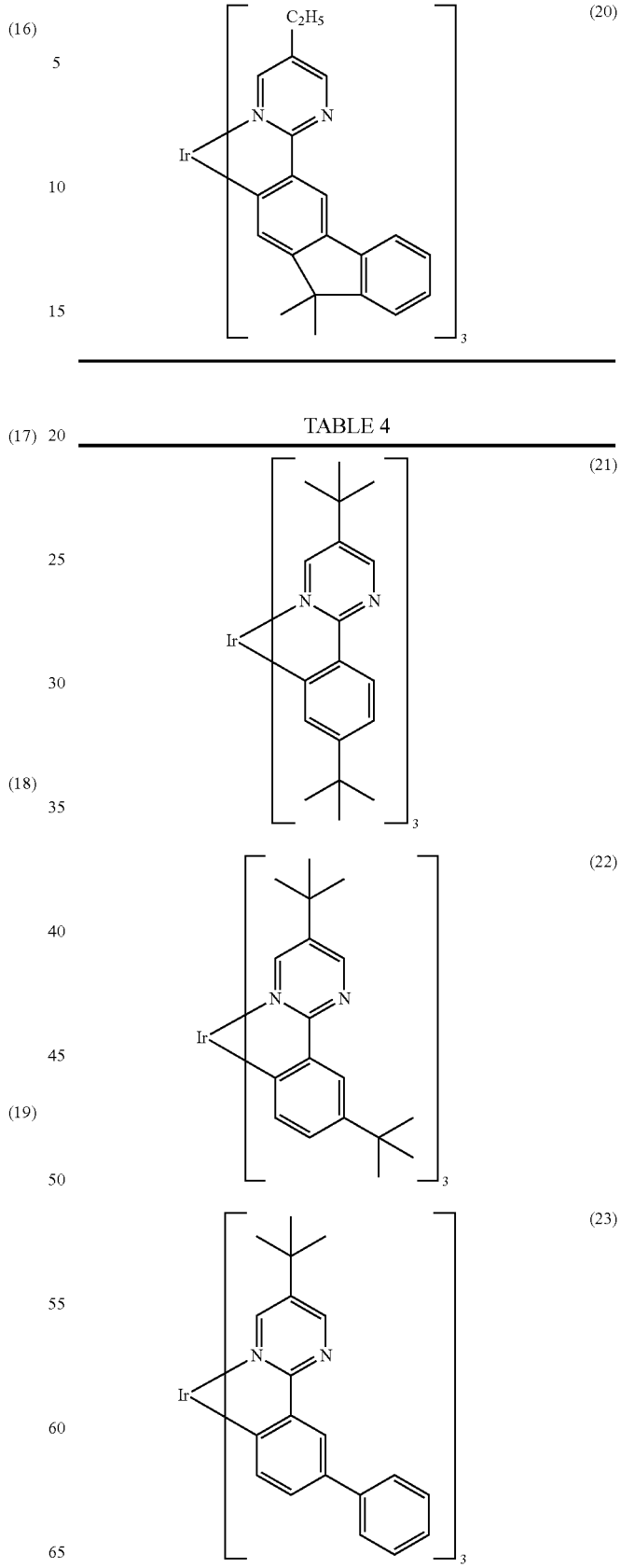
TABLE 4
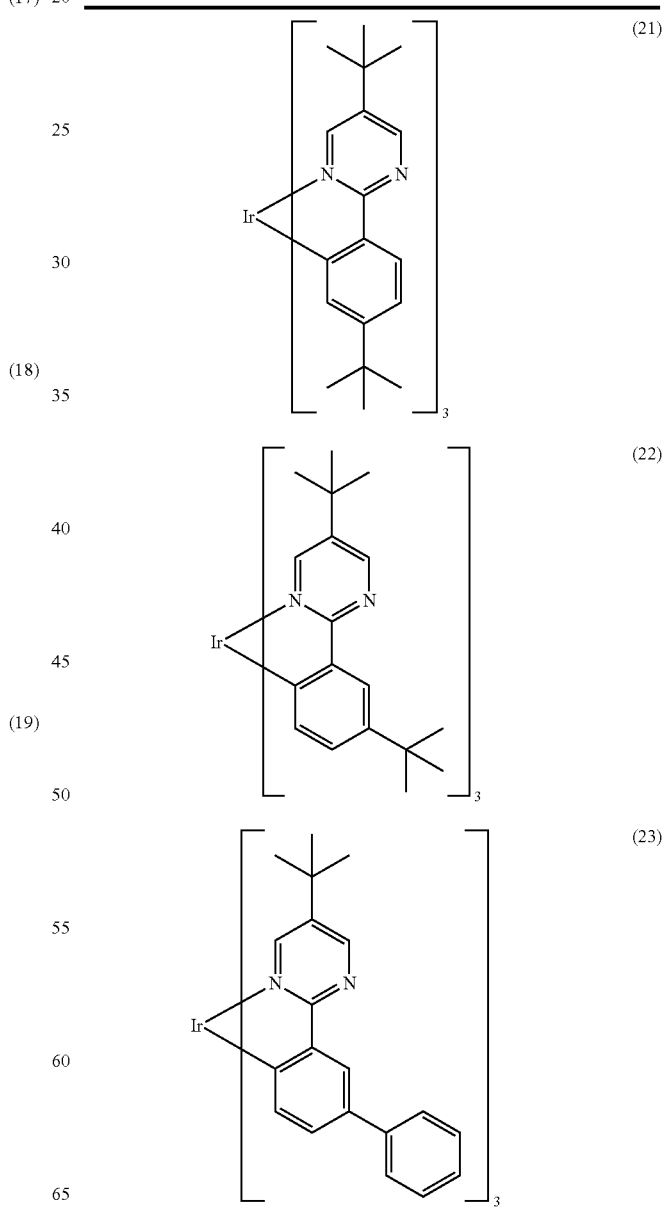

TABLE 4-continued
(24) 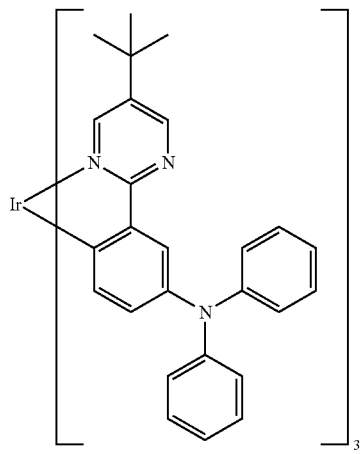
(25) 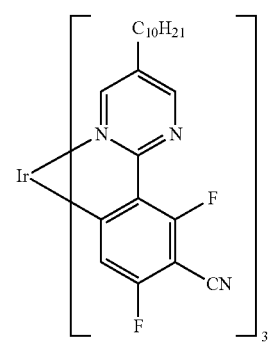
(26) 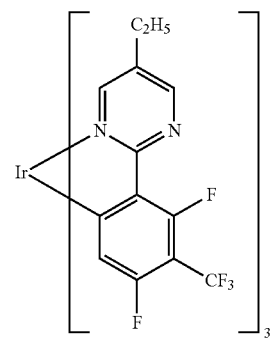
(27) 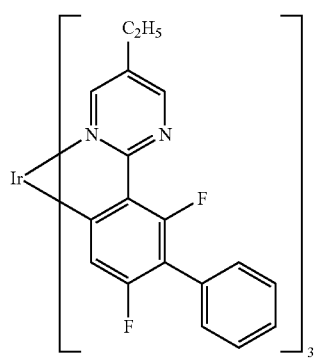
TABLE 4-continued
(28) 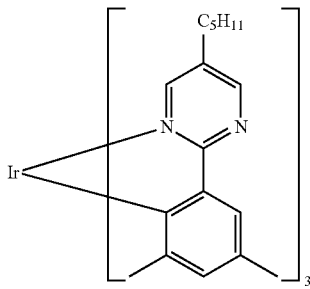
(29) 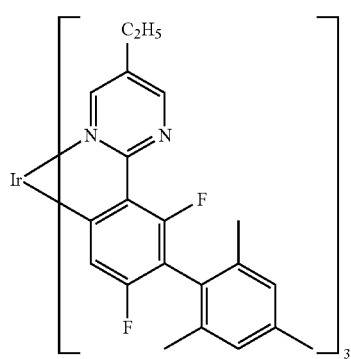
(30) 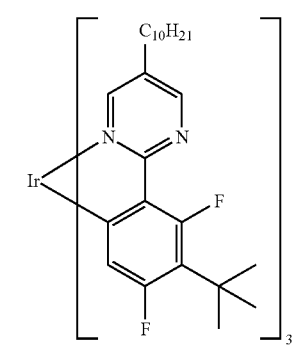
(31) 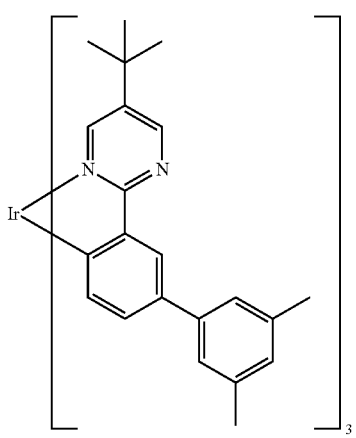

TABLE 4-continued
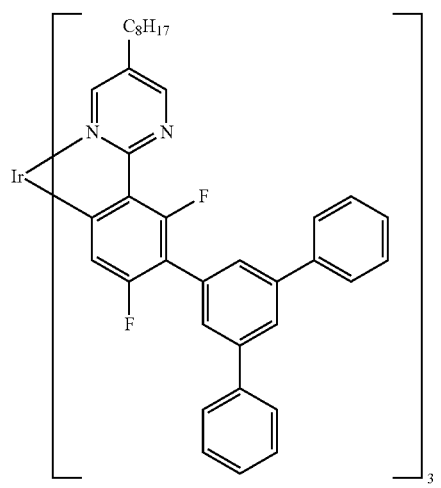
(32)
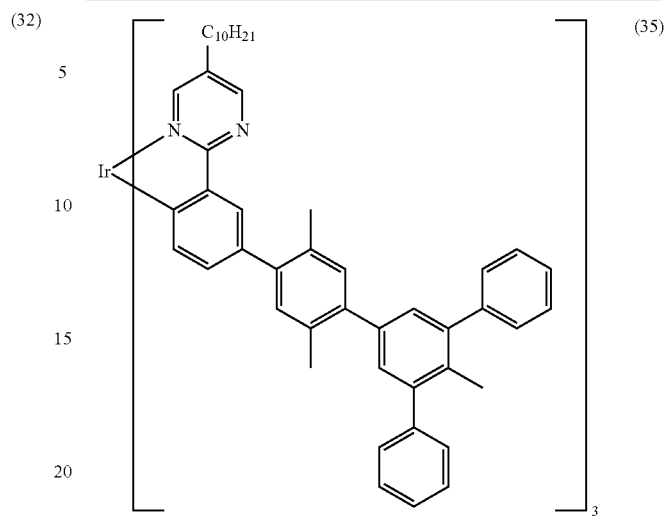
(35)
TABLE 5
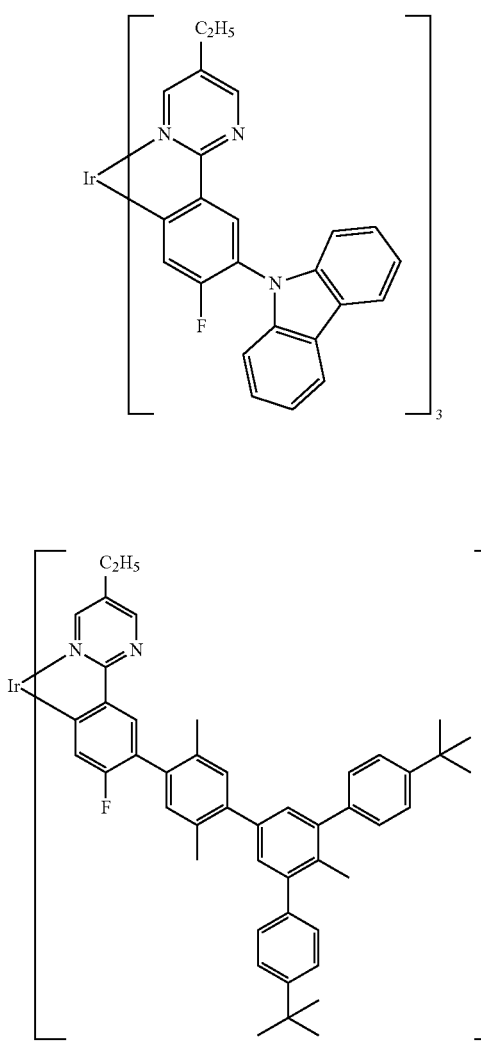
(33)
(34)
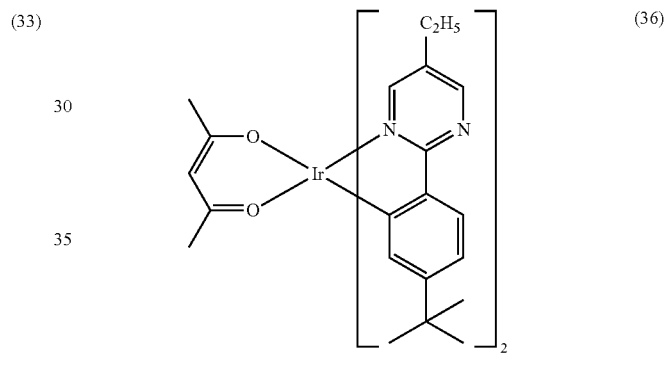
(36)
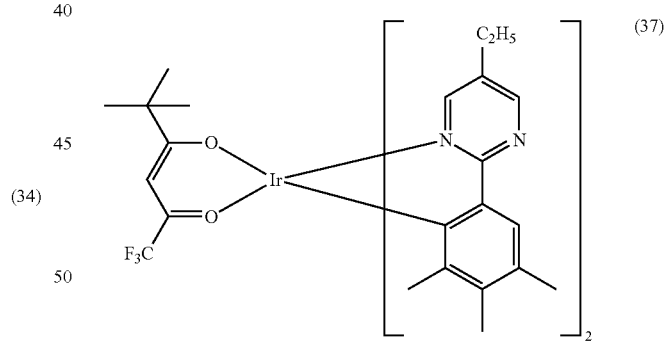
(37)
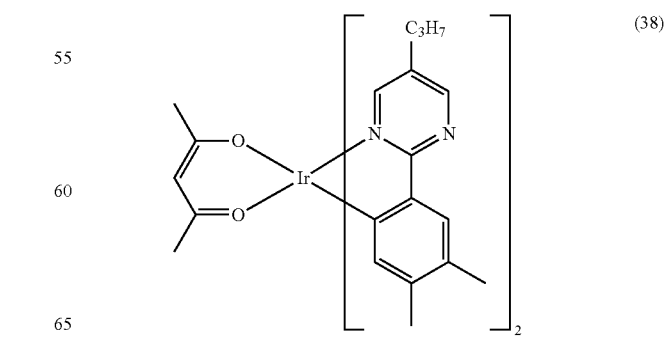
(38)

TABLE 5-continued
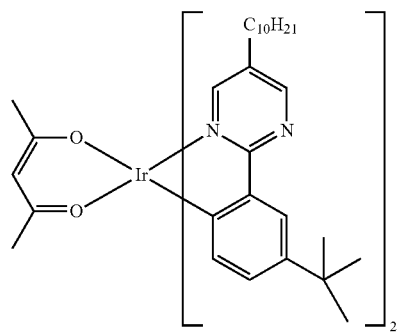 (39)
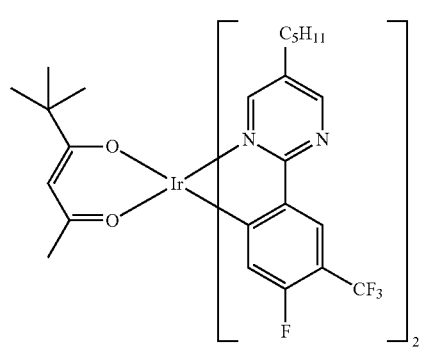 (40)
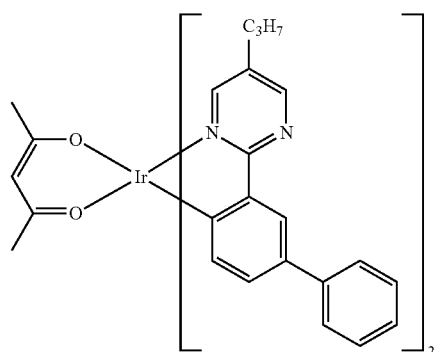 (41)
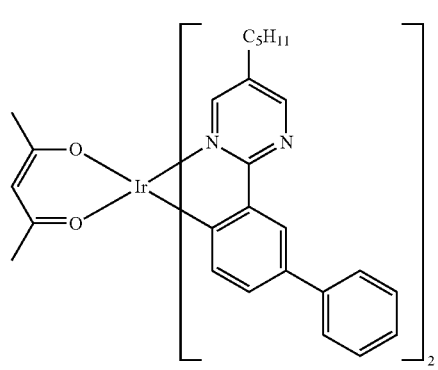 (42)
TABLE 5-continued
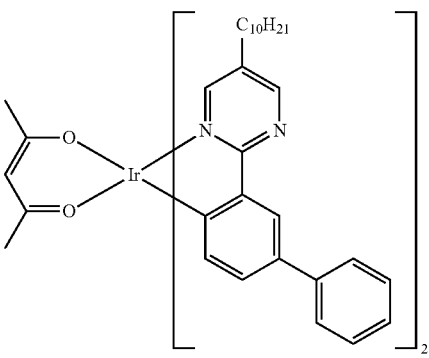 (43)
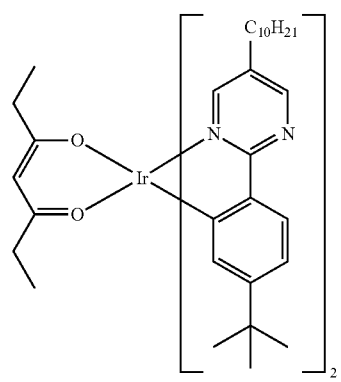 (44)
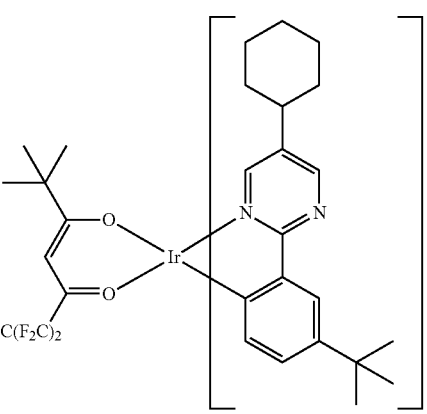 (45)
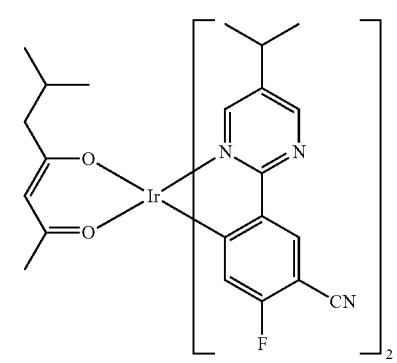 (46)

TABLE 5-continued
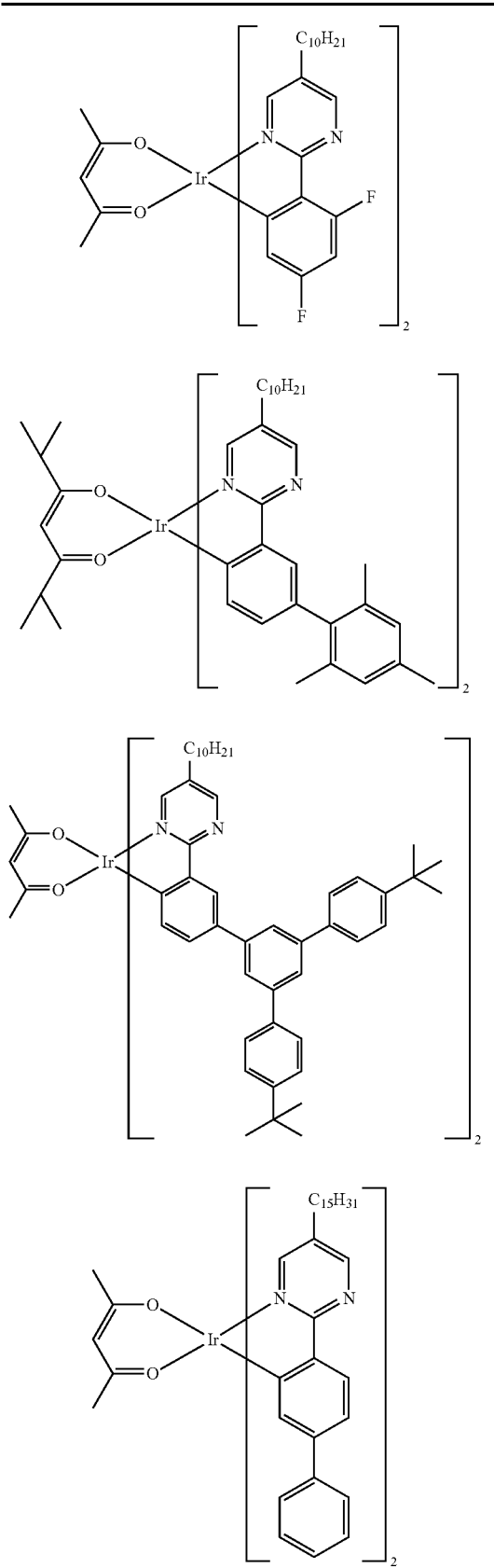
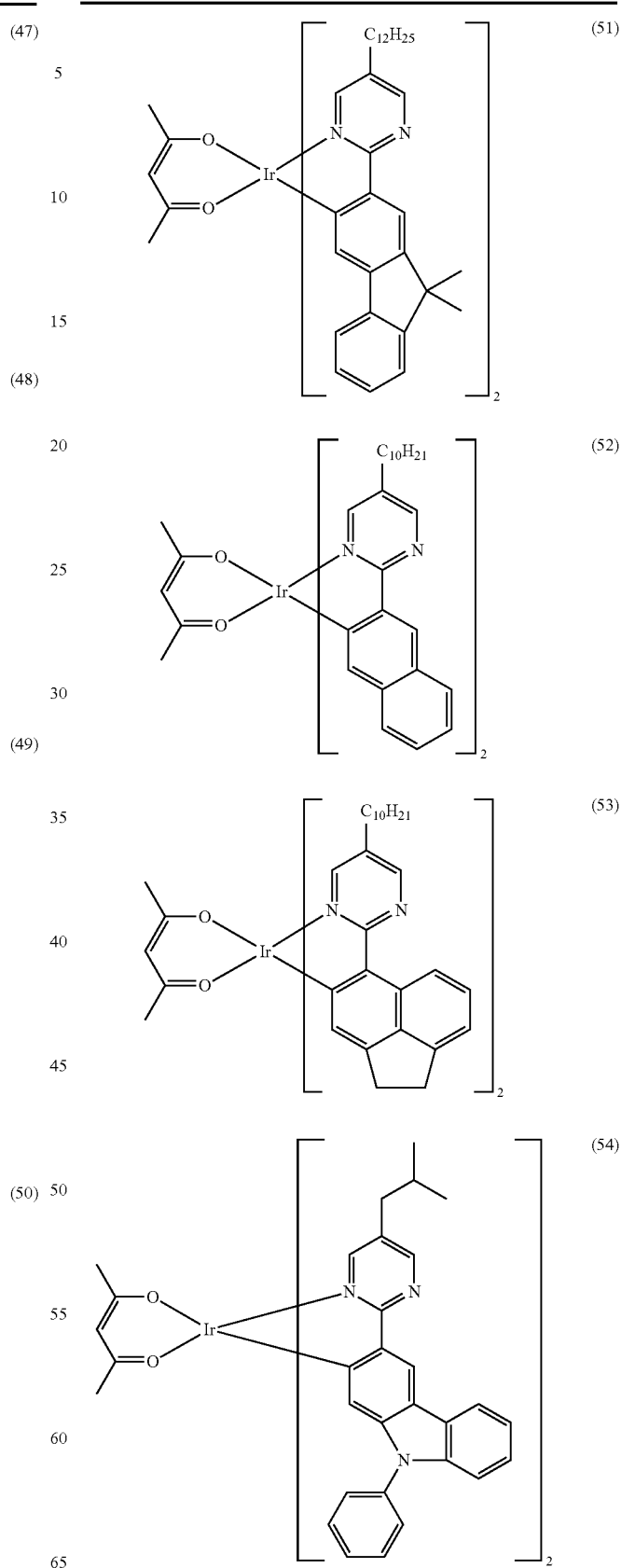

TABLE 5-continued
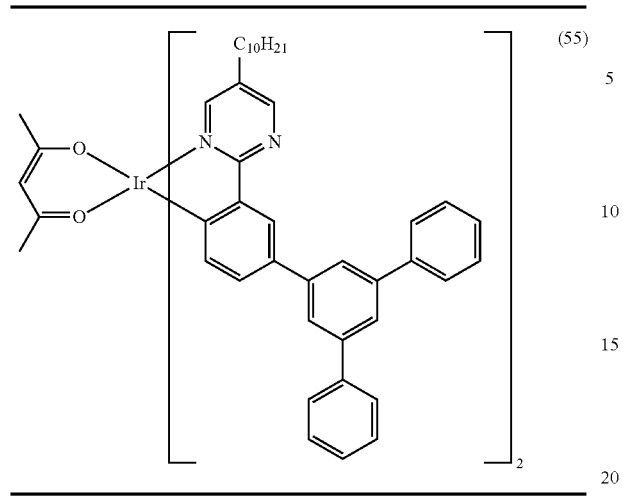
TABLE 6
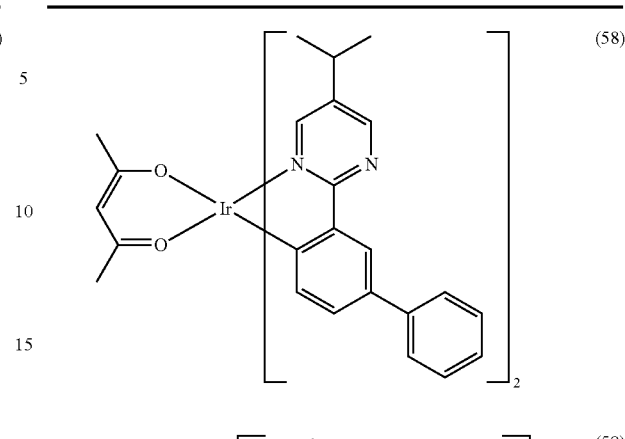
TABLE 6-continued
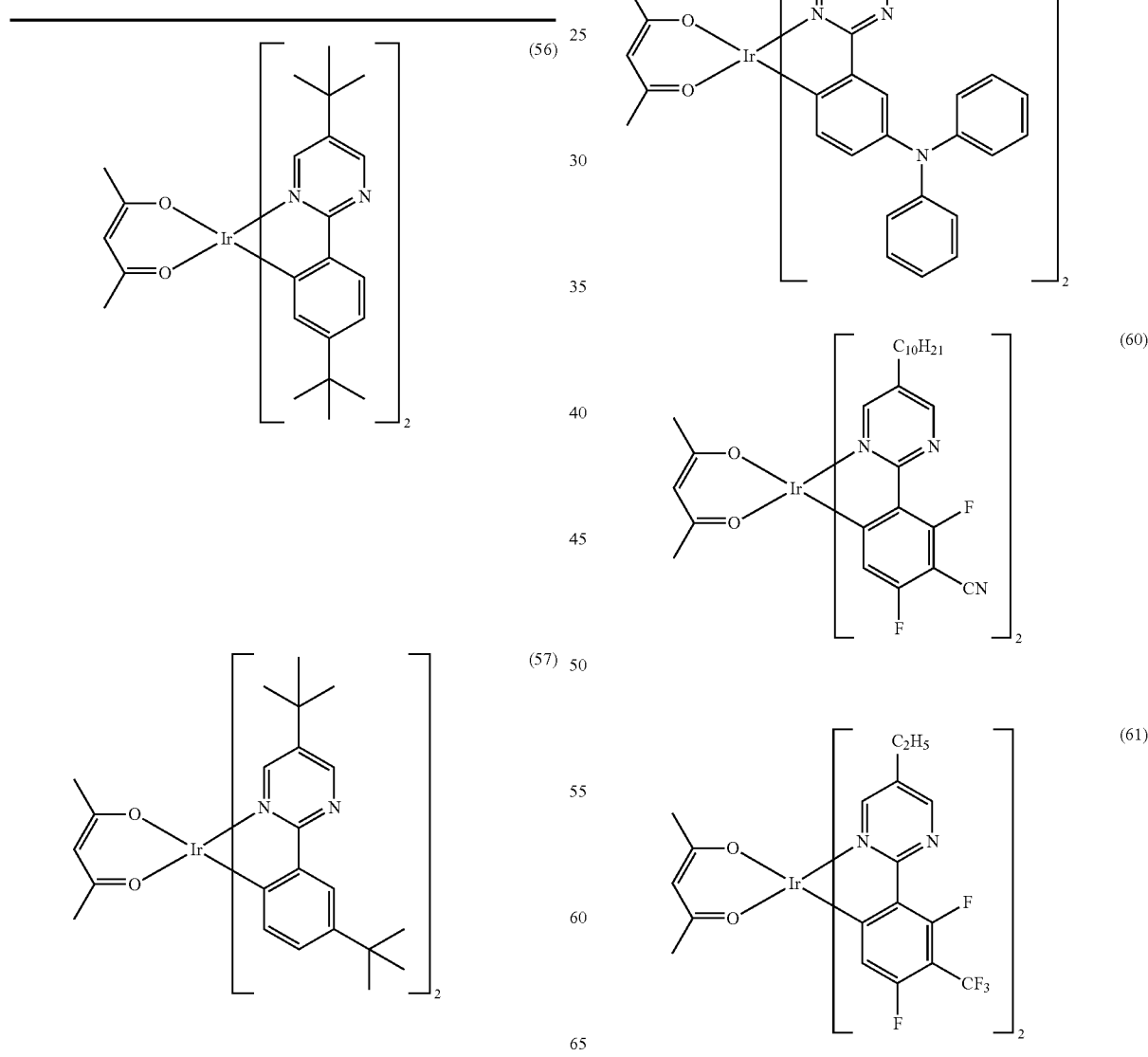

TABLE 6-continued
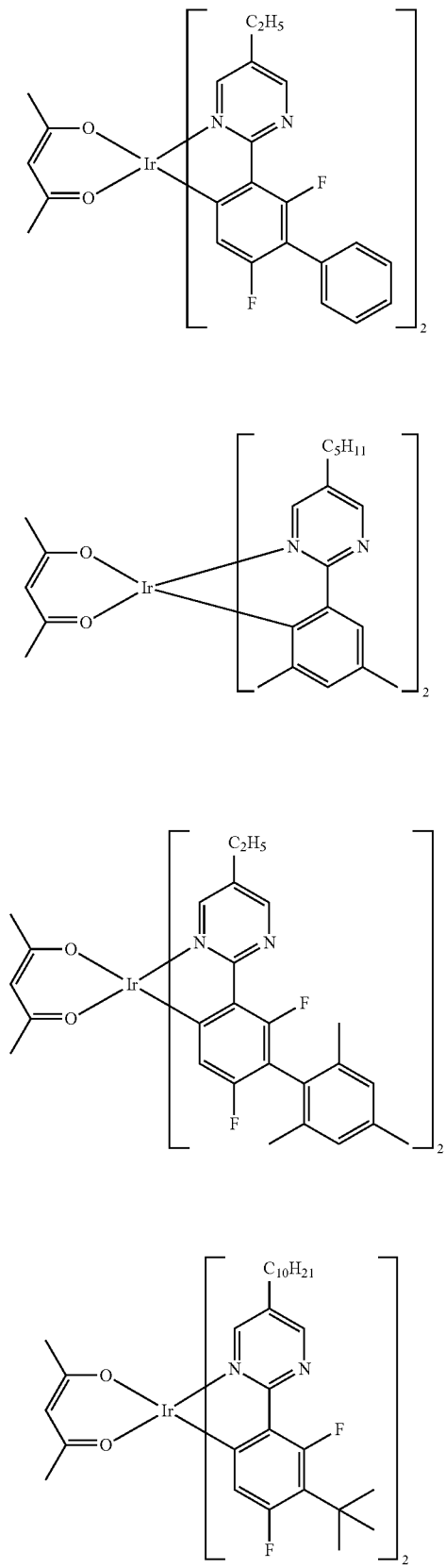
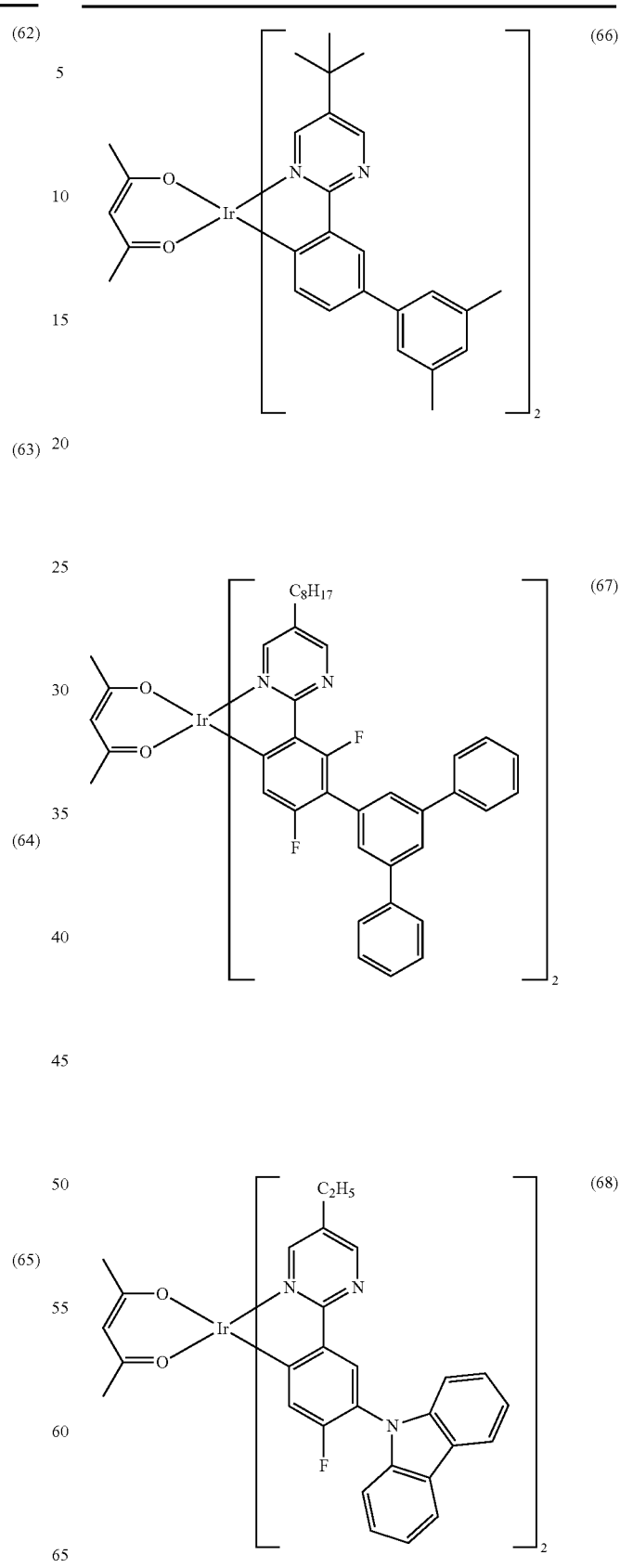

TABLE 6-continued
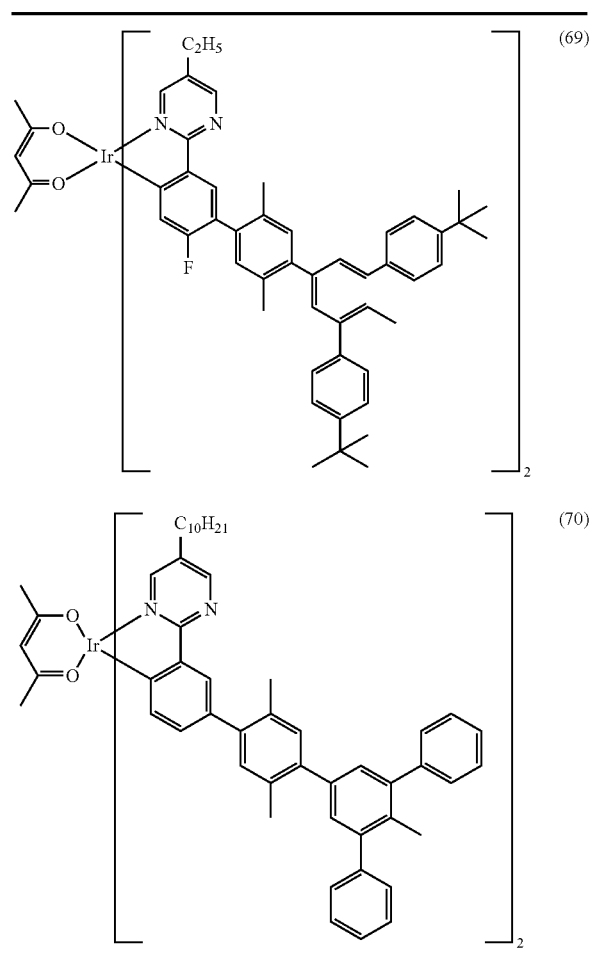
TABLE 7
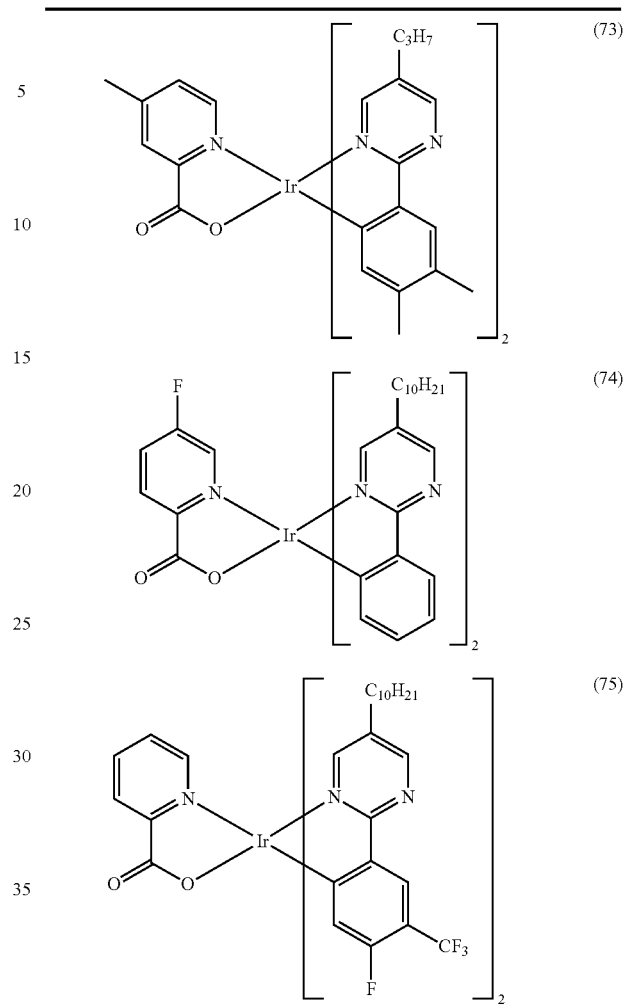
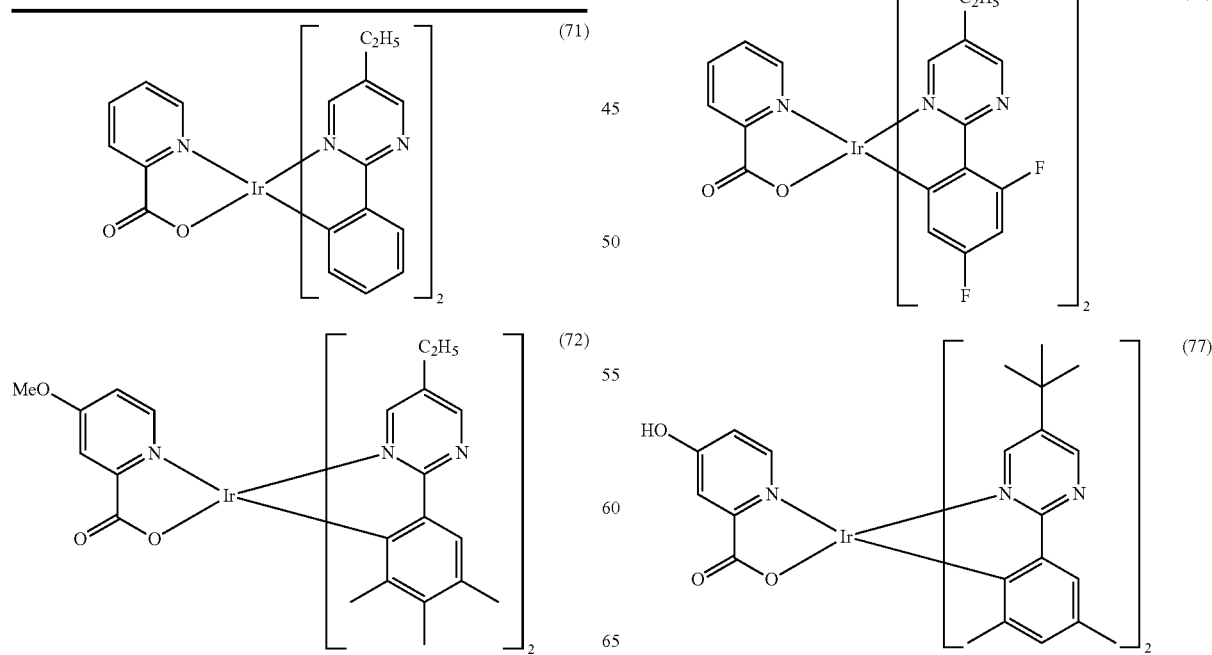

TABLE 7-continued
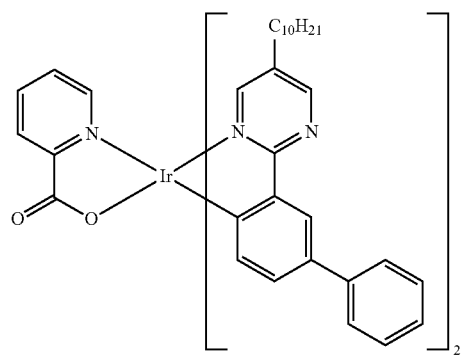
(78)
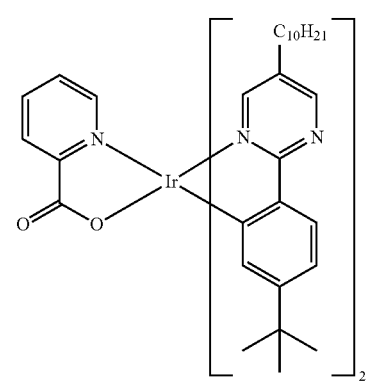
(79)
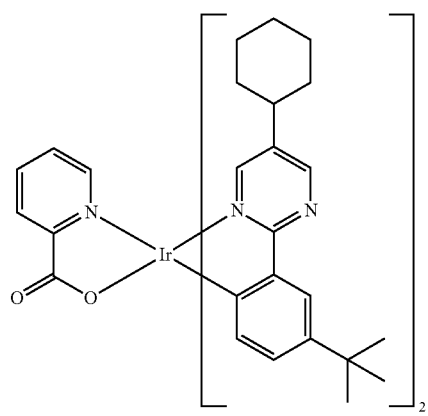
(80)
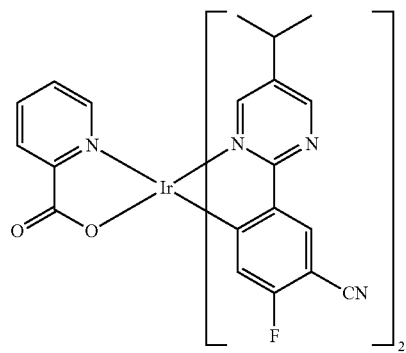
(81)
TABLE 7-continued
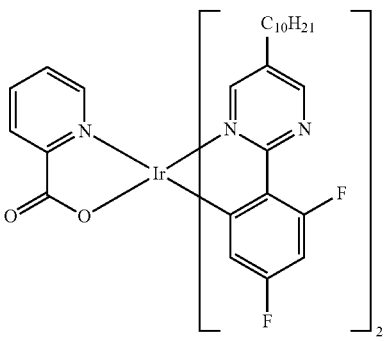
(82)
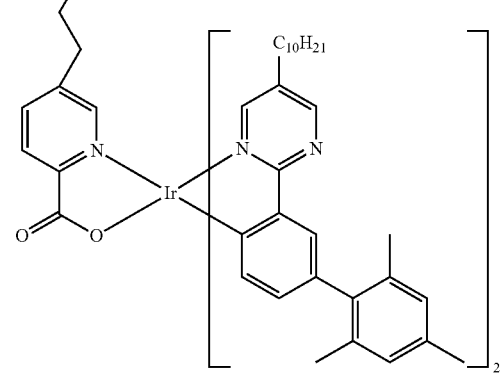
(83)
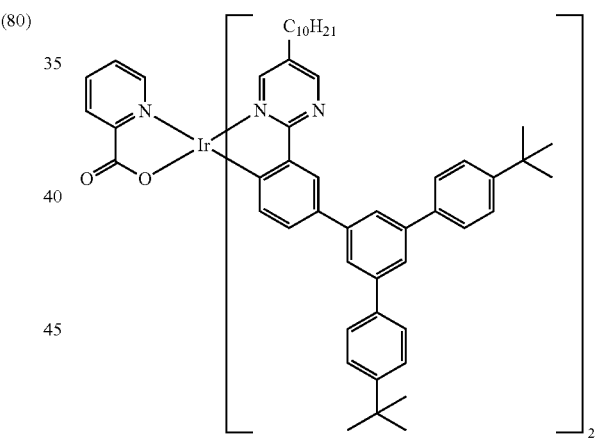
(84)
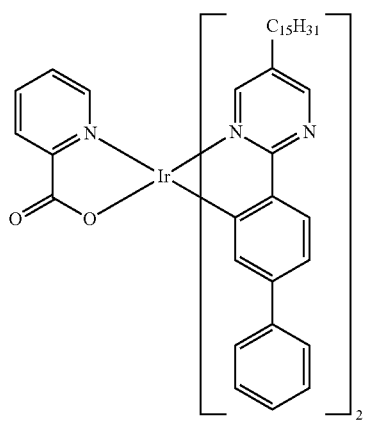
(85)

TABLE 7-continued
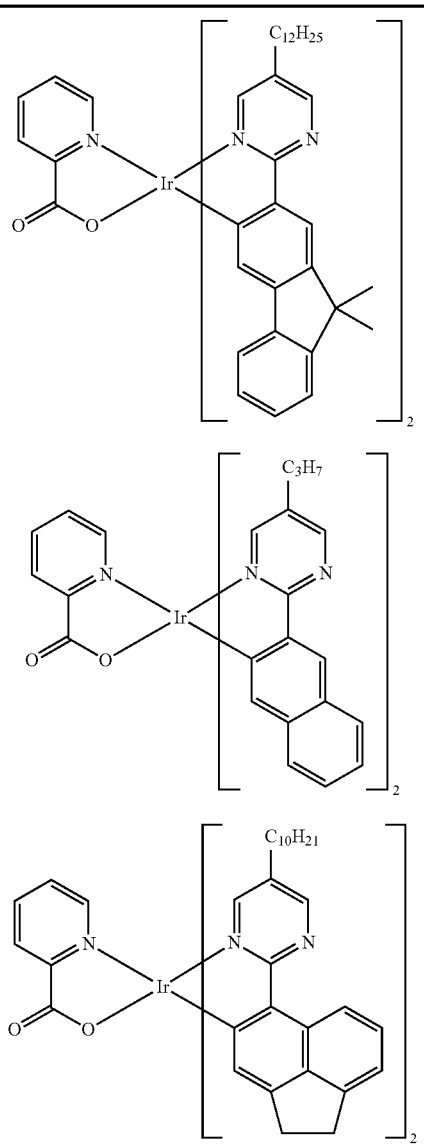
TABLE 7-continued
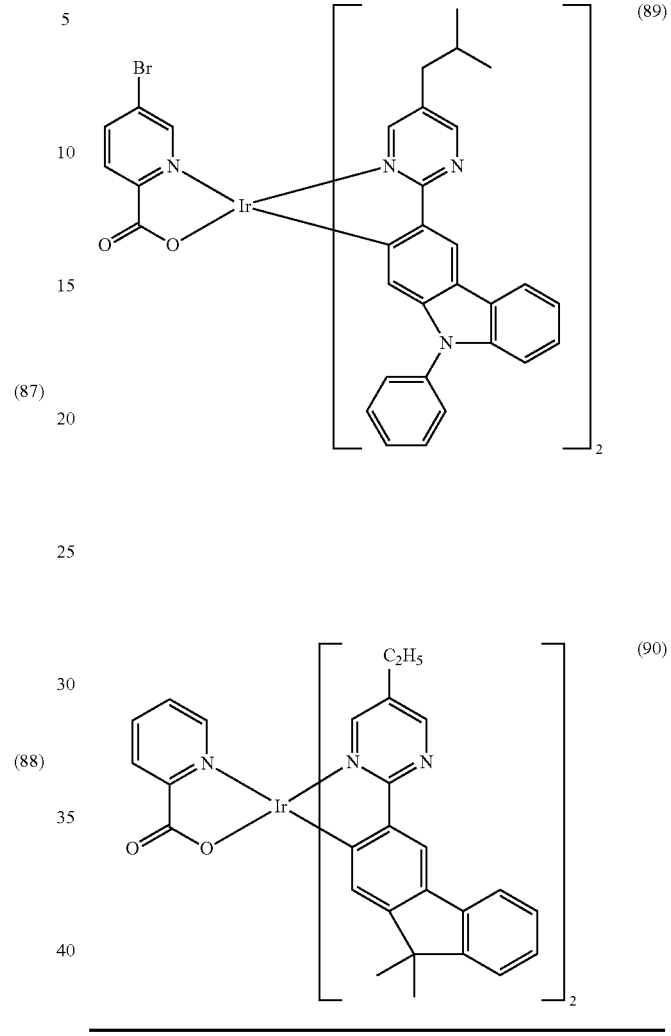
TABLE 8
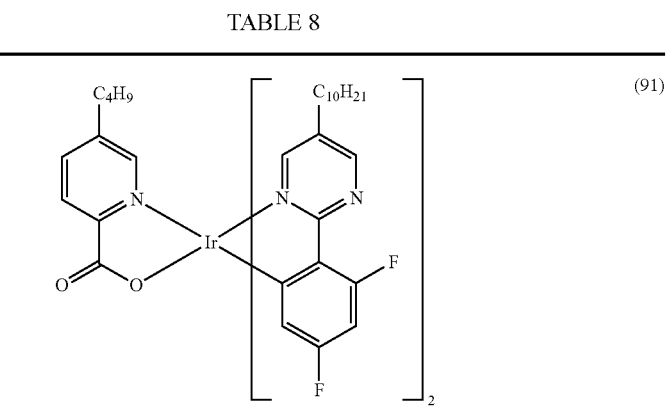

TABLE 8-continued
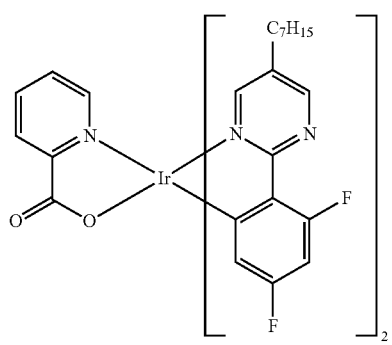
(92)
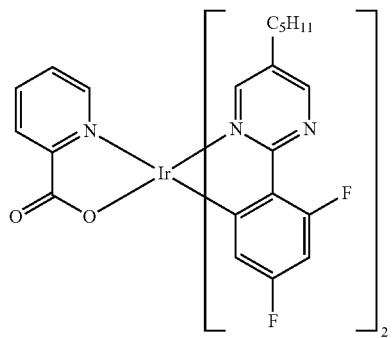
(93)
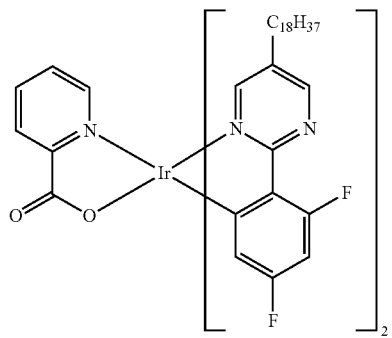
(94)
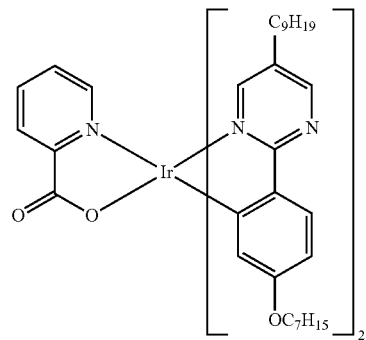
(95)

TABLE 8-continued
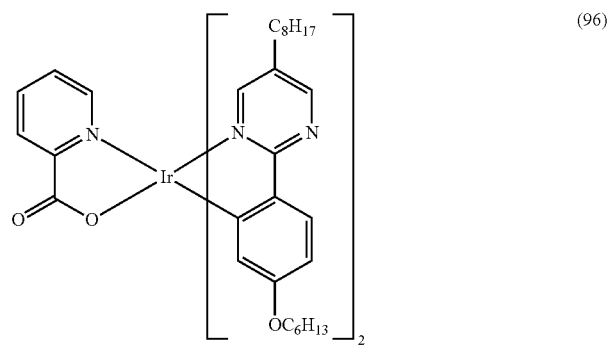
(96)
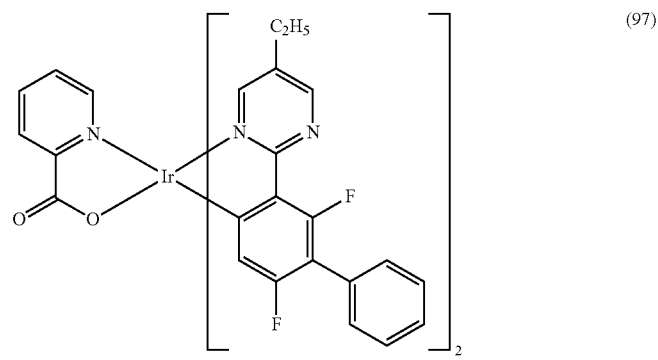
(97)
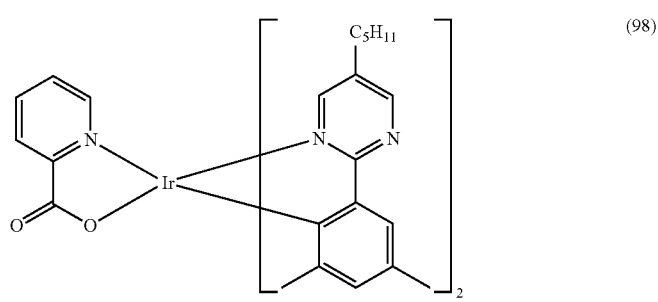
(98)
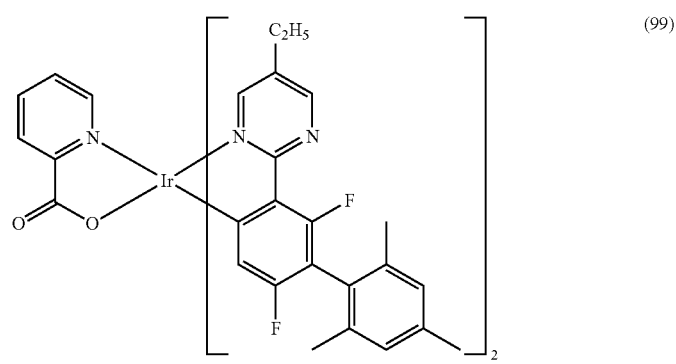
(99)

TABLE 8-continued
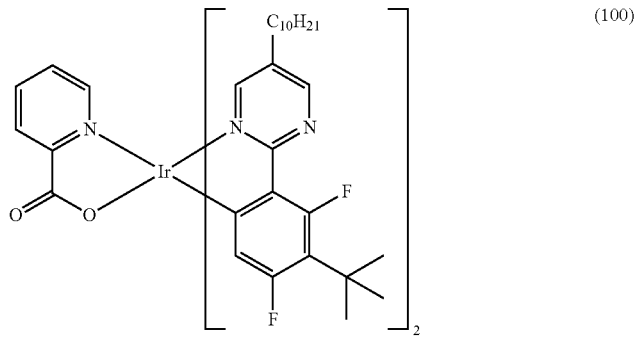
(100)
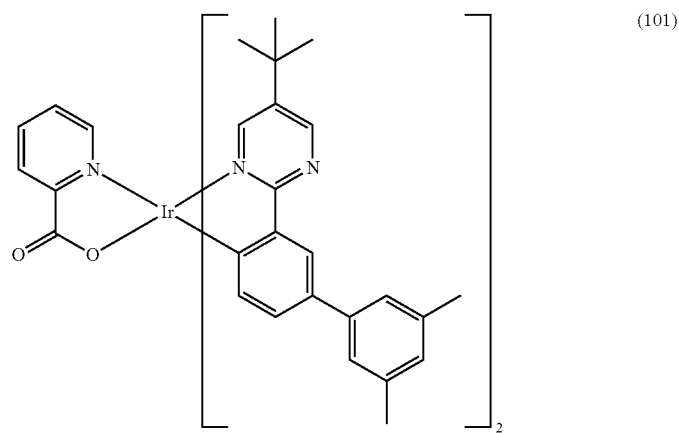
(101)
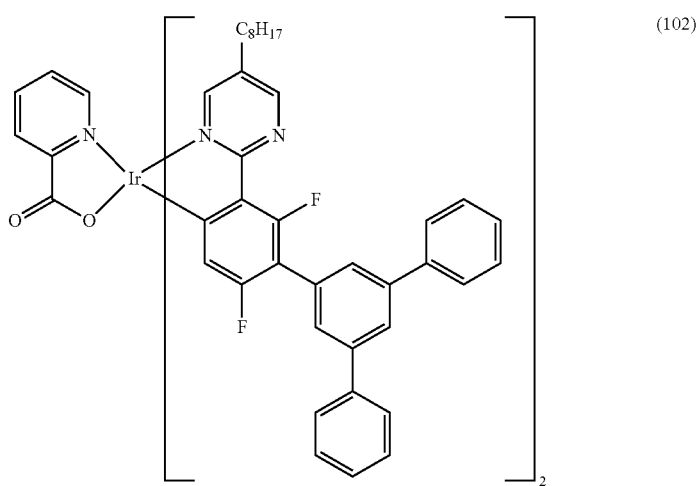
(102)

TABLE 8-continued
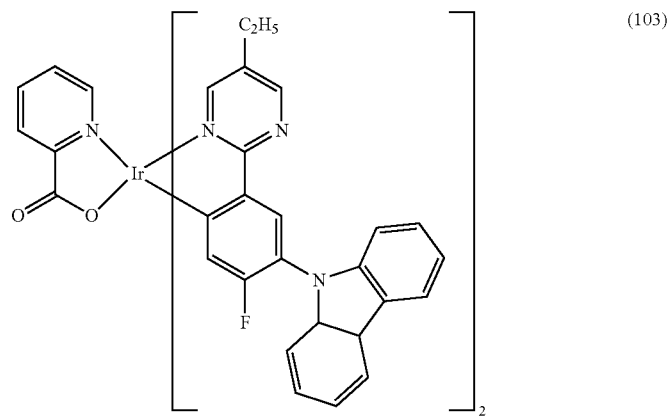
(103)
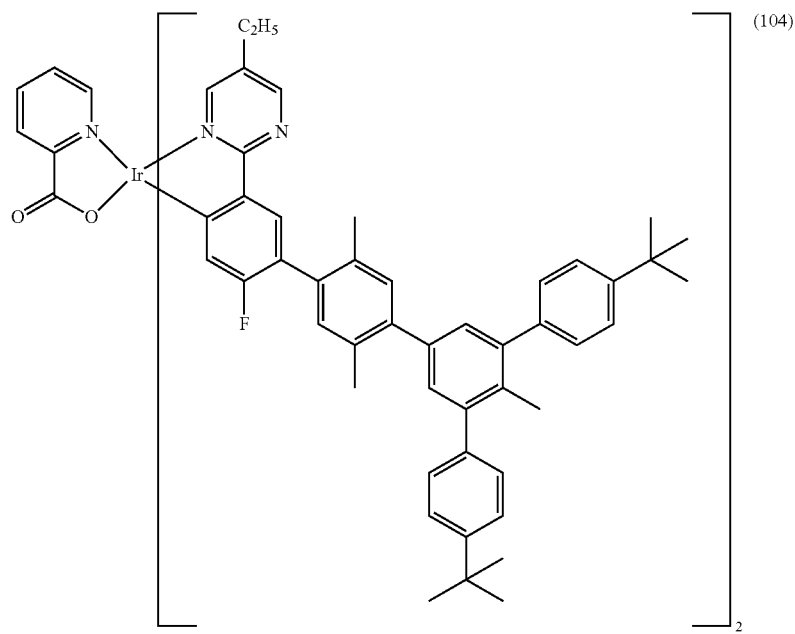
(104)
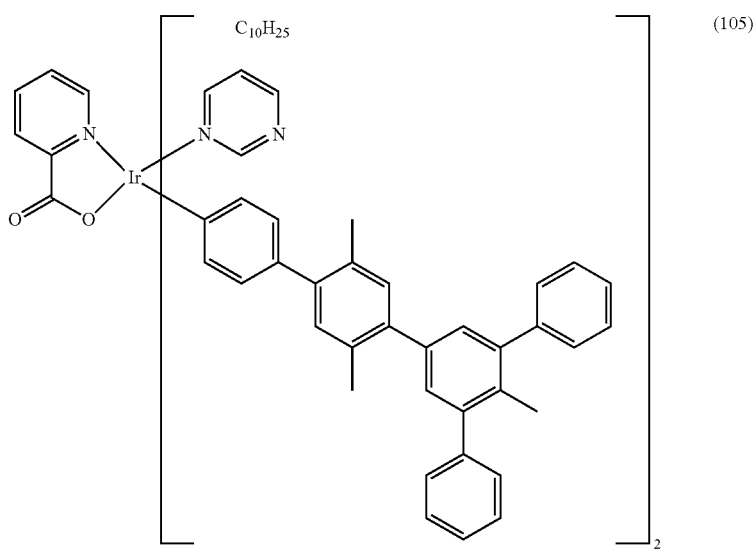
(105)

TABLE 9
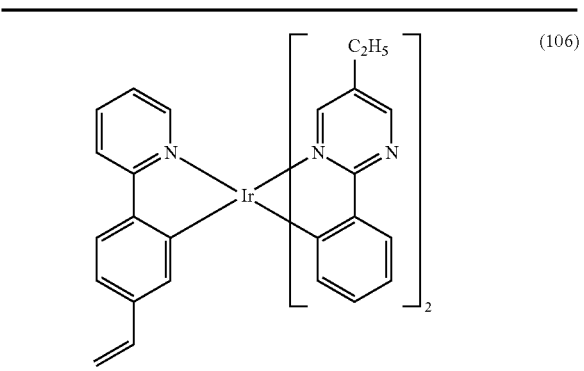
(106)
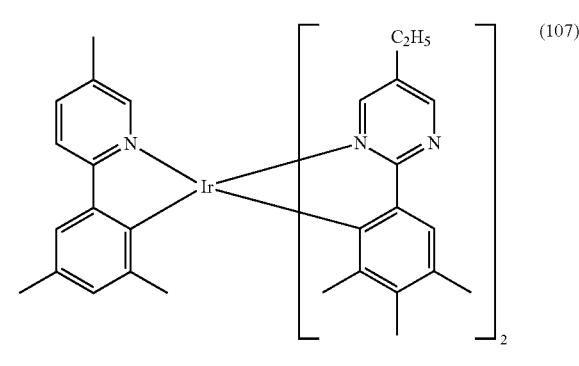
(107)
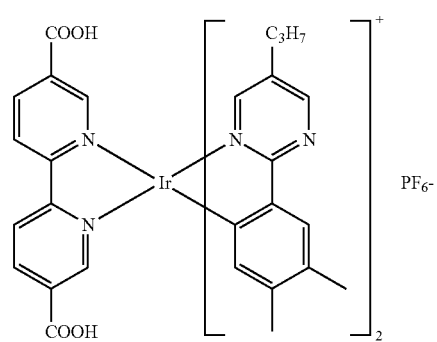
(108)
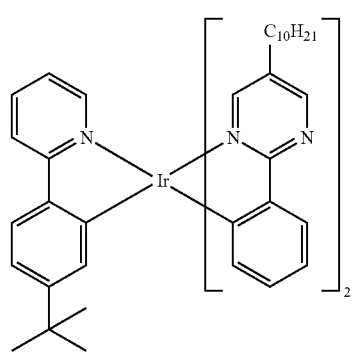
(109)
TABLE 9-continued
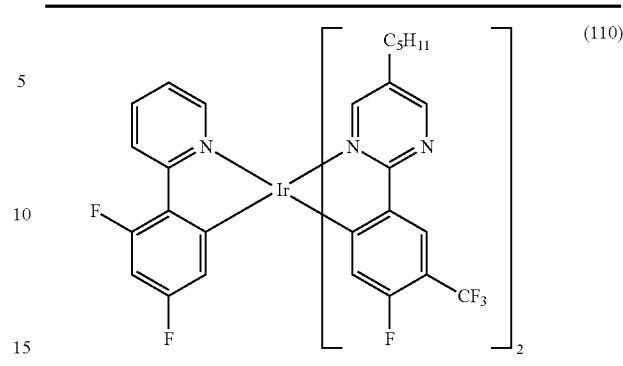
(110)
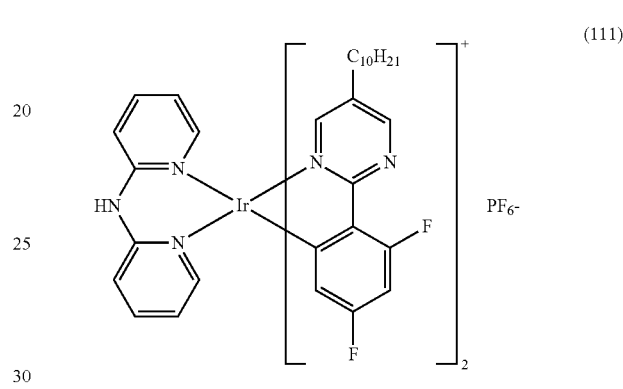
(111)
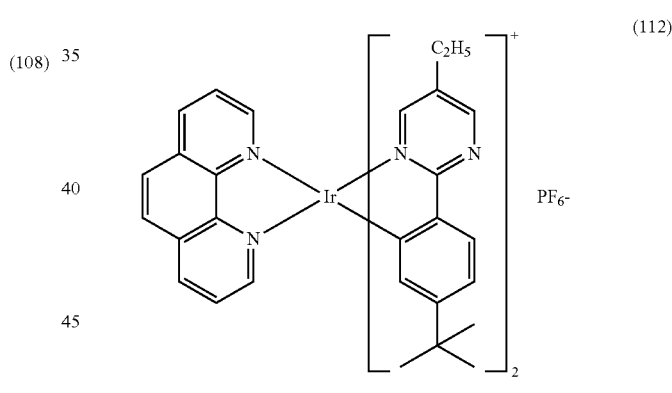
(112)
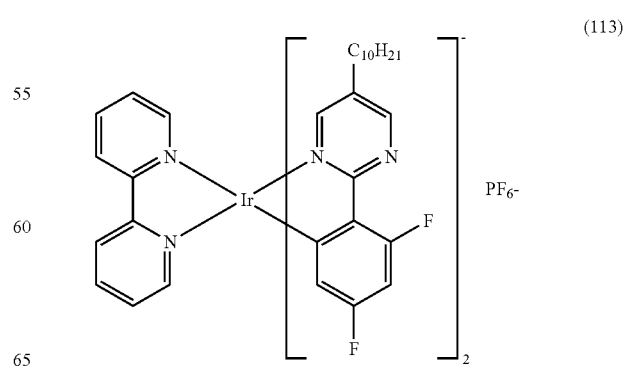
(113)

TABLE 9-continued
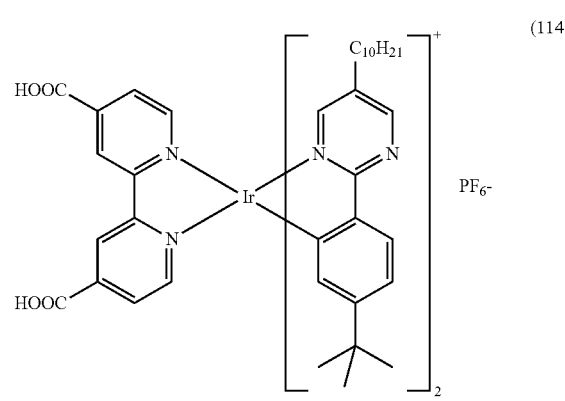
(114)
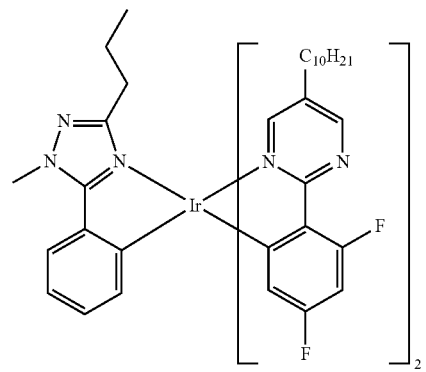
(115)
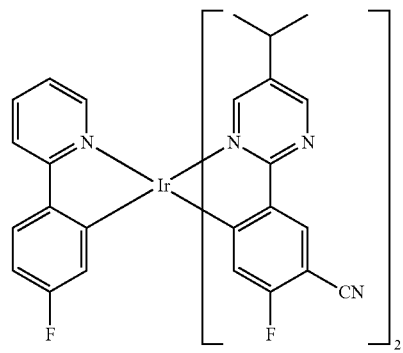
(116)
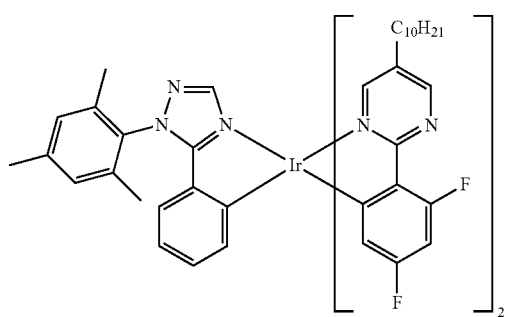
(117)
TABLE 9-continued
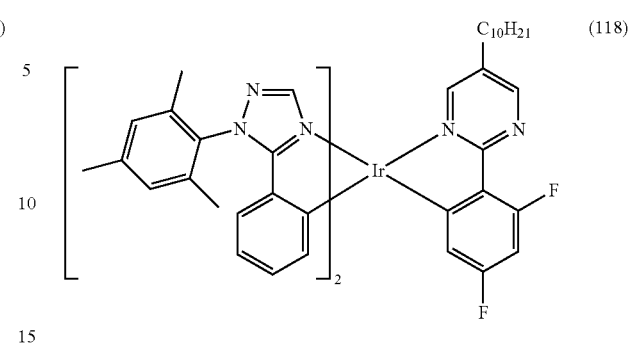
(118)
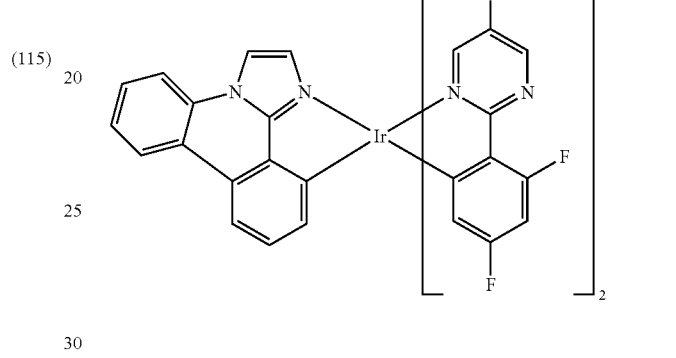
(119)
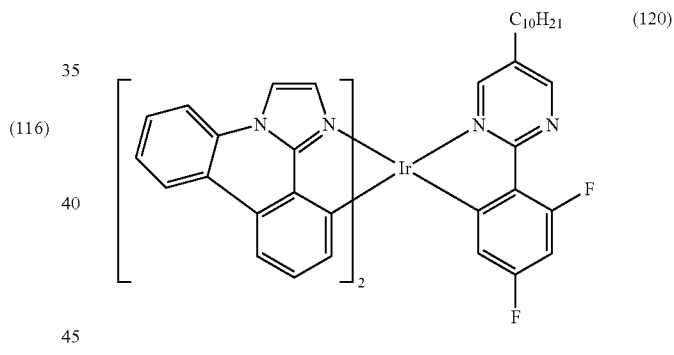
(120)
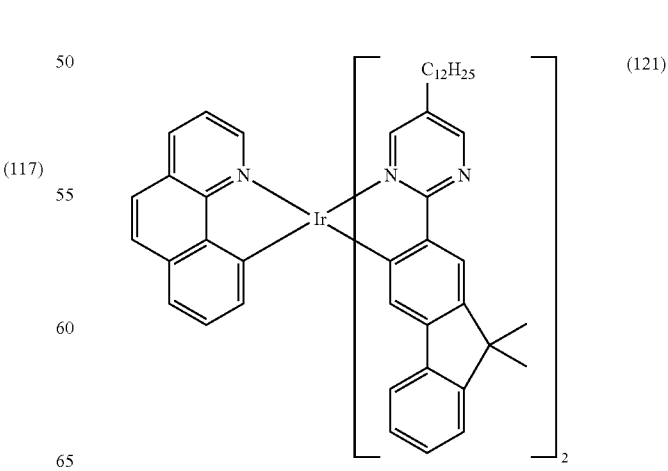
(121)

TABLE 9-continued
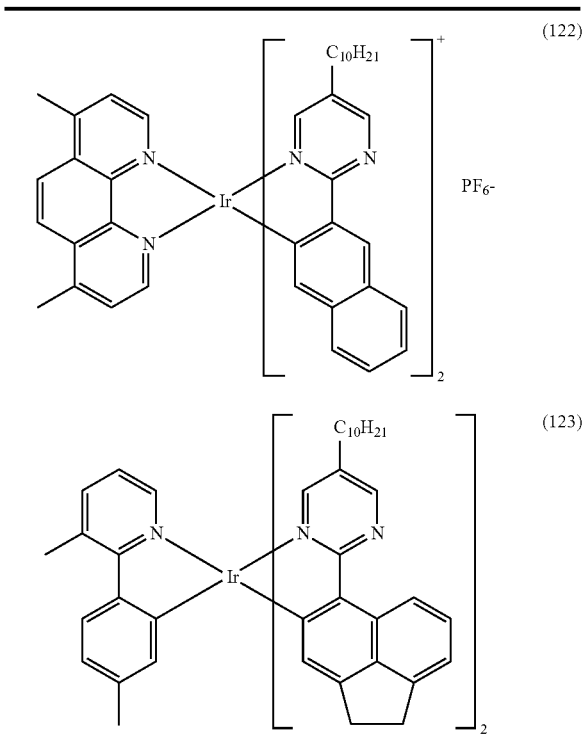
TABLE 9-continued
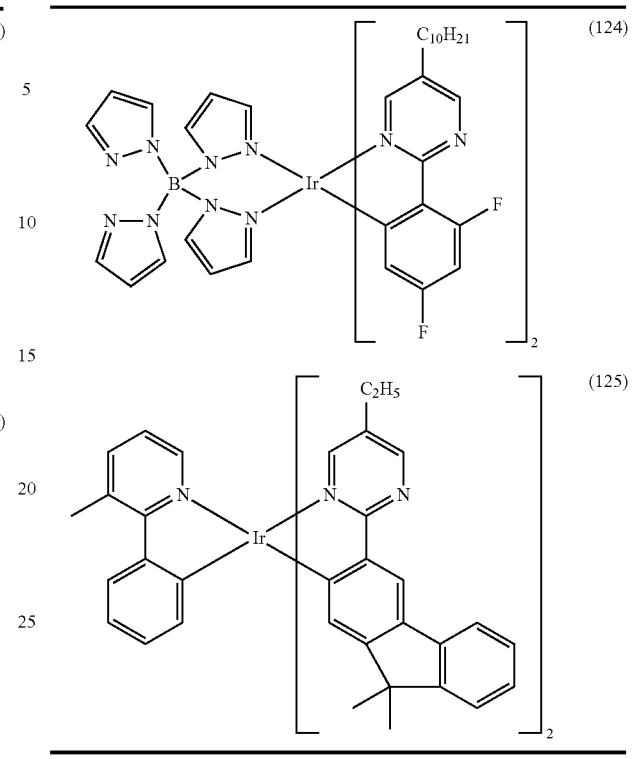
TABLE 10
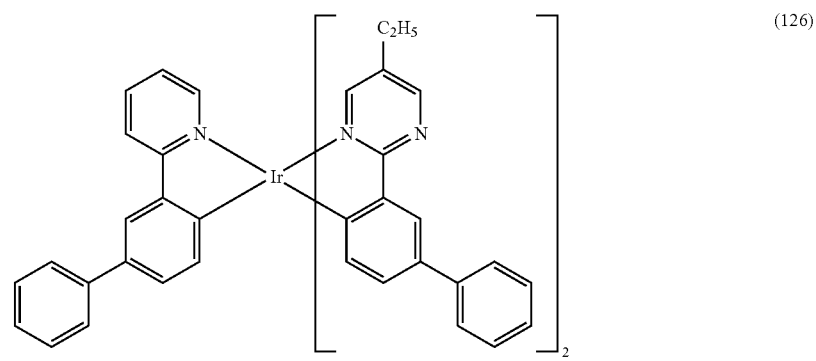
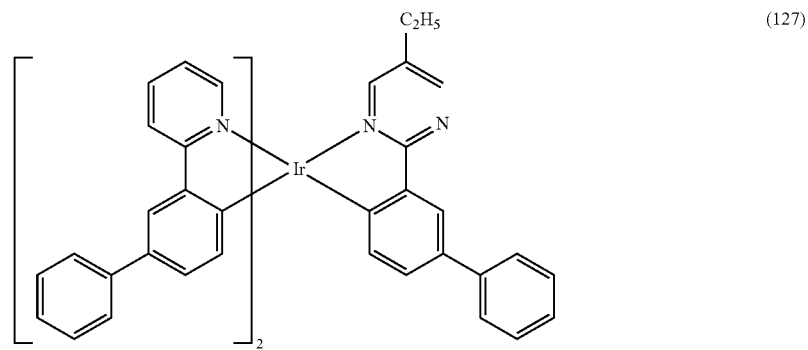

TABLE 10-continued
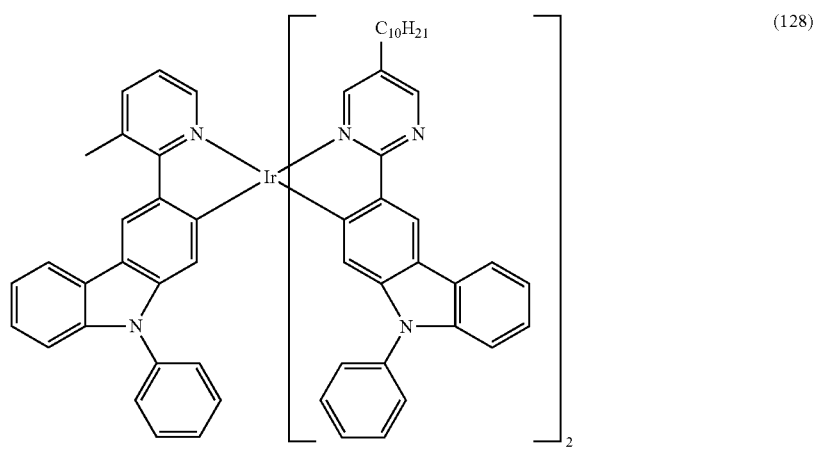
(128)
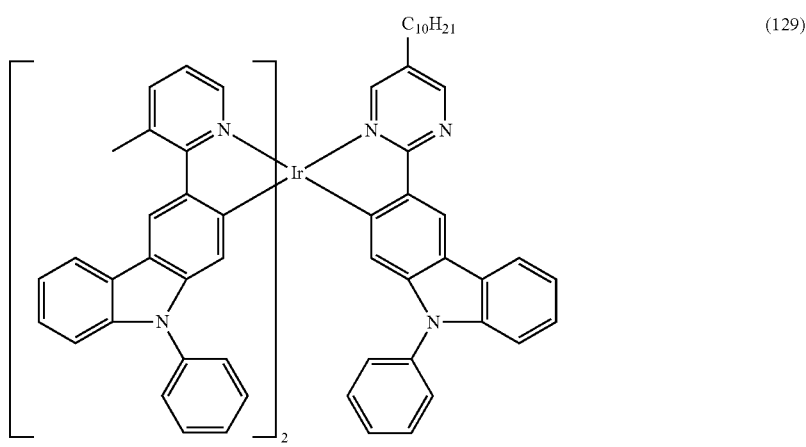
(129)
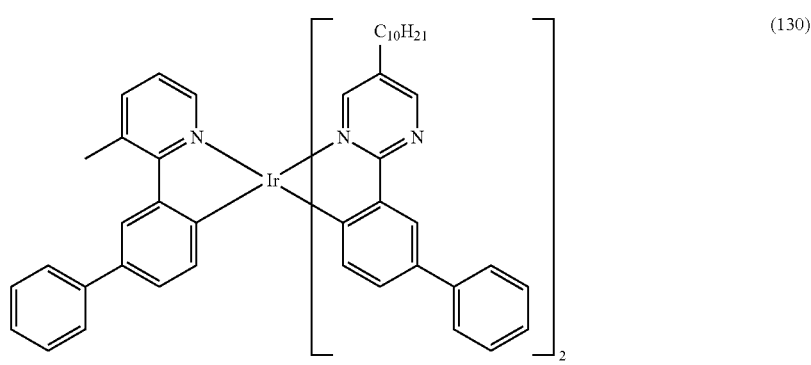
(130)
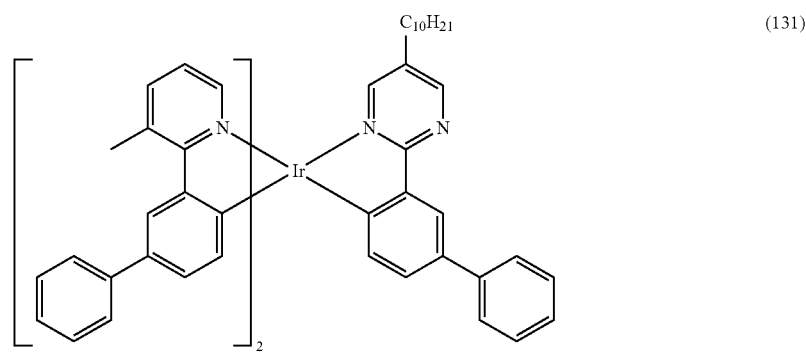
(131)

TABLE 10-continued
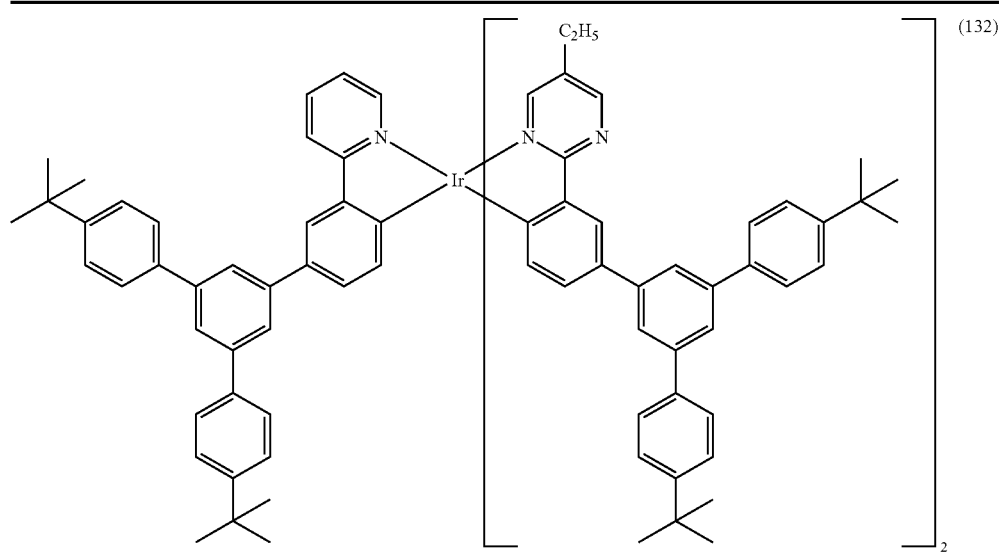
(132)
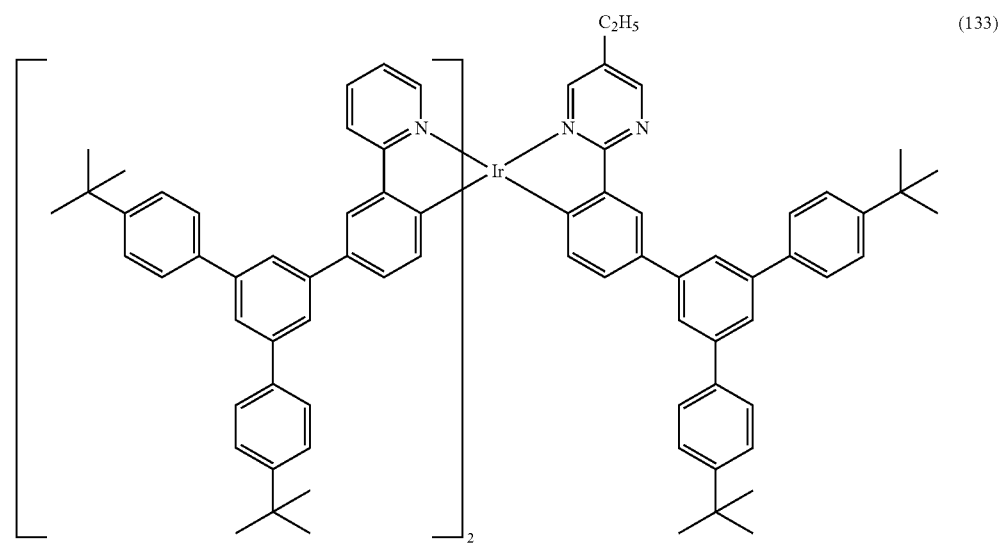
(133)
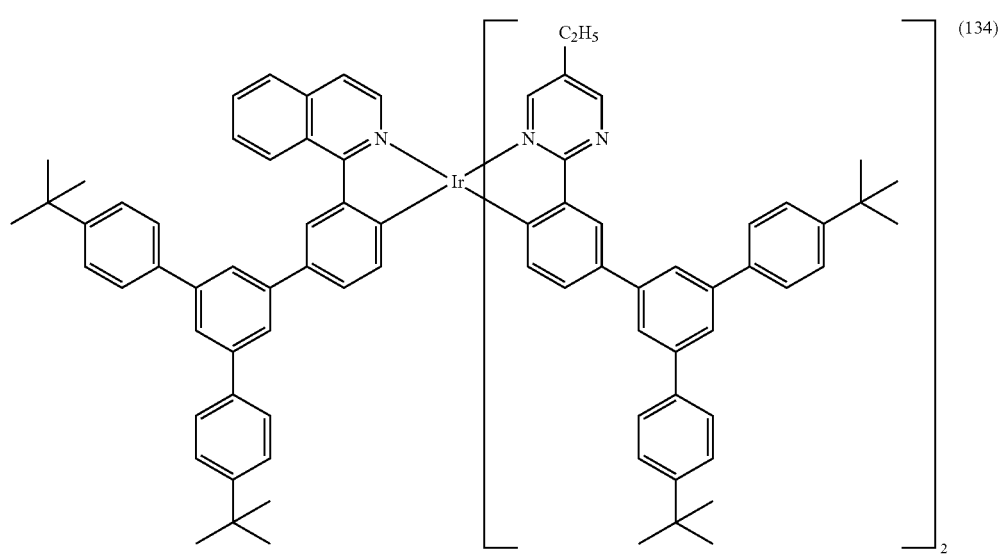
(134)

TABLE 10-continued

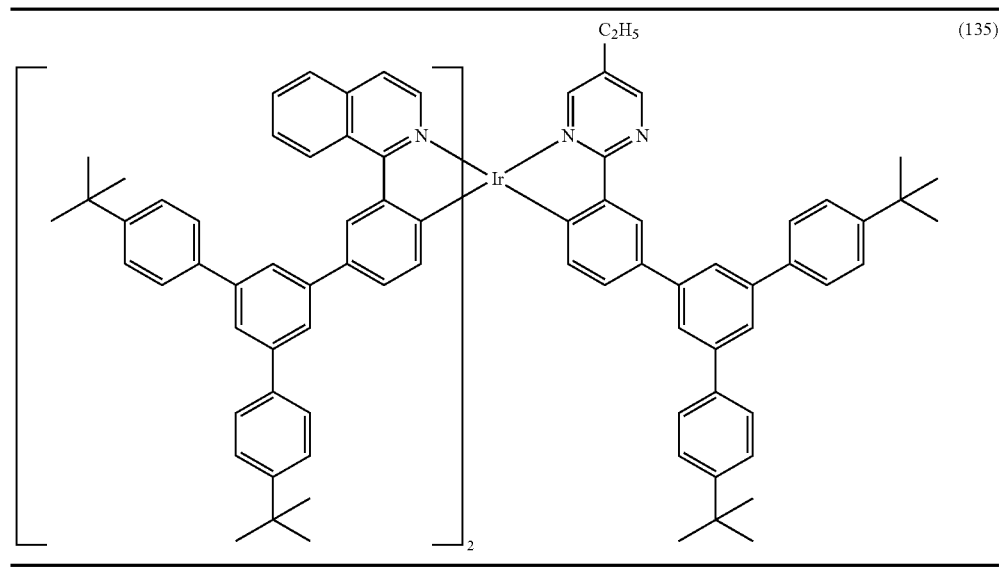
(135)

EXAMPLES

Although the present invention will next be described in detail by Examples, the present invention is not limited to this. Moreover, compounds (A) to (P) and (A-1) to (P-1) described in Examples are shown in Table 11 and Table 12.

TABLE 11

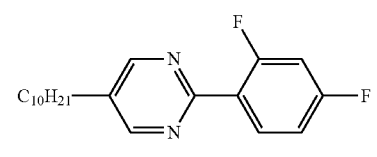
Compound (A)

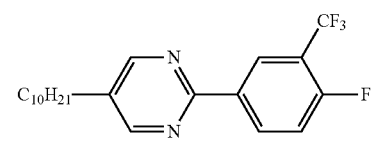
Compound (B)

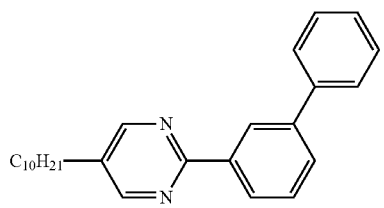
Compound (C)

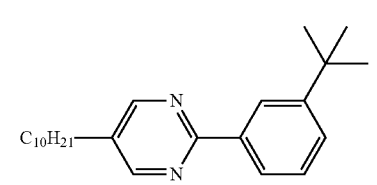
Compound (D)

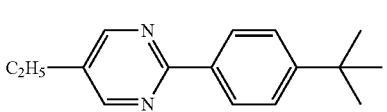
Compound (E)

TABLE 11-continued

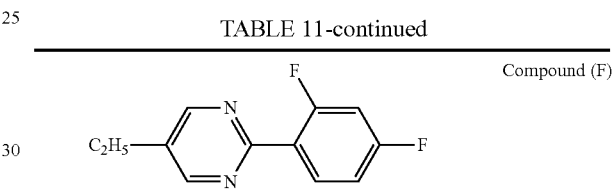
Compound (F)

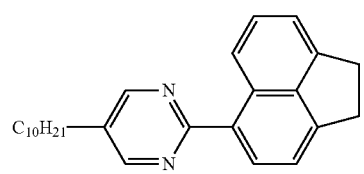
Compound (G)

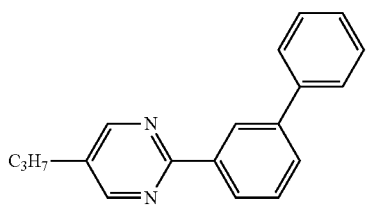
Compound (H)

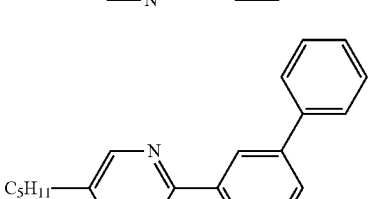
Compound (I)

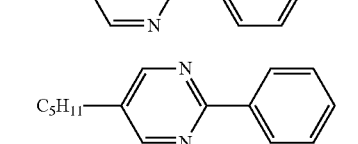
Compound (J)

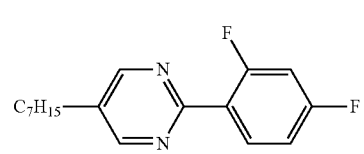
Compound (K)

TABLE 11-continued
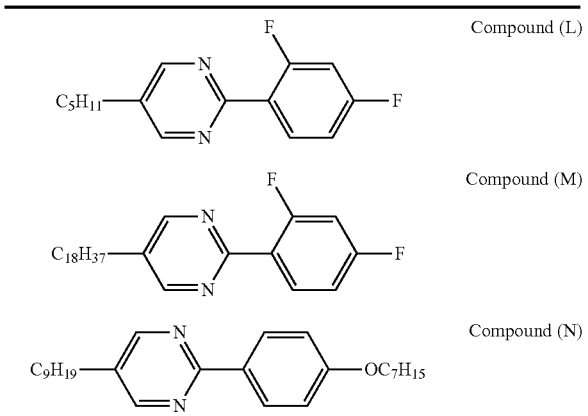
Compound (L)
Compound (M)
Compound (N)
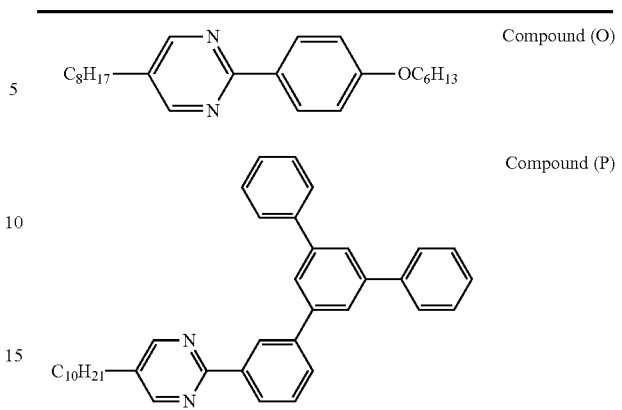
Compound (O)
Compound (P)
TABLE 12
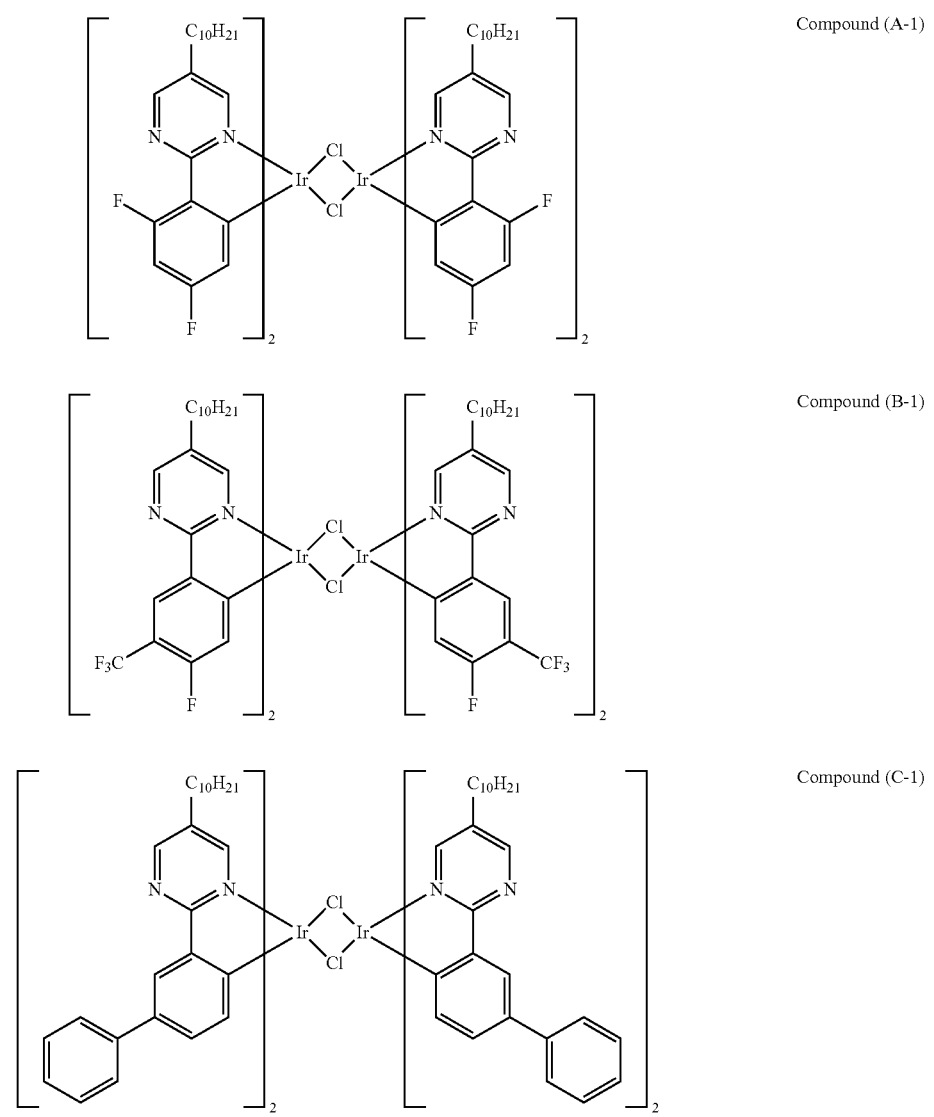
Compound (A-1)
Compound (B-1)
Compound (C-1)

TABLE 12-continued
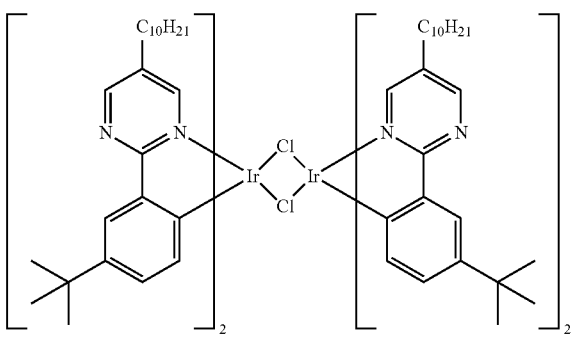
Compound (D-1)
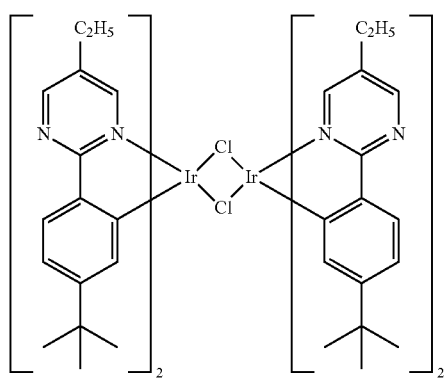
Compound (E-1)
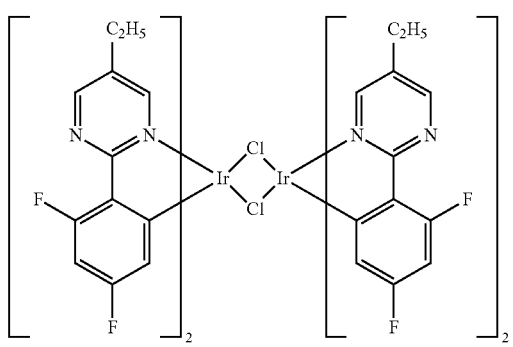
Compound (F-1)
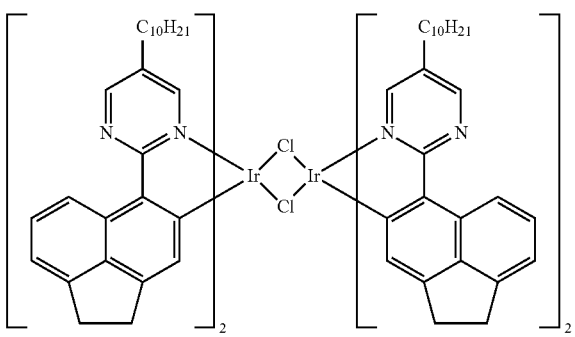
Compound (G-1)

TABLE 12-continued
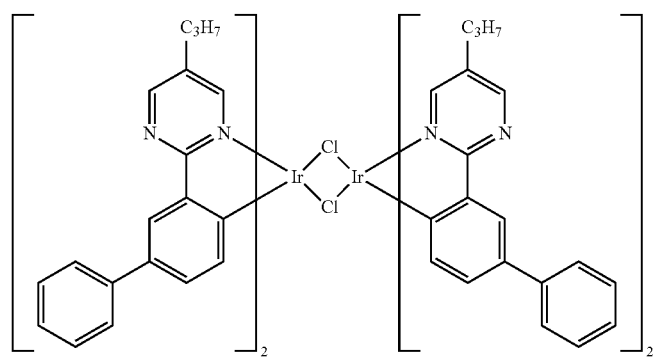
Compound (H-1)
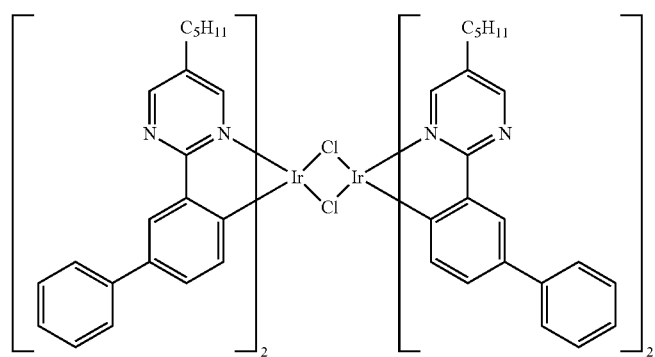
Compound (I-1)
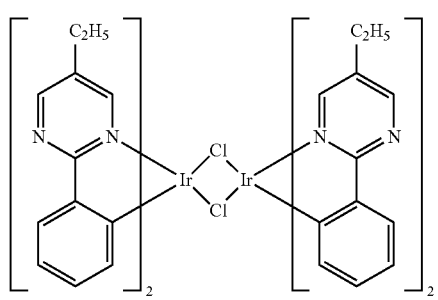
Compound (J-1)
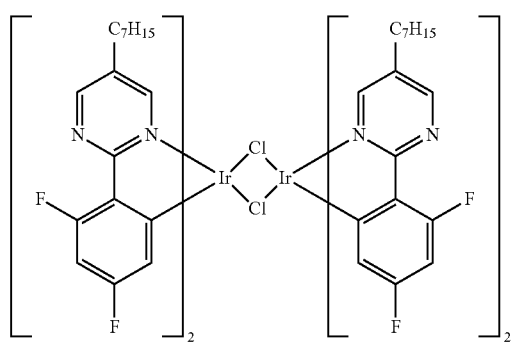
Compound (K-1)

TABLE 12-continued
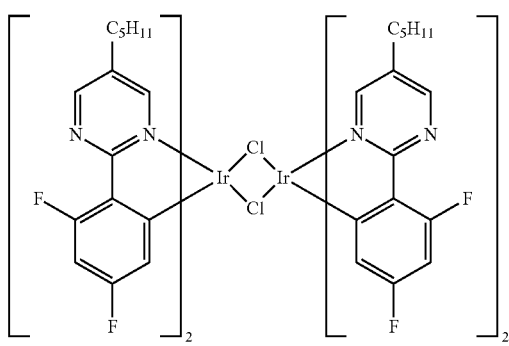
Compound (L-1)
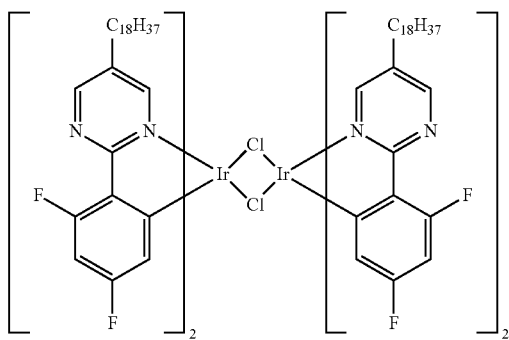
Compound (M-1)
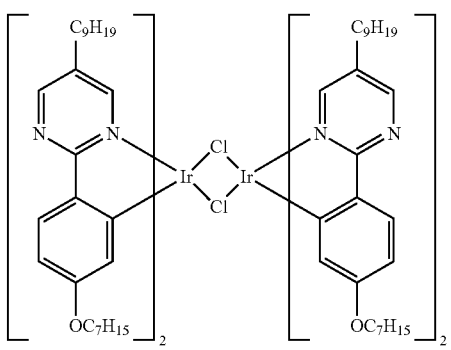
Compound (N-1)
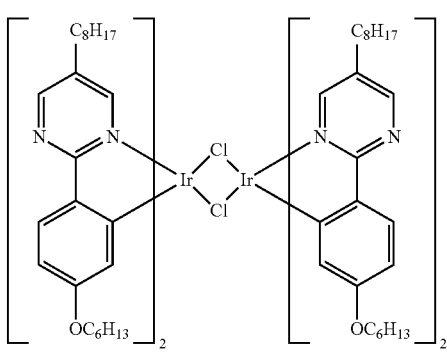
Compound (O-1)

TABLE 12-continued

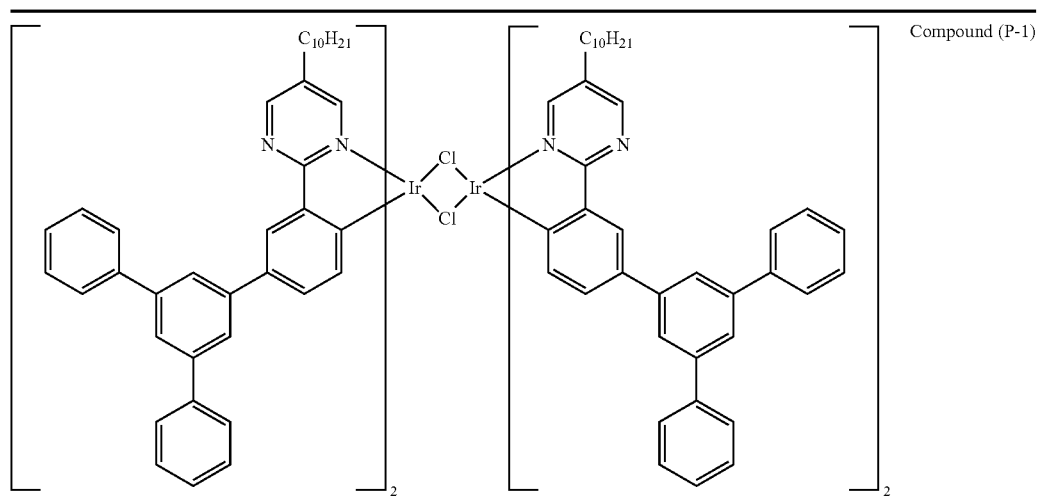

Compound (P-1)

Example 1

Synthesis of Compound (47) of the Present Invention

<Step 1 Synthesis of Compound A>

3.89 g of 2-chloro-5-n-decylpyrimidine, 2.65 g of 2,4-difluorophenylboronic acid, 35 mL of 1,2-dimethoxyethane, and 42 ml of a 2 M aqueous solution of potassium carbonate were placed in a two-neck flask. After argon gas was aerated into this solution for 20 minutes, 0.88 g of a tetrakistriphenylphosphine (0) palladium complex was placed therein. This solution was heated to reflux for 16 hours under an argon atmosphere using an oil bath. The organic layer was separated/collected and separated/purified by silica gel chromatography (eluent: a mixed solvent of dichloromethane and hexane) to obtain 4.1 g of compound A. The $^1$H-NMR data of the compound A is shown below.

$^1$H-NMR (400 MHz/CDCL$_3$): δ 8.66 (s, 2H), 8.08-8.15 (m, 1H), 6.91-7.00 (m, 2H), 2.63 (t, 2H), 1.18-1.68 (m, 16H), 0.88 (t, 3H).

<Step 2 Synthesis of Compound (A-1)>

800 mg of iridium trichloride n-hydrate, 1.58 g of the compound A, 64 ml of 2-ethoxyethanol, and 22 ml of water were placed in a two-neck flask and heated to reflux for 14 hours under an argon atmosphere. After the reaction solution was cooled to room temperature, water was added thereto, and the resulting solid was filtered to obtain compound (A-1). The isolation yield was 57%. The $^1$H-NMR data of the compound (A-1) is shown below.

$^1$H-NMR (400 MHz/CDCL$_3$): δ 9.03 (s, 4H), 8.79 (s, 4H), 6.42 (t, 4H), 5.25 (d, 4H), 2.52 (m, 4H), 2.11 (m, 4H), 1.18-1.70 (m, 64H), 0.87 (t, 12H).

<Step 3 Synthesis of Compound (47) of the Present Invention>

250 mg of the compound (A-1), 70.3 mg of acetylacetone, 149 mg of sodium carbonate, and 50 ml of 2-ethoxyethanol were placed in an eggplant-shaped flask and irradiated with microwave (2450 MHz) for 30 minutes under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (47) of the present invention at an isolation yield of 48%. The $^1$H-NMR data of the compound (47) of the present invention is shown below.

$^1$H-NMR (400 MHz/CDCL$_3$): δ 8.73 (d, 2H), 8.38 (d, 2H), 6.40 (dd, 2H), 5.71 (d, 2H), 5.26 (s, 1H), 2.69 (t, 4H), 1.18-1.82 (m, 38H), 0.88 (t, 6H).

Example 2

Synthesis of Compound (75) of the Present Invention

<Step 1 Synthesis of Compound B>

2.5 g of 2-chloro-5-n-decylpyrimidine, 2.24 g of 4-fluoro-3-(trifluoromethyl)phenylboronic acid, 22 mL of 1,2-dimethoxyethane, and 26 ml of a 2 M aqueous solution of potassium carbonate were placed in a two-neck flask. After argon gas was aerated into this solution for 20 minute, 0.57 g of a tetrakistriphenylphosphine (0) palladium complex was placed therein. This solution was heated to reflux for 14 hours under an argon atmosphere using an oil bath. The organic layer was separated/collected and separated/purified by silica gel chromatography (eluent: a mixed solvent of dichloromethane and hexane) to obtain 2.50 g of compound B. The $^1$H-NMR data of the compound B is shown below.

$^1$H-NMR (400 MHz/CDCL$_3$): δ 8.73 (d, 1H), 8.61-8.65 (m, 3H), 7.30 (d, 1H), 2.64 (t, 2H), 1.18-1.70 (m, 16H), 0.88 (t, 3H).

<Step 2 Synthesis of Compound (B-1)>

1 g of iridium trichloride n-hydrate, 2.28 g of the compound B, 80 ml of 2-ethoxyethanol, and 28 ml of water were placed in a two-neck flask and heated to reflux for 14 hours under an argon atmosphere. After the reaction solution was cooled to room temperature, water was added thereto, and the resulting solid was filtered to obtain compound (B-1). The isolation yield was 55%. The $^1$H-NMR data of the compound (B-1) is shown below.

$^1$H-NMR (400 MHz/CDCL$_3$): δ 9.07 (s, 4H), 8.79 (s, 4H), 8.29 (d, 4H), 5.64 (d, 4H), 2.59 (m, 4H), 2.17 (m, 4H), 1.18-1.70 (m, 64H), 0.87 (t, 12H).

<Step 3 Synthesis of Compound (75) of the Present Invention>

200 mg of the compound (B-1), 246 mg of sodium picolinate, and 100 ml of 2-ethoxyethanol were placed in an eggplant-shaped flask and irradiated with microwave (2450

MHz) for 10 minutes under an argon atmosphere. After the reaction solution was cooled to room temperature, the solvent was concentrated under reduced pressure to obtain solid. This solid was recrystallized from dichloromethane-hexane to obtain compound (75) of the present invention. The isolation yield was 56%. The $^1$H-NMR. data of the compound (75) of the present invention is shown below.

$^1$H-NMR (400 MHz/CDCl$_3$): δ 8.65-8.70 (m, 3H), 8.37 (d, 1H), 8.29 (d, 1H), 8.27 (d, 1H), 8.02 (t, 1H), 7.80 (d, 1H), 7.52 (t, 1H), 7.26 (d, 1H), 6.15 (d, 1H), 5.92 (d, 1H), 2.63-2.67 (m, 2H), 2.45-2.49 (m, 2H), 1.25-1.63 (m, 32H), 0.88 (t, 6H).

Example 3

Synthesis of Compound (43) of the Present Invention

<Step 1 Synthesis of Compound C>

2.5 g of 2-chloro-5-n-decylpyrimidine, 2.14 g of 3-biphenylboronic acid, 22 mL of 1,2-dimethoxyethane, and 27 ml of a 2 M aqueous solution of potassium carbonate were placed in a two-neck flask. After argon gas was aerated into this solution for 20 minute, 0.57 g of a tetrakisfriphenylphosphine (0) palladium complex was placed therein. This solution was heated to reflux for 14 hours under an argon atmosphere using an oil bath. The organic layer was separated/collected and separated/purified by silica gel chromatography (eluent: a mixed solvent of dichloromethane and hexane) to obtain 2.52 g of compound C. The $^1$H-NMR data of the compound C is shown below.

$^1$H-NMR (400 MHz/CDCl$_3$): δ 8.69 (s, 1H), 8.64 (s, 2H), 8.40 (d, 1H), 7.71 (d, 3H), 7.55 (t, 1H), 7.46 (t, 2H), 7.36 (t, 1H), 2.62 (t, 2H), 1.18-1.70 (m, 16H), 0.88 (t, 3H).

<Step 2 Synthesis of Compound (C-1)>

1 g of iridium trichloride n-hydrate, 2.21 g of the compound C, 80 ml of 2-ethoxyethanol, and 28 ml of water were placed in a two-neck flask and heated to reflux for 14 hours under an argon atmosphere. After the reaction solution was cooled to room temperature, water was added thereto, and the resulting solid was filtered to obtain compound (C-1). The isolation yield was 60%. The $^1$H-NMR data of the compound (C-1) is shown below.

$^1$H-NMR (400 MHz/CDCl$_3$): δ 9.25 (d, 4H), 8.71 (d, 4H), 8.18 (d, 4H), 7.50 (d, 8H), 7.32 (t, 8H), 7.23 (t, 4H), 6.98 (d, 4H), 6.04 (d, 4H), 2.54 (m, 4H), 2.19 (m, 4H), 1.18-1.70 (m, 64H), 0.86 (t, 12H).

<Step 3 Synthesis of Compound (43) of the Present Invention>

600 mg of the compound (C-1), 310 mg of acetylacetone, 328 mg of sodium carbonate, and 300 ml of 2-ethoxyethanol were reacted at 100° C. for 16 hours under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (43) of the present invention at an isolation yield of 23%. The $^1$H-NMR data of the compound (43) of the present invention is shown below.

$^1$H-NMR (400 MHz/CDCl$_3$): δ 8.65 (d, 2H), 8.52 (d, 2H), 8.21 (d, 2H), 7.57 (d, 4H), 7.34 (t, 4H), 7.23 (t, 2H), 7.08 (d, 2H), 6.43 (d, 2H), 5.25 (s, 1H), 2.71 (t, 4H), 1.18-1.83 (m, 38H), 0.87 (t, 6H).

Example 4

Synthesis of Compound (39) of the Present Invention

<Step 1 Synthesis of Compound D>

1.5 g of 2-chloro-5-n-decylpyrimidine, 1.15 g of m-t-butylphenylboronic acid, 13 mL of 1,2-dimethoxyethane, and 16 ml of a 2 M aqueous solution of potassium carbonate were placed in a two-neck flask. After argon gas was aerated into this solution for 20 minute, 0.45 g of a tetrakistriphenylphosphine (0) palladium complex was placed therein. This solution was heated to reflux for 14 hours under an argon atmosphere using an oil bath. The organic layer was separated/collected and separated/purified by silica gel chromatography (eluent: a mixed solvent of dichloromethane and hexane) to obtain 1.58 g of compound D. The $^1$H-NMR data of the compound D is shown below.

$^1$H-NMR (400 MHz/CDCl$_3$): δ 8.62 (s, 2H), 8.47 (s, 1H), 8.22 (d, 1H), 7.51 (d, 1H), 7.42 (t, 1H), 2.62 (t, 2H), 1.18-1.70 (m, 25H), 0.88 (t, 3H).

<Step 2 Synthesis of Compound (D-1)>

500 mg of iridium trichloride n-hydrate, 1.05 g of the compound D, 40 ml of 2-ethoxyethanol, and 14 ml of water were placed in a two-neck flask and heated to reflux for 14 hours under an argon atmosphere. After the reaction solution was cooled to room temperature, water was added thereto, and the resulting solid was filtered to obtain compound (D-1). The isolation yield was 73%. The $^1$H-NMR data of the compound (D-1) is shown below.

$^1$H-NMR (400 MHz/CDCl$_3$): δ 9.09 (d, 4H), 8.63 (d, 4H), 7.90 (d, 4H), 6.73 (d, 4H), 5.89 (d, 4H), 2.49 (m, 4H), 2.15 (m, 4H), 1.18-1.70 (m, 100H), 0.86 (t, 12H).

<Step 3 Synthesis of Compound (39) of the Present Invention>

300 mg of the compound (D-1), 161 mg of acetylacetone, 171 mg of sodium carbonate, and 150 ml of 2-ethoxyethanol were reacted at 100° C. for 16 hours under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (39) of the present invention at an isolation yield of 46%. The $^1$H-NMR data of the compound (39) of the present invention is shown below.

$^1$H-NMR (400 MHz/CDCl$_3$): δ 8.58 (d, 2H), 8.48 (d, 2H), 7.97 (d, 2H), 6.88 (d, 2H), 6.28 (d, 2H), 5.19 (s, 1H), 2.65 (t, 4H), 1.18-1.78 (m, 56H), 0.88 (t, 6H).

Example 5

Synthesis of Compound (36) of the Present Invention

<Step 1 Synthesis of Compound E>

5 g of 2-chloro-5-ethylpyrimidine, 6.87 g of 4-tert-butylphenylboronic acid, 40 mL of 1,2-dimethoxyethane, and 48 ml of a 2 M aqueous solution of potassium carbonate were placed in a two-neck flask. After argon gas was aerated into this solution for 20 minute, 2.0 g of a tetrakistriphenylphosphine (0) palladium complex was placed therein. This solution was heated to reflux for 16 hours under an argon atmosphere using an oil bath. The organic layer was separated/collected and separated/purified by silica gel chromatography (eluent: a mixed solvent of dichloromethane and hexane) to obtain 4.3 g of compound E. The $^1$H-NMR data of the compound E is shown below.

¹H-NMR (400 MHz/CDCL₃): δ 8.63 (s, 2H), 8.33 (d, 2H), 7.50 (d, 2H), 2.66 (q, 2H), 1.37 (s, 9H), 1.30 (t, 3H).

<Step 2 Synthesis of Compound (E-1)>

1 g of iridium trichloride n-hydrate, 1.44 g of the compound E, 80 ml of 2-ethoxyethanol, and 28 ml of water were placed in a two-neck flask and heated to reflux for 14 hours under an argon atmosphere. After the reaction solution was cooled to room temperature, water was added thereto, and the resulting solid was filtered to obtain compound (E-1). The isolation yield was 92%. The ¹H-NMR data of the compound (E-1) is shown below.

¹H-NMR (400 MHz/CDCL₃): δ 9.28 (d, 4H), 8.65 (d, 4H), 7.78 (d, 4H), 6.89 (d, 4H), 5.97 (d, 4H), 2.50 (m, 4H), 2.20 (m, 4H), 1.24 (t, 12H), 0.97 (s, 36H).

<Step 3 Synthesis of Compound (36) of the Present Invention>

300 mg of the compound (E-1), 212 mg of acetylacetone, 225 mg of sodium carbonate, and 120 ml of 2-ethoxyethanol were reacted at 100° C. for 16 hours under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (36) of the present invention at an isolation yield of 37%. The ¹H-NMR data of the compound (36) of the present invention is shown below.

¹H-NMR (400 MHz/CDCL₃): δ 8.59 (d, 2H), 8.50 (d, 2H), 7.79 (d, 2H), 6.91 (d, 2H), 6.23 (d, 2H), 5.20 (s, 1H), 2.66-2.78 (m, 4H), 1.81 (s, 6H), 1.33 (t, 6H), 1.07 (s, 18H).

Example 6

Synthesis of Compound (76) of the Present Invention

<Step 1 Synthesis of Compound F>

10 g of 2-chloro-5-ethylpyrimidine, 12.2 g of 2,4-difluorophenylboronic acid, 80 mL of 1,2-dimethoxyethane, and 96 ml of a 2 M aqueous solution of potassium carbonate were placed in a two-neck flask. After argon gas was aerated into this solution for 20 minute, 4.1 g of a tetrakistriphenylphosphine (0) palladium complex was placed therein. This solution was heated to reflux for 16 hours under an argon atmosphere using an oil bath. The organic layer was separated/collected. The solid obtained after the solvent was distilled off under reduced pressure was separated/purified by silica gel chromatography (eluent: a mixed solvent of dichloromethane and hexane) to obtain 13.3 g of compound F. The ¹H-NMR data of the compound F is shown below.

¹H-NMR (400 MHz/CDCL₃): δ 8.70 (s, 2H), 8.08 (m, 1H), 6.92-7.01 (m, 2H), 2.70 (q, 2H), 1.32 (t, 311).

<Step 2 Synthesis of Compound (F-1)>

1 g of iridium trichloride n-hydrate, 1.31 g of the compound F, 80 ml of 2-ethoxyethanol, and 28 ml of water were placed in a two-neck flask and heated to reflux for 14 hours under an argon atmosphere. After the reaction solution was cooled to room temperature, water was added thereto, and the resulting solid was filtered to obtain compound (F-1). The isolation yield was 87%. The ¹H-NMR data of the compound (F-1) is shown below.

¹H-NMR (400 MHz/CDCL₃): δ 9.10 (d, 4H), 8.83 (d, 4H), 6.43 (dd, 4H), 5.24 (d, 4H), 2.48-2.58 (m, 4H), 2.23-2.33 (m, 4H), 1.25 (t, 12H).

<Step 3 Synthesis of Compound (76) of the Present Invention>

200 mg of the compound (F-1), 109 mg of sodium picolinate, and 80 ml of 2-ethoxyethanol were placed in an egg-plant-shaped flask and irradiated with microwave (2450 MHz) for 10 minutes under an argon atmosphere. After the reaction solution was cooled to room temperature, the solvent was concentrated under reduced pressure to obtain solid. This solid was recrystallized from dichloromethane-hexane to obtain compound (76) of the present invention. The isolation yield was 94%. The ¹H-NMR data of the compound (76) of the present invention is shown below.

¹H-NMR (400 MHz/CDCL₃): δ 8.72-8.75 (m, 3H), 8.37 (d, 1H), 8.02 (t, 1H), 7.84 (d, 1H), 7.50 (dd, 1H), 7.28 (d, 1H), 6.54 (dd, 1H), 6.47 (dd, 1H), 5.84 (d, 1H), 5.60 (d, 1H), 2.67-2.74 (m, 2H), 2.49-2.55 (m, 2H), 1.28 (t, 3H), 1.12 (t, 3H).

Example 7

Synthesis of Compound (53) of the Present Invention

<Step 1 Synthesis of Compound G>

1.5 g of 2-chloro-5-n-decylpyrimidine, 1.28 g of acenaphthene-5-boronic acid, 13 mL of 1,2-dimethoxyethane, and 16 ml of a 2 M aqueous solution of potassium carbonate were placed in a two-neck flask. After argon gas was aerated into this solution for 20 minute, 0.34 g of a tetrakistriphenylphosphine (0) palladium complex was placed therein. This solution was heated to reflux for 12 hours under an argon atmosphere using an oil bath. The organic layer was separated/collected and separated/purified by silica gel chromatography (eluent: a mixed solvent of dichloromethane and hexane) to obtain compound G. The isolation yield was 67%. The ¹H-NMR data of the compound G is shown below.

¹H-NMR (400 MHz/CDCL₃): δ 8.77 (s, 1H), 8.66 (s, 2H), 8.33 (d, 1H), 7.51 (dd, 1H), 7.34 (d, 1H), 7.27 (d, 1H), 3.34 (s, 4H), 2.53 (t, 2H), 1.25-1.64 (m, 16H), 0.87 (t, 3H).

<Step 2 Synthesis of Compound (G-1)>

500 mg of iridium trichloride n-hydrate, 1.11 g of the compound G, 40 ml of 2-ethoxyethanol, and 14 ml of water were placed in a two-neck flask and heated to reflux for 12 hours under an argon atmosphere. After the reaction solution was cooled to room temperature, water was added thereto, and the resulting solid was filtered to obtain compound (G-1). The isolation yield was 74%.

<Step 3 Synthesis of Compound (53) of the Present Invention>

500 mg of the compound (G-1), 258 mg of acetylacetone, 273 mg of sodium carbonate, and 200 ml of 2-ethoxyethanol were reacted at 100° C. for 12 hours under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (53) of the present invention at an isolation yield of 24%. The ¹H-NMR data of the compound (53) of the present invention is shown below.

¹H-NMR (400 MHz/CDCL₃): δ 9.29 (d, 2H), 8.73 (s, 2H), 8.48 (s, 2H), 7.47 (t, 2H), 7.09 (t, 2H), 6.41 (s, 2H), 5.23 (s, 1H), 2.99-3.18 (m, 8H), 2.66 (t, 4H), 1.26-1.78 (m, 38H), 0.88 (t, 6H).

Example 8

Synthesis of Compound (12) of the Present Invention 500 mg of the compound (A-1), 152 mg of AgCF₃SO₃, and 250 ml of acetonitrile were heated to reflux for 16 hours under an argon atmosphere. The reaction solution was cooled to room temperature and then filtered through a celite layer, the filtrate was concentrated under reduced pressure, and a saturated aqueous solution of $NH_4PF_6$ was added thereto. The deposited solid was filtered to obtain an intermediate. Subsequently, 250 mg of this intermediate, 154 mg of the compound (A), and 10 ml of ethylene glycol were reacted by heating at 190° C. for 16 hours under an argon atmosphere. The deposited solid was separated/purified by silica gel chromatography (eluent: a mixed solvent of dichloromethane and hexane) to obtain compound (12) of the present invention at an isolation yield of 40%. Meridional forms and facial forms were obtained. The $^1$H-NMR data of the compound (12) of the present invention is shown below.
(NMR Data of Meridional Forms)
$^1$H-NMR (400 MHz/CDCL$_3$): δ 8.68 (d, 1H), 8.58 (s, 2H), 7.96 (d, 1H), 7.81 (d, 1H), 7.42 (d, 1H), 6.47-6.55 (m, 3H), 6.39 (d, 1H), 5.99 (d, 1H), 5.78 (d, 1H), 2.40-2.48 (m, 6H), 1.20-1.47 (m, 48H), 0.88 (t, 9H).
(NMR Data of Facial Forms)
$^1$H-NMR (400 MHz/CDCL$_3$): δ 8.67 (d, 3H), 7.42 (d, 3H), 6.46 (dd, 3H), 6.27 (d, 3H), 2.40-2.48 (m, 6H), 0.87-1.46 (m, 57H).

Moreover, for confirming solubility in solvents (chloroform and toluene), a 0.1 wt % solution was prepared and confirmed by visual observation, demonstrating that the compound of the present invention was completely dissolved.

Example 9

Synthesis of Compound (82) of the Present Invention 111 mg of the compound (A-1), 45 mg of sodium picolinate, and 40 ml of 2-ethoxyethanol were placed in an eggplant-shaped flask and irradiated with microwave (2450 MHz) for 10 minutes under an argon atmosphere. After the reaction solution was cooled to room temperature, the solvent was concentrated under reduced pressure to obtain solid. This solid was recrystallized from dichloromethane-hexane to obtain compound (82) of the present invention. The isolation yield was 74%. The $^1$H-NMR data of the compound (82) of the present invention is shown below.
$^1$H-NMR (400 MHz/CDCL$_3$): δ 8.68-8.72 (m, 3H), 8.36 (d, 1H), 8.01 (t, 1H), 7.83 (d, 1H), 7.49 (dd, 1H), 7.26 (d, 1H), 6.54 (dd, 1H), 6.47 (dd, 1H), 5.83 (d, 1H), 5.60 (d, 1H), 2.60-2.67 (m, 2H), 2.39-2.48 (m, 2H), 1.23-1.60 (m, 32H), 0.88 (t, 6H).

Example 10

Synthesis of Compound (111) of the Present Invention 90 mg of the compound (A-1), 29 mg of 2,2'-dipyridylamine, and 30 ml of 2-ethoxyethanol were placed in an eggplant-shaped flask and irradiated with microwave (2450 MHz) for 5 minutes under an argon atmosphere. After the reaction solution was cooled to room temperature, the solvent was concentrated under reduced pressure, and a saturated aqueous solution of $NH_4PF_6$ was added to obtain solid. This solid was recrystallized from dichloromethane and hexane to obtain compound (111) of the present invention at an isolation yield of 69%.

Example 11

Synthesis of Compound (113) of the Present Invention 90 mg of the compound (A-1), 26 mg of 2,2'-bipyridine, and 30 ml of 2-ethoxyethanol were placed in an eggplant-shaped flask and irradiated with microwave (2450 MHz) for 5 minutes under an argon atmosphere. After the reaction solution was cooled to room temperature, the solvent was concentrated under reduced pressure, and a saturated aqueous solution of $NH_4PF_6$ was added to obtain solid. This solid was recrystallized from dichloromethane and hexane to obtain compound (113) of the present invention at an isolation yield of 72%. The $^1$H-NMR data of the compound (113) of the present invention is shown below.
$^1$H-NMR (400 MHz/CDCL$_3$): δ 9.05 (d, 2H), 8.73 (s, 2H), 8.29 (t, 2H), 7.96 (d, 2H), 7.54 (t, 2H), 7.43 (s, 2H), 6.63 (t, 2H), 5.71 (d, 2H), 2.49 (t, 4H), 1.21-1.59 (m, 32H), 0.88 (t, 6H).

Example 12

Synthesis of Compound (41) of the Present Invention

<Step 1 Synthesis of Compound H>
3 g of 2-chloro-5-n-propylpyrimidine, 4.17 g of 3-biphenylboronic acid, 19 mL of 1,2-dimethoxyethane, and 23 ml of a 2 M aqueous solution of potassium carbonate were placed in a two-neck flask. After argon gas was aerated into this solution for 20 minute, 1.11 g of a tetrakistriphenylphosphine (0) palladium complex was placed therein. This solution was heated to reflux for 14 hours under an argon atmosphere using an oil bath. The organic layer was separated/collected and separated/purified by silica gel chromatography (eluent: a mixed solvent of dichloromethane and hexane) to obtain 3.81 g of compound H. The $^1$H-NMR data of the compound H is shown below.
$^1$H-NMR (400 MHz/CDCL$_3$): δ 8.68 (s, 1H), 8.65 (s, 2H), 8.40 (d, 1H), 7.71 (d, 3H), 7.56 (t, 1H), 7.46 (t, 2H), 7.36 (t, 1H), 2.61 (t, 2H), 1.70 (m, 2H), 1.00 (t, 3H).
<Step 2 Synthesis of Compound (H-1)>
500 mg of iridium trichloride n-hydrate, 871 mg of the compound H, 40 ml of 2-ethoxyethanol, and 14 ml of water were placed in a two-neck flask and heated to reflux for 14 hours under an argon atmosphere. After the reaction solution was cooled to room temperature, water was added thereto, and the resulting solid was filtered to obtain compound (H-1). The isolation yield was 68%. The $^1$H-NMR data of the compound (H-1) is shown below.
$^1$H-NMR (400 MHz/CDCL$_3$): δ 9.26 (d, 4H), 8.72 (d, 4H), 8.19 (d, 4H), 7.51 (d, 8H), 7.33 (t, 8H), 7.24 (t, 4H), 6.98 (d, 4H), 6.05 (d, 4H), 2.54 (m, 4H), 2.17 (m, 4H), 1.67 (m, 8H), 1.03 (t, 12H).
<Step 3 Synthesis of Compound (41) of the Present Invention>
390 mg of the compound (H-1), 252 mg of acetylacetone, 267 mg of sodium carbonate, and 150 ml of 2-ethoxyethanol were reacted at 100° C. for 16 hours under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (41) of the present invention at an isolation yield of 53%. The $^1$H-NMR data of the compound (41) of the present invention is shown below.
$^1$H-NMR (400 MHz/CDCL$_3$): δ 8.65 (d, 2H), 8.52 (d, 2H), 8.21 (d, 2H), 7.57 (d, 4H), 7.34 (t, 4H), 7.22 (t, 2H), 7.09 (d, 2H), 6.43 (d, 2H), 5.26 (s, 1H), 2.70 (t, 4H), 1.67-1.83 (m, 10H), 1.03 (t, 6H).

Example 13

Synthesis of Compound (42) of the Present Invention

<Step 1 Synthesis of Compound I>

3 g of 2-chloro-5-n-pentylpyrimidine, 3.54 g of biphenylboronic acid, 19 mL of 1,2-dimethoxyethane, and 23 ml of a 2 M aqueous solution of potassium carbonate were placed in a two-neck flask. After argon gas was aerated into this solution for 20 minute, 0.939 g of a tetrakistriphenylphosphine (0) palladium complex was placed therein. This solution was heated to reflux for 14 hours under an argon atmosphere using an oil bath. The organic layer was separated/collected and separated/purified by silica gel chromatography (eluent: a mixed solvent of dichloromethane and hexane) to obtain 3.65 g of compound I. The $^1$H-NMR data of the compound I is shown below.

$^1$H-NMR (400 MHz/CDCL$_3$): δ 8.69 (s, 1H), 8.64 (s, 2H), 8.40 (d, 1H), 7.71 (d, 3H), 7.55 (t, 1H), 7.46 (t, 2H), 7.36 (t, 1H), 2.62 (t, 2H), 1.31-1.70 (m, 6H), 0.90 (t, 3H).

<Step 2 Synthesis of Compound (I-1)>

500 mg of iridium trichloride n-hydrate, 901 mg of the compound I, 40 ml of 2-ethoxyethanol, and 14 ml of water were placed in a two-neck flask and heated to reflux for 14 hours under an argon atmosphere. After the reaction solution was cooled to room temperature, water was added thereto, and the resulting solid was filtered to obtain compound (I-1). The isolation yield was 72%. The $^1$H-NMR data of the compound (I-1) is shown below.

$^1$H-NMR (400 MHz/CDCL$_3$): δ 9.26 (d, 4H), 8.71 (d, 4H), 8.19 (d, 4H), 7.50 (d, 8H), 7.33 (t, 8H), 7.23 (d, 4H), 6.98 (d, 4H), 6.05 (d, 4H), 2.54 (m, 4H), 2.19 (m, 4H), 1.36-1.63 (m, 24H), 0.86 (t, 12H).

<Step 3 Synthesis of Compound (42) of the Present Invention>

378 mg of the compound (I-1), 228 mg of acetylacetone, 241 mg of sodium carbonate, and 150 ml of 2-ethoxyethanol were reacted at 100° C. for 16 hours under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (42) of the present invention at an isolation yield of 48%. The $^1$H-NMR data of the compound (42) of the present invention is shown below.

$^1$H-NMR (400 MHz/CDCL$_3$): δ 8.65 (d, 2H), 8.52 (d, 2H), 8.21 (d, 2H), 7.57 (d, 4H), 7.34 (t, 4H), 7.23 (t, 2H), 7.08 (d, 2H), 6.43 (d, 2H), 5.25 (s, 1H), 2.71 (t, 4H), 1.35-1.83 (m, 18H), 0.93 (t, 6H).

Example 14

Synthesis of Compound (124) of the Present Invention 500 mg of the compound (A-1), 152 mg of AgCF$_3$SO$_3$, and 250 ml of acetonitrile were heated to reflux for 16 hours under an argon atmosphere. The reaction solution was cooled to room temperature and then filtered through a celite layer, the filtrate was concentrated under reduced pressure, and a saturated aqueous solution of NH$_4$PF$_6$ was added thereto. The deposited solid was filtered to obtain an intermediate. Subsequently, 450 mg of this intermediate, 265 mg of potassium salt of tetrakis(1-pyrazolyl)borate, and 150 ml of acetonitrile were heated to reflux for 72 hours under an argon atmosphere. The deposited solid from the solution after reaction was separated/purified by silica gel chromatography (eluent: a mixed solvent of dichloromethane and methanol) to obtain compound (124) of the present invention at an isolation yield of 40%. The $^1$H-NMR data of the compound (124) of the present invention is shown below.

$^1$H-NMR (400 MHz/CDCL$_3$): δ 8.55 (s, 2H), 7.66 (s, 2H), 7.14-7.17 (m, 4H), 6.99 (s, 2H), 6.53 (dd, 2H), 6.27 (s, 2H), 6.17 (s, 2H), 6.03 (s, 2H), 5.61 (d, 2H), 2.34-2.49 (m, 4H), 1.23-1.63 (m, 32H), 0.88 (t, 6H).

Example 15

Synthesis of Compound (1) of the Present Invention

<Step 1 Synthesis of Compound J>

3 g of 2-chloro-5-ethylpyrimidine, 2.82 g of phenylboronic acid, 30 mL of 1,2-dimethoxyethane, and 25 ml of a 2 M aqueous solution of potassium carbonate were placed in a two-neck flask. After argon gas was aerated into this solution for 20 minute, 1.22 g of a tetrakistriphenylphosphine (0) palladium complex was placed therein. This solution was heated to reflux for 52.5 hours under an argon atmosphere using an oil bath. The organic layer was separated/collected and separated/purified by silica gel chromatography (eluent: a mixed solvent of dichloromethane and hexane) to obtain 2.87 g of compound J. The $^1$H-NMR data of the compound J is shown below.

$^1$H-NMR (400 MHz/CDCL$_3$): δ 8.59 (s, 2H), 8.43 (d, 2H), 7.41-7.50 (m, 3H), 2.58 (q, 2H), 1.23 (t, 3H).

<Step 2 Synthesis of Compound (J-1)>

300 mg of iridium trichloride n-hydrate, 328 mg of the compound J, 20 ml of 2-ethoxyethanol, and 7 ml of water were placed in a two-neck flask and heated to reflux for 17 hours under an argon atmosphere. After the reaction solution was cooled to room temperature, water was added thereto, and the resulting solid was filtered to obtain compound (J-1). The isolation yield was 86%. The $^1$H-NMR data of the compound (J-1) is shown below.

$^1$H-NMR (400 MHz/CDCL$_3$): δ 9.25 (s, 4H), 8.68 (s, 4H), 7.88 (d, 4H), 6.83 (t, 4H), 6.68 (t, 4H), 5.87 (d, 4H), 2.23-2.56 (m, 8H), 1.25 (t, 12H).

<Step 3 Synthesis of Compound (1) of the Present Invention>

139 mg of the compound (J-1), 60 mg of AgCF$_3$SO$_3$, and 215 mg of the compound J were heated to reflux for 41 hours under an argon atmosphere. After cooling to room temperature, 50 ml of dichloromethane was added thereto, and insoluble matter was removed by filtration through a celite layer. Then, solid obtained by concentrating the filtrate under reduced pressure was separated/purified by silica gel chromatography (eluent: a mixed solvent of dichloromethane and ethyl acetate) to obtain compound (1) of the present invention at an isolation yield of 20%. The $^1$H-NMR data of the compound (1) of the present invention is shown below.

$^1$H-NMR (400 MHz/CDCL$_3$): δ 8.57 (s, 3H), 8.05 (d, 3H), 7.52 (s, 3H), 6.99 (t, 3H), 6.92 (t, 3H), 6.81 (d, 3H), 2.49 (q, 6H), 1.13 (t, 9H).

Example 16

Synthesis of Compound (91) of the Present Invention 300 mg of the compound (A-1), 151 mg of 5-butylpicolinic acid, 178 mg of sodium carbonate, and 100 ml of 2-ethoxyethanol were placed in an eggplant-shaped flask and irradiated with microwave (2450 MHz) for 10 minutes under an argon atmosphere. After the reaction solution was cooled to room temperature, the solvent was concentrated under reduced pressure to obtain solid. This solid was recrystallized from dichloromethane-hexane to obtain compound (91) of the present invention. The isolation yield was 70%. The $^1$H-NMR data of the compound (91) of the present invention is shown below.

$^1$H-NMR (400 MHz/CDCL$_3$): δ 8.68-8.72 (m, 3H), 8.25 (d, 1H), 7.79 (d, 1H), 7.55 (s, 1H), 7.24 (s, 1H), 6.55 (t, 1H), 6.46 (t, 1H), 5.83 (d, 1H), 5.60 (d, 1H), 2.62-2.65 (m, 2H), 2.55-2.59 (m, 2H), 2.39-2.49 (m, 2H), 1.23-1.61 (m, 38H), 0.88 (m, 9H).

Example 17

Synthesis of Compound (92) of the Present Invention

<Step 1 Synthesis of Compound K>
5 g of 2-chloro-5-n-heptylpyrimidine, 4.08 g of 2,4-difluorophenylboronic acid, 53 mL of 1,2-dimethoxyethane, and 64 ml of a 2 M aqueous solution of potassium carbonate were placed in a two-neck flask. After argon gas was aerated into this solution for 20 minute, 1.36 g of a tetrakistriphenylphosphine (0) palladium complex was placed therein. This solution was heated to reflux for 16 hours under an argon atmosphere using an oil bath. The organic layer was separated/collected and separated/purified by silica gel chromatography (eluent: a mixed solvent of dichloromethane and hexane) to obtain 5.57 g of compound K. The $^1$H-NMR data of the compound K is shown below.

$^1$H-NMR (400 MHz/CDCL$_3$): δ 8.68 (s, 2H), 8.05-8.11 (m, 1H), 6.92-7.02 (m, 2H), 2.64 (t, 2H), 1.63-1.71 (m, 2H), 1.26-1.39 (m, 8H), 0.89 (t, 3H).

<Step 2 Synthesis of Compound (K-1)>
500 mg of iridium trichloride n-hydrate, 865 mg of the compound K, 20 ml of 2-ethoxyethanol, and 7 ml of water were placed in a two-neck flask and heated to reflux for 12.5 hours under an argon atmosphere. After the reaction solution was cooled to room temperature, water was added thereto, and the resulting solid was filtered and recrystallized from dichloromethane-hexane to obtain compound (K-1). The isolation yield was 71%. The $^1$H-NMR data of the compound (K-1) is shown below.

$^1$H-NMR (400 MHz/CDCL$_3$): δ 9.03 (s, 4H), 8.80 (s, 4H), 6.43 (t, 4H), 5.25 (d, 4H), 2.49-2.56 (m, 4H), 2.07-2.15 (m, 4H), 1.26-1.56 (m, 40H). 0.86 (t, 12H).

<Step 3 Synthesis of Compound (92) of the Present Invention>
500 mg of the compound (K-1), 225 mg of sodium picolinate, and 120 ml of 2-ethoxyethanol were placed in an eggplant-shaped flask and irradiated with microwave (2450 MHz) for 10 minutes under an argon atmosphere. After the reaction solution was cooled to room temperature, the solvent was concentrated under reduced pressure to obtain solid. This solid was recrystallized from dichloromethane-hexane to obtain compound (92) of the present invention. The isolation yield was 81%. The $^1$H-NMR data of the compound (92) of the present invention is shown below.

$^1$H-NMR (400 MHz/CDCL$_3$): δ 8.68-8.73 (m, 3H), 8.36 (d, 1H), 8.01 (t, 1H), 7.83 (d, 1H), 7.50 (dd, 1H), 7.28 (d, 1H), 6.54 (t, 1H), 6.47 (t, 1H), 5.83 (d, 1H), 5.60 (d, 1H), 2.62-2.66 (m, 2H), 2.40-2.49 (m, 2H), 1.23-1.60 (m, 20H), 0.85-0.90 (m, 6H).

Example 18

Synthesis of Compound (93) of the Present Invention

<Step 1 Synthesis of Compound L>
2 g of 2-chloro-5-n-pentylpyrimidine, 1.88 g of 2,4-difluorophenylboronic acid, 25 mL of 1,2-dimethoxyethane, and 30 ml of a 2 M aqueous solution of potassium carbonate were placed in a two-neck flask. After argon gas was aerated into this solution for 20 minute, 625 mg of a tetrakistriphenylphosphine (0) palladium complex was placed therein. This solution was heated to reflux for 16 hours under an argon atmosphere using an oil bath. The organic layer was separated/collected and separated/purified by silica gel chromatography (eluent: a mixed solvent of dichloromethane and hexane) to obtain 2.57 g of compound L. The $^1$H-NMR data of the compound L is shown below.

$^1$H-NMR (400 MHz/CDCL$_3$): δ 8.71 (s, 2H), 8.05-8.11 (m, 1H), 6.92-7.01 (m, 2H), 2.64 (t, 2H), 1.64-1.71 (m, 2H), 1.32-1.43 (m, 4H), 0.93 (t, 3H).

<Step 2 Synthesis of Compound (L-1)>
500 mg of iridium trichloride n-hydrate, 0.813 g of the compound L, 20 ml of 2-ethoxyethanol, and 7 ml of water were placed in a two-neck flask and heated to reflux for 12.5 hours under an argon atmosphere. After the reaction solution was cooled to room temperature, water was added thereto, and the resulting solid was filtered and recrystallized from dichloromethane-hexane to obtain compound (L-1). The isolation yield was 79%. The $^1$H-NMR data of the compound (L-1) is shown below.

$^1$H-NMR (400 MHz/CDCL$_3$): δ 9.03 (s, 4H), 8.80 (s, 4H), 6.43 (t, 4H), 5.26 (d, 4H), 2.50-2.57 (m, 4H), 2.07-2.15 (m, 4H), 1.27-1.65 (m, 24H). 0.88 (t, 12H).

<Step 3 Synthesis of Compound (93) of the Present Invention>
300 mg of the compound (L-1), 830 mg of sodium picolinate, and 40 ml of 2-ethoxyethanol were placed in an eggplant-shaped flask and irradiated with microwave (2450 MHz) for 10 minutes under an argon atmosphere. After the reaction solution was cooled to room temperature, the solvent was concentrated under reduced pressure to obtain solid. This solid was recrystallized from dichloromethane-hexane to obtain compound (93) of the present invention. The isolation yield was 74%. The $^1$H-NMR data of the compound (93) of the present invention is shown below.

$^1$H-NMR (400 MHz/CDCL$_3$): δ 8.69-8.73 (m, 3H), 8.36 (d, 1H), 8.02 (t, 1H), 7.83 (d, 1H), 7.51 (dd, 1H), 7.28 (d, 1H), 6.54 (t, 1H), 6.47 (t, 1H), 5.84 (d, 1H), 5.61 (d, 1H), 2.62-2.66 (m, 2H), 2.43-2.47 (m, 2H), 1.19-1.64 (m, 12H), 0.84-0.90 (m, 6H).

Example 19

Synthesis of Compound (94) of the Present Invention

<Step 1 Synthesis of Compound M>
3 g of 5-bromo-2-chloropyrimidine, 4.63 g of octadecylboronic acid, 35 ml of toluene, 12 ml of water, 7.63 g of K$_3$PO$_4$, 284 mg of Pd$_2$(dba)$_3$, and 50.9 mg of 2-dicyclohexylphosphino-2',6'-dimethoxybiphenyl were placed in a two-neck flask and heated to reflux for 13 hours under an argon atmosphere. The reaction solution was cooled to room temperature and then filtered through a celite layer. Solid obtained by concentrating the filtrate was separated/purified by silica gel chromatography (eluent: a mixed solvent of dichloromethane and hexane) to obtain 1.08 g of an intermediate. 1 g of the intermediate obtained by the operation described above, 47.3 mg of 2,4-difluorophenylboronic acid, 10 mL of 1,2-dimethoxyethane, and 9 ml of a 2 M aqueous solution of potassium carbonate were placed in a two-neck flask. After argon gas was aerated into this solution for 20 minutes, 15.8 mg of a tetrakistriphenylphosphine (0) palladium complex was placed therein. This solution was heated to reflux for 15.5 hours under an argon atmosphere using an oil bath. The organic layer was separated/collected and separated/purified by silica gel chromatography (eluent: a mixed solvent of dichloromethane and hexane) to obtain 251 mg of compound M. The $^1$H-NMR data of the compound M is shown below.

$^1$H-NMR (400 MHz/CDCL$_3$): δ 8.67 (s, 2H), 8.06-8.13 (m, 1H), 6.92-7.01 (m, 2H), 2.64 (t, 2H), 1.26-1.70 (m, 32H), 0.88 (t, 3H).

<Step 2 Synthesis of Compound (M-1)>

90 mg of iridium trichloride n-hydrate, 238 mg of the compound M, 5.4 ml of 2-ethoxyethanol, and 1.8 ml of water were placed in a two-neck flask and heated to reflux for 16 hours under an argon atmosphere. After the reaction solution was cooled to room temperature, water was added thereto, and the resulting solid was filtered to obtain compound (M-1). The isolation yield was 59%. The $^1$H-NMR data of the compound (M-1) is shown below.

$^1$H-NMR (400 MHz/CDCL$_3$): δ 9.03 (s, 4H), 8.80 (s, 4H), 6.42 (t, 4H), 5.26 (d, 4H), 2.48-2.55 (m, 4H), 2.07-2.15 (m, 4H), 1.25-1.60 (m, 128H), 0.87 (t, 12H).

<Step 3 Synthesis of Compound (94) of the Present Invention>

171 mg of the compound (M-1), 93 mg of sodium picolinate, and 18 ml of 2-ethoxyethanol were placed in an eggplant-shaped flask and irradiated with microwave (2450 MHz) for 10 minutes under an argon atmosphere. After the reaction solution was cooled to room temperature, the solvent was concentrated under reduced pressure to obtain solid. This solid was separated/purified by silica gel chromatography (eluent: dichloromethane) to obtain compound (94) of the present invention at an isolation yield of 65%. The $^1$H-NMR data of the compound (94) of the present invention is shown below.

$^1$H-NMR (400 MHz/CDCL$_3$): δ 8.68-8.72 (m, 3H), 8.36 (d, 1H), 8.01 (t, 1H), 7.83 (d, 1H), 7.50 (dd, 1H), 7.28 (d, 1H), 6.54 (dd, 1H), 6.47 (dd, 1H), 5.83 (d, 1H), 5.60 (d, 1H), 2.62-2.66 (m, 2H), 2.40-2.49 (m, 2H), 1.22-1.67 (m, 64H), 0.88 (t, 6H).

Example 20

Synthesis of Compound (95) of the Present Invention 500 mg of iridium trichloride n-hydrate, 1.4 g of 2-(4-heptyloxyphenyl)-5-nonylpyridine (compound N), 20 ml of 2-ethoxyethanol, and 7 ml of water were placed in a two-neck flask and heated to reflux for 14.5 hours under an argon atmosphere. After the reaction solution was cooled to room temperature, water was added thereto, and the resulting solid was filtered and recrystallized from dichloromethane-hexane to obtain compound (N-1). Subsequently, the compound (N-1) obtained by the operation described above, 514 mg of sodium picolinate, and 175 ml of 2-ethoxyethanol were placed in an eggplant-shaped flask and irradiated with microwave (2450 MHz) for 10 minutes under an argon atmosphere. After the reaction solution was cooled to room temperature, the solvent was concentrated under reduced pressure to obtain solid. This solid was recrystallized from dichloromethane-hexane to obtain compound (95) of the present invention. The isolation yield was 67%. The $^1$H-NMR data of the compound (95) of the present invention is shown below.

$^1$H-NMR (400 MHz/CDCL$_3$): δ 8.67 (s, 1H), 8.51 (s, 1H), 8.48 (s, 1H), 8.32 (d, 1H), 7.87-7.93 (m, 3H), 7.85 (d, 1H), 7.38 (t, 1H), 7.23 (s, 1H), 6.57 (d, 1H), 6.50 (d, 1H), 5.90 (s, 1H), 5.73 (s, 1H), 3.68-3.77 (m, 4H), 2.36-2.58 (m, 4H), 1.23-1.64 (m, 48H), 0.88 (m, 12l).

Example 21

Synthesis of Compound (96) of the Present Invention 500 mg of iridium trichloride n-hydrate, 1.19 g of 2-(4-hexyloxyphenyl)-5-octylpyridine (compound O), 20 ml of 2-ethoxyethanol, and 7 ml of water were placed in a two-neck flask and heated to reflux for 17.5 hours under an argon atmosphere. After the reaction solution was cooled to room temperature, water was added thereto, and the resulting solid was filtered and recrystallized from dichloromethane-hexane to obtain compound (O-1). Subsequently, the compound (O-1) obtained by the operation described above, 74 mg of sodium picolinate, and 165 ml of 2-ethoxyethanol were placed in an eggplant-shaped flask and irradiated with microwave (2450 MHz) for 10 minutes under an argon atmosphere. After the reaction solution was cooled to room temperature, the solvent was concentrated under reduced pressure to obtain solid. This solid was recrystallized from dichloromethane-hexane to obtain compound (96) of the present invention. The isolation yield was 64%. The $^1$H-NMR data of the compound (96) of the present invention is shown below.

$^1$H-NMR (400 MHz/CDCL$_3$): δ 8.67 (s, 1H), 8.51 (s, 1H), 8.48 (s, 1H), 8.32 (d, 1H), 7.88-7.93 (m, 3H), 7.85 (d, 1H), 7.39 (t, 1H), 7.23 (s, 1H), 6.57 (d, 1H), 6.50 (d, 1H), 5.90 (s, 1H), 5.73 (s, 1H), 3.68-3.77 (m, 4H), 2.36-2.58 (m, 4H), 1.23-1.64 (m, 40H), 0.88 (m, 12H).

Example 22

Synthesis of Compound (55) of the Present Invention

<Step 1 Synthesis of Compound P>

2.5 g of 5-bromo-2-chloropyrimidine, 1.687 g of 3-chlorophenylboronic acid, 25 mL of 1,2-dimethoxyethane, and 21 ml of a 2 M aqueous solution of potassium carbonate were placed in a two-neck flask. After argon gas was aerated into this solution for 20 minutes, 567 mg of a tetrakistriphenylphosphine (0) palladium complex was placed therein. This solution was heated to reflux for 15.5 hours under an argon atmosphere using an oil bath. The organic layer was separated/collected and separated/purified by silica gel chromatography (eluent: a mixed solvent of dichloromethane and hexane) to obtain 2.13 g of an intermediate. 2.13 g of the intermediate obtained by the operation described above, 3.53 g of (3,5-diphenylphenyl)boronic acid, 34 ml of toluene, 3.16 g of K$_3$PO$_4$, 118 mg of Pd$_2$(dba)$_3$, and 212 mg of 2-dicyclohexylphosphino-2',6'-dimethoxybiphenyl were placed in a two-neck flask and heated to reflux for 17 hours under an argon atmosphere. The reaction solution was cooled to room temperature and then filtered through a celite layer. Solid obtained by concentrating the filtrate was separated/purified by silica gel chromatography (eluent: a mixed solvent of dichloromethane and hexane) to obtain 0.81 g of compound P. The $^1$H-NMR data of the compound P is shown below.

$^1$H-NMR (400 MHz/CDCL$_3$): δ 8.79 (s, 1H), 8.64 (s, 2H), 8.45 (d, 1H), 7.89 (s, 2H), 7.80-7.82 (m, 2H), 7.73 (d, 4H), 7.59 (t, 1H), 7.48 (t, 4H), 7.40 (dd, 2H), 2.62 (t, 2H), 1.26-1.66 (m, 16H), 0.87 (t, 3H).

<Step 2 Synthesis of Compound (P-1)>

55 mg of iridium trichloride n-hydrate, 165 mg of the compound P, 4.5 ml of 2-ethoxyethanol, and 1.2 ml of water were placed in a two-neck flask and heated to reflux for 15 hours under an argon atmosphere. After the reaction solution was cooled to room temperature, water was added thereto, and the resulting solid was filtered to obtain compound (P-1). The isolation yield was 61%.

<Step 3 Synthesis of Compound (55) of the Present Invention>

206 mg of the compound (P-1), 80 mg of acetylacetone, 85.5 mg of sodium carbonate, and 50 ml of 2-ethoxyethanol were reacted at 100° C. for 13.5 hours under an argon atmosphere. After the reaction solution was cooled to room temperature, the solvent was concentrated under reduced pressure to obtain solid. This solid was separated/purified by silica gel chromatography (eluent: a mixed solvent of dichloromethane and hexane) to obtain compound (55) of the present invention at an isolation yield of 35%. The $^1$H-NMR data of the compound (55) of the present invention is shown below.

$^1$H-NMR (400 MHz/CDCL$_3$): δ 8.66 (s, 2H), 8.54 (s, 2H), 8.31 (s, 2H), 7.77 (d, 4H), 7.65-7.69 (m, 10H), 7.44 (t, 8H), 7.35 (t, 4H), 7.20 (d, 2H), 6.48 (d, 2H), 5.27 (s, 1H), 2.72 (t, 4H), 1.26-1.85 (m, 38H), 0.86 (t, 6H).

Next, the luminescence properties of the compound of the present invention will be shown below.

Example 23

Luminescence of Compound (12) of the Present Invention in THF

As a result of dissolving the compound (12) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 497 nm). The emission quantum yield was 0.72.

Example 24

Luminescence of Compound (36) of the Present Invention in THF

As a result of dissolving the compound (36) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 532 nm). The emission quantum yield was 0.67.

Example 25

Luminescence of Compound (39) of the Present Invention in THF

As a result of dissolving the compound (39) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 539 nm). The emission quantum yield was 0.73.

Example 26

Luminescence of Compound (43) of the Present Invention in THF

As a result of dissolving the compound (43) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 535 nm). The emission quantum yield was 0.76.

Example 27

Luminescence of Compound (47) of the Present Invention in THF

As a result of dissolving the compound (47) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 489 nm). The emission quantum yield was 0.53.

Example 28

Luminescence of Compound (53) of the Present Invention in THF

As a result of dissolving the compound (53) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 567 nm). The emission quantum yield was 0.68.

Example 29

Luminescence of Compound (75) of the Present Invention in THF

As a result of dissolving the compound (75) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 470 nm). The emission quantum yield was 0.74.

Example 30

Luminescence of Compound (76) of the Present Invention in THF

As a result of dissolving the compound (76) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 477 nm). The emission quantum yield was 0.81.

Example 31

Luminescence of Compound (82) of the Present Invention in THF

As a result of dissolving the compound (82) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 475 nm). The emission quantum yield was 0.84.

Example 32

Luminescence of Compound (111) of the Present Invention in THF

As a result of dissolving the compound (111) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 461 nm). The emission quantum yield was 0.66.

Example 33

Luminescence of Compound (113) of the Present Invention in THF

As a result of dissolving the compound (113) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 523 nm). The emission quantum yield was 0.71.

Example 34

Luminescence of Compound (41) of the Present Invention in THF

As a result of dissolving the compound (41) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 540 nm). The emission quantum yield was 0.76.

Example 35

Luminescence of Compound (42) of the Present Invention in THF

As a result of dissolving the compound (42) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 540 nm). The emission quantum yield was 0.77.

Example 36

Luminescence of Compound (124) of the Present Invention in THF

As a result of dissolving the compound (124) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 463 nm). The emission quantum yield was 0.88.

Example 37

Luminescence of Compound (91) of the Present Invention in THF

As a result of dissolving the compound (91) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 478 nm). The emission quantum yield was 0.85.

Example 38

Luminescence of Compound (92) of the Present Invention in THF

As a result of dissolving the compound (92) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 478 nm). The emission quantum yield was 0.84.

Example 39

Luminescence of Compound (93) of the Present Invention in THF

As a result of dissolving the compound (93) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 476 nm). The emission quantum yield was 0.84.

Example 40

Luminescence of Compound (94) of the Present Invention in THF

As a result of dissolving the compound (94) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 478 nm). The emission quantum yield was 0.86.

Example 41

Luminescence of Compound (95) of the Present Invention in THF

As a result of dissolving the compound (95) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 496 nm). The emission quantum yield was 0.68.

Example 42

Luminescence of Compound (96) of the Present Invention in THF

As a result of dissolving the compound (96) of the present invention in THF, aerating argon gas thereinto, and then measuring the luminescence spectrum (excitation wavelength: 350 nm) at room temperature using an absolute PL quantum yield measurement apparatus (C9920) manufactured by Hamamatsu Photonics K.K., it exhibited strong luminescence (emission maximum wavelength: 496 nm). The emission quantum yield was 0.65.

Example 43

Solid-State Luminescence of Compound (12) of the Present Invention

As a result of measuring the emission quantum yield (excitation wavelength: 350 nm) of the compound (12) of the present invention in a solid state at room temperature using an absolute PL quantum yield measurement apparatus (C9920) manufactured by Hamamatsu Photonics K.K., the emission quantum yield was 0.14.

Example 44

Solid-State Luminescence of Compound (47) of the Present Invention

As a result of measuring the emission quantum yield (excitation wavelength: 350 nm) of the compound (47) of the present invention in a solid state at room temperature using an absolute PL quantum yield measurement apparatus (C9920) manufactured by Hamamatsu Photonics K.K., the emission quantum yield was 0.12.

Example 45

Solid-State Luminescence of Compound (75) of the Present Invention

As a result of measuring the emission quantum yield (excitation wavelength: 350 nm) of the compound (75) of the present invention in a solid state at room temperature using an absolute PL quantum yield measurement apparatus (C9920) manufactured by Hamamatsu Photonics K.K., the emission quantum yield was 0.22.

Example 46

Solid-State Luminescence of Compound (76) of the Present Invention

As a result of measuring the emission quantum yield (excitation wavelength: 350 nm) of the compound (76) of the present invention in a solid state at room temperature using an absolute PL quantum yield measurement apparatus (C9920) manufactured by Hamamatsu Photonics K.K., the emission quantum yield was 0.18.

Example 47

Solid-State Luminescence of Compound (82) of the Present Invention

As a result of measuring the emission quantum yield (excitation wavelength: 350 nm) of the compound (82) of the present invention in a solid state at room temperature using an absolute PL quantum yield measurement apparatus (C9920) manufactured by Hamamatsu Photonics K.K., the emission quantum yield was 0.34.

Example 48

Solid-State Luminescence of Compound (124) of the Present Invention

As a result of measuring the emission quantum yield (excitation wavelength: 350 nm) of the compound (124) of the present invention in a solid state at room temperature using an absolute PL quantum yield measurement apparatus (C9920) manufactured by Hamamatsu Photonics K.K., the emission quantum yield was 0.51.

Example 49

Solid-State Luminescence of Compound (92) of the Present Invention

As a result of measuring the emission quantum yield (excitation wavelength: 350 nm) of the compound (92) of the present invention in a solid state at room temperature using an absolute PL quantum yield measurement apparatus (C9920) manufactured by Hamamatsu Photonics K.K., the emission quantum yield was 0.28.

Example 50

Solid-State Luminescence of Compound (1) of the Present Invention

As a result of measuring the emission quantum yield (excitation wavelength: 350 nm) of the compound (1) of the present invention in a solid state at room temperature using an absolute PL quantum yield measurement apparatus (C9920) manufactured by Hamamatsu Photonics K.K., the emission quantum yield was 0.04.

Next, TG measurement results of the compound of the present invention will be shown below.

Example 51

Thermal Stability of Compound (2) of the Present Invention

The decomposition temperature of the compound (2) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 381° C., and the temperature of 50% decrease in weight was 450° C. or higher. It was demonstrated that the compound (2) of the present invention exhibited very favorable heat resistance.

Example 52

Thermal Stability of Compound (12) of the Present Invention

The decomposition temperature of the compound (12) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 400° C., and the temperature of 50% decrease in weight was 450° C. or higher. It was demonstrated that the compound (12) of the present invention exhibited very favorable heat resistance.

Example 53

Thermal Stability of Compound (39) of the Present Invention

The decomposition temperature of the compound (39) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 324° C., and the temperature of 50% decrease in weight was 390° C. It was demonstrated that the compound (39) of the present invention exhibited very favorable heat resistance.

Example 54

Thermal Stability of Compound (41) of the Present Invention

The decomposition temperature of the compound (41) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 315° C., and the temperature of 50% decrease in weight was 450° C. or higher. It was demonstrated that the compound (41) of the present invention exhibited very favorable heat resistance.

Example 55

Thermal Stability of Compound (42) of the Present Invention

The decomposition temperature of the compound (42) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 322° C., and the temperature of 50% decrease in weight was 450° C. or higher. It was demonstrated that the compound (42) of the present invention exhibited very favorable heat resistance.

Example 56

Thermal Stability of Compound (43) of the Present Invention

The decomposition temperature of the compound (43) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 324° C., and the temperature of 50% decrease in weight was 450° C. or higher. It was demonstrated that the compound (43) of the present invention exhibited very favorable heat resistance.

Example 57

Thermal Stability of Compound (47) of the Present Invention

The decomposition temperature of the compound (47) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 347° C., and the temperature of 50% decrease in weight was 450° C. or higher. It was demonstrated that the compound (47) of the present invention exhibited very favorable heat resistance.

Example 58

Thermal Stability of Compound (53) of the Present Invention

The decomposition temperature of the compound (53) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 348° C., and the temperature of 50% decrease in weight was 450° C. or higher. It was demonstrated that the compound (53) of the present invention exhibited very favorable heat resistance.

Example 59

Thermal Stability of Compound (75) of the Present Invention

The decomposition temperature of the compound (75) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 364° C., and the temperature of 50% decrease in weight was 450° C. or higher. It was demonstrated that the compound (75) of the present invention exhibited very favorable heat resistance.

Example 60

Thermal Stability of Compound (76) of the Present Invention

The decomposition temperature of the compound (76) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 361° C., and the temperature of 50% decrease in weight was 450° C. or higher. It was demonstrated that the compound (76) of the present invention exhibited very favorable heat resistance.

Example 61

Thermal Stability of Compound (82) of the Present Invention

The decomposition temperature of the compound (82) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 360° C., and the temperature of 50% decrease in weight was 450° C. or higher. It was demonstrated that the compound (82) of the present invention exhibited very favorable heat resistance.

Example 62

Thermal Stability of Compound (92) of the Present Invention

The decomposition temperature of the compound (92) of the present invention was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 358° C., and the temperature of 50% decrease in weight was 450° C. or higher. It was demonstrated that the compound (92) of the present invention exhibited very favorable heat resistance.

Meanwhile, there is description as 376° C. about the temperature of 50% decrease in weight of the above-mentioned iridium complex (formula (A)) in Non Patent Literature 1, demonstrating that the compound of the present invention exhibits higher thermal stability.

Comparative Example 1

As a result of synthesizing an iridium complex represented by formula (D) described in Non Patent Literature 3 above as a comparative compound and measuring the emission quantum yield (excitation wavelength: 350 nm) in a solid state at room temperature using an absolute PL quantum yield measurement apparatus (C9920) manufactured by Hamamatsu Photonics K.K., the emission quantum yield was 0.16. Moreover, the decomposition temperature of the iridium complex represented by the following formula (D) was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 344° C.

[Chemical Formula 14]

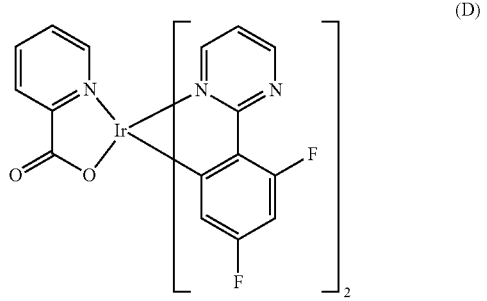

(D)

Comparative Example 2

As a result of synthesizing an iridium complex represented by formula (E) as a comparative compound and measuring the emission quantum yield (excitation wavelength: 350 nm) in a solid state at room temperature using an absolute PL quantum yield measurement apparatus (C9920) manufactured by Hamamatsu Photonics K.K., the emission quantum yield was 0.13. Moreover, the decomposition temperature of the iridium complex represented by the following formula (E) was measured with a TG/DTA simultaneous measurement apparatus (DTG-60 manufactured by Shimadzu Corp.). As a result of setting the rate of temperature increase to 15° C./min and increasing the temperature at normal pressure under a nitrogen gas atmosphere, 5% decrease in weight was seen at 357° C.

[Chemical Formula 15]

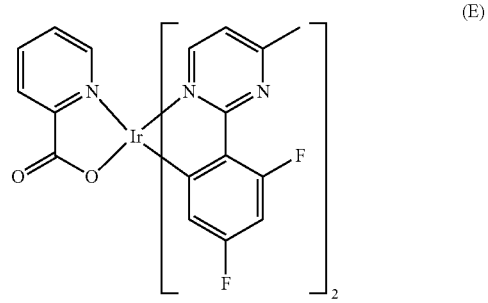

(E)

Comparative Example 3

As a result of synthesizing an iridium complex represented by formula (C) described in Non Patent Literature 7 above as a comparative compound and measuring the emission quantum yield (excitation wavelength: 350 nm) in a solid state at room temperature using an absolute PL quantum yield measurement apparatus (C9920) manufactured by Hamamatsu Photonics K.K., the emission quantum yield was 0.01, which was a very low value.

[Chemical Formula 7]

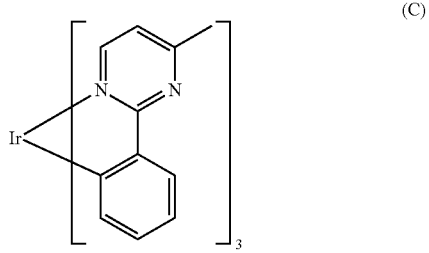

(C)

Comparative Example 4

As a result of synthesizing an iridium complex represented by formula (F) as a comparative compound and measuring the emission quantum yield (excitation wavelength: 350 nm) in a solid state at room temperature using an absolute PL quantum yield measurement apparatus (C9920) manufactured by Hamamatsu Photonics K.K., the emission quantum yield was 0.03. Moreover, for confirming solubility in solvents (chloroform and toluene), a 0.1 wt % solution was prepared and confirmed by visual observation to have considerable amounts of residues.

[Chemical Formula 16]

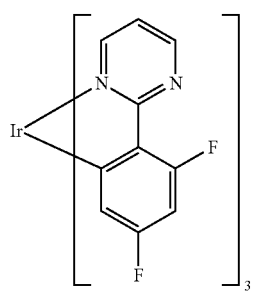
(F)

The analysis results of the compound (76) of the present invention, the compound (82) of the present invention, the compound (92) of the present invention, the comparative compound (formula (D)), and the comparative compound (formula (E)) are summarized in Table 13. From Table 13, it was shown that, by introducing an alkyl group having 2 or more carbon atoms in $R^a$, the thermal stability, i.e., heat resistance, of the iridium complex was largely improved compared with the comparative compound (formula (D)) in which $R^a$ was unsubstituted. Moreover, it was revealed that the emission quantum yield (solid state) was also largely improved by introducing an alkyl group having 2 or more carbon atoms in $R^a$. On the other hand, in regard to the comparative compound (formula (E)), it was revealed that thermal stability was improved compared with the comparative compound (formula (D)) whereas the emission quantum yield (solid) was rather reduced.

TABLE 13

|  | Comparative compound (formula (D)) | Comparative compound (formula (E)) | Compound of the present invention (76) |
|---|---|---|---|
| Temperature of 5% decrease in weight | 344° C. | 357° C. | 361° C. |
| Emission quantum yield (solid) | 0.16 | 0.13 | 0.18 |

|  | Compound of the present invention (92) | Compound of the present invention (82) |
|---|---|---|
| Temperature of 5% decrease in weight | 358° C. | 360° C. |
| Emission quantum yield (solid) | 0.28 | 0.34 |

Moreover, the analysis results of the compound (1) of the present invention and the comparative compound (formula (C)) are summarized in Table 14. Comparing the emission quantum yields (solid state) of these compounds, they were 0.04 and 0.01, respectively, demonstrating that the compound (1) of the present invention had 4 times higher the emission quantum yield of the comparative compound. Specifically, it was revealed that the emission quantum yield (solid state) of the iridium complex largely depended on the position of substitution of an alkyl group and the introduction of an alkyl group having 2 or more carbon atoms in $R^a$ very effectively worked on the improvement in the solid-state emission quantum yield.

TABLE 14

| | Comparative compound (formula (C)) | Compound of the present invention (1) |
|---|---|---|
| Emission quantum yield (solid) | 0.01 | 0.04 |

Furthermore, the analysis results of the compound (12) of the present invention and the comparative compound (formula (F)) are summarized in Table 15. From Table 15, it was shown that the compound (12) of the present invention in which an n-decyl group was introduced in $R^a$ was more excellent in solubility in solvents. Moreover, it was revealed that the compound (12) of the present invention had approximately 4.5 times higher the emission quantum yield (solid state) of the comparative compound.

TABLE 15

| | Comparative compound (formula (F)) Facial form | Compound of the present invention (12) Facial form |
|---|---|---|
| Solubility in toluene (0.1 wt %) | Residues remained | Completely dissolved |
| Solubility in chloroform (0.1 wt %) | Residues remained | Completely dissolved |
| Emission quantum yield (solid) | 0.03 | 0.14 |

From Examples above, it was revealed that the compound of the present invention represented by formula (1) or (2) was very thermally stable and exhibited a high emission quantum yield in a solution or in a solid state compared with iridium complexes in which a substituent was not introduced in $R^a$. Furthermore, it was revealed that the emission wavelength could be adjusted by introducing various substituents in the iridium complex of the present invention and by changing the ligand L. Thus, the iridium complex of the present invention can be applied to organic electroluminescent element materials, electrochemiluminescence (ECL) element materials, luminescent sensors, photosensitizers, displays, materials for photographs, laser dyes, dyes for color filters, optical communications, color conversion filters, backlights, illumination, photosensitizing dyes, luminescent probes for cell imaging, various light sources, etc.

The invention claimed is:
1. An iridium complex represented by the following formula (2):

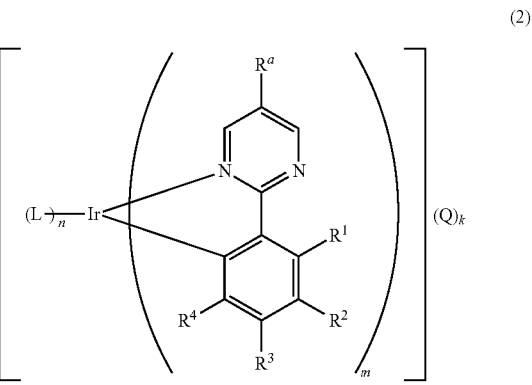

(2)

wherein N represents a nitrogen atom; m represents an integer of 1 to 3;
n represents an integer of 0 to 2; m+n=3;
$R^a$ represents an alkyl group having 2 to 30 carbon atoms which may have a substituent selected from a group consisting of an alkyl group, an aralkyl group, an alkoxyl group, an aryl group, a heterocyclic group, an aryloxyl group, an amino group, a cyano group, a hydroxyl group, a chloro atom, a bromo atom, an iodo atom and a nitro group;

$R^1$ to $R^4$ each independently represent:

a hydrogen atom or an alkyl group having 1 to 30 carbon atoms which may have a substituent selected from a group consisting of an alkyl group, an aralkyl group, an alkoxyl group, an aryl group, a heterocyclic group, an aryloxyl group, an amino group, a cyano group, a hydroxyl group, a chloro atom, a bromo atom, an iodo atom and a nitro group, an aryl group having 6 to 60 carbon atoms which may have a substituent selected from a group consisting of an alkyl group, an aralkyl group, an alkoxyl group, an aryl group, a heterocyclic group, an aryloxyl group, an amino group and a cyano group, an alkenyl group having 2 to 30 carbon atoms which may have a substituent selected from a group consisting of an alkyl group, an aralkyl group, an alkoxyl group, an aryl group, a heterocyclic group, an aryloxyl group, an amino group and a cyano group, an alkynyl group having 2 to 30 carbon atoms which may have a substituent selected from a group consisting of an alkyl group, an aralkyl group, an alkoxyl group, an aryl group, a heterocyclic group, an aryloxyl group, an amino group and a cyano group, an amino group having 0 to 30 carbon atoms which may have a substituent selected from a group consisting of an alkyl group, an aralkyl group, an alkoxyl group, an aryl group, a heterocyclic group, an aryloxyl group, an amino group and a cyano group, a heterocyclic group having 1 to 60 carbon atoms, with a hetero atom selected from a group consisting of N, O, S, Si and Ge atoms, which may have a substituent selected from a group consisting of an alkyl group, an aralkyl group, an alkoxyl group, an aryl group, a heterocyclic group, an aryloxyl group, an amino group and a cyano group, an alkoxy group having 1 to 30 carbon atoms which may have a substituent selected from a group consisting of an alkyl group, an aralkyl group, an alkoxyl group, an aryl group, a heterocyclic group, an aryloxyl group, an amino group and a cyano group, an alkylthio group having 1 to 30 carbon atoms which may have a substituent selected from a group consisting of an alkyl group, an aralkyl group, an alkoxyl group, an aryl group, a heterocyclic group, an aryloxyl group, an amino group and a cyano group, an aryloxy group having 6 to 60 carbon atoms which may have a substituent selected from a group consisting of an alkyl group, an aralkyl group, an alkoxyl group, an aryl group, a heterocyclic group, an aryloxyl group, an amino group and a cyano group, an arylthio group having 6 to 60 carbon atoms which may have a substituent selected from a group consisting of an alkyl group, an aralkyl group, an alkoxyl group, an aryl group, a heterocyclic group, an aryloxyl group, an amino group and a cyano group, a heterocyclic oxy group having 1 to 60 carbon atoms which may have a substituent selected from a group consisting of an alkyl group, an aralkyl group, an alkoxyl group, an aryl group, a heterocyclic group, an aryloxyl group, an amino group and a cyano group, a heterocyclic thio group having 1 to 60 carbon atoms which may have a substituent_selected from a group consisting of an alkyl group, an aralkyl group, an alkoxyl group, an aryl group, a heterocyclic group, an aryloxyl group, an amino group and a cyano group, an acyl group selected from a group consisting of an acetyl group, a propiony group, a butyryl group, an isobutyryl group, a pivaloyl group, a benzoyl group, a trifluoroacetyl group, and a pentafluorobenzoyl group, an acyloxy group selected from a group consisting of an acetoxy group, a propionyloxy group, a butyryloxy group, an isobutyryloxy group, a pivaloyloxy group, a benzoyloxy group, a trifluoroacetyloxy group and a pentaflurobenzoyloxy group, a substituted silyl group, a substituted silyloxy group, a substituted silylthio group, a substituted silylamino group, a halogen atom, a cyano group, a carboxyl group, or a trifluoromethyl group;

Q represents a counter ion;

k represents an integer of 0 to 2;

L represents a bidentate ligand selected from a group consisting of a bidentate ligand forming a Ir-nitrogen bond and a Ir-carbon bond, a bidentate ligand forming a Ir-nitrogen bond and Ir-oxygen bond, a bidentate ligand forming two Ir-oxygen bonds, and a bidentate ligand forming two Ir-nitrogen bonds; and adjacent substituents may be bonded to form a ring structure.

2. The iridium complex according to claim 1, wherein L is represented by any of formulas (3) to (11):

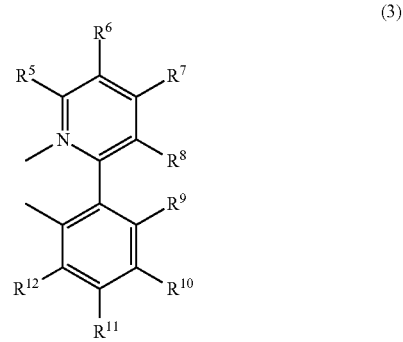

(3)

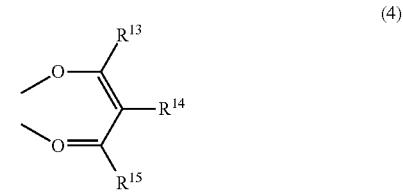

(4)

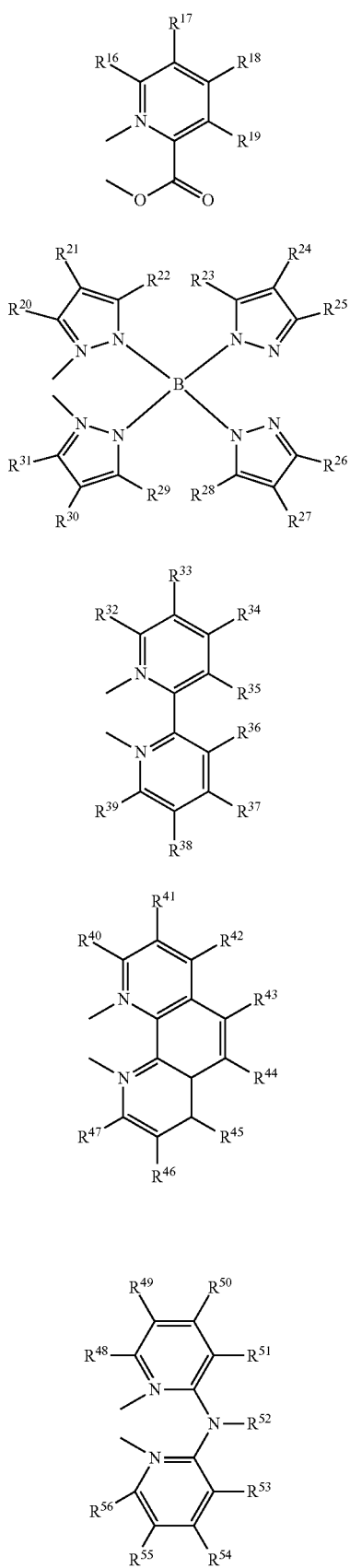

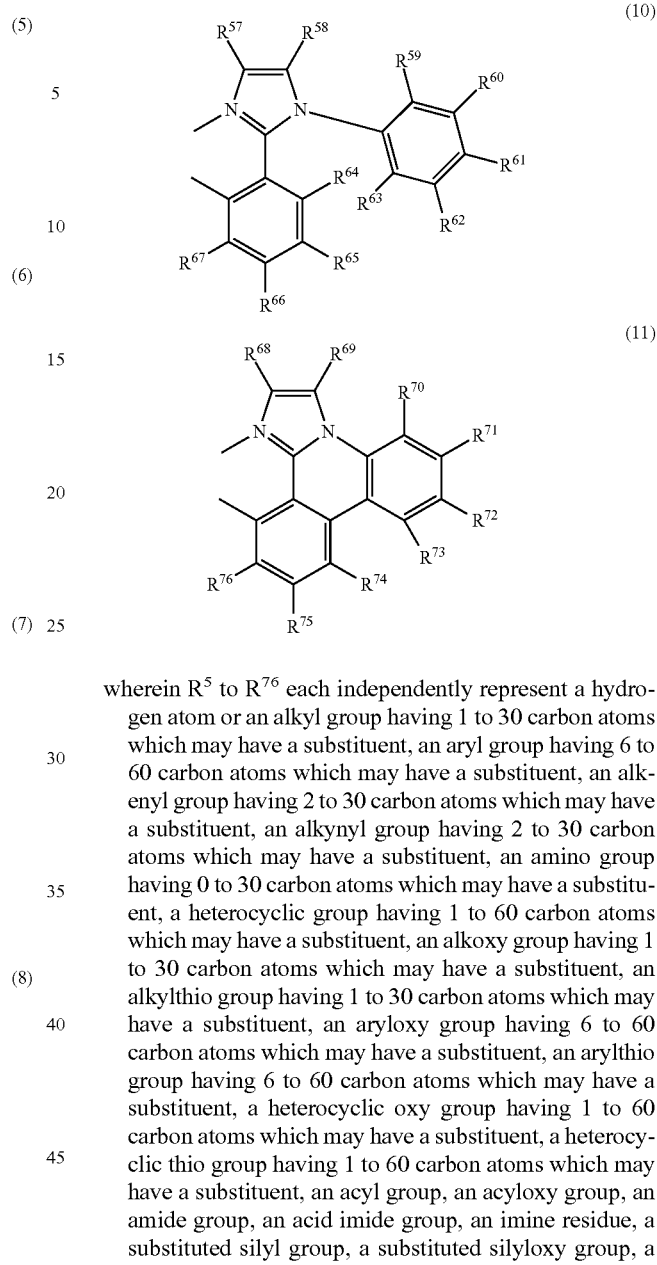

wherein $R^5$ to $R^{76}$ each independently represent a hydrogen atom or an alkyl group having 1 to 30 carbon atoms which may have a substituent, an aryl group having 6 to 60 carbon atoms which may have a substituent, an alkenyl group having 2 to 30 carbon atoms which may have a substituent, an alkynyl group having 2 to 30 carbon atoms which may have a substituent, an amino group having 0 to 30 carbon atoms which may have a substituent, a heterocyclic group having 1 to 60 carbon atoms which may have a substituent, an alkoxy group having 1 to 30 carbon atoms which may have a substituent, an alkylthio group having 1 to 30 carbon atoms which may have a substituent, an aryloxy group having 6 to 60 carbon atoms which may have a substituent, an arylthio group having 6 to 60 carbon atoms which may have a substituent, a heterocyclic oxy group having 1 to 60 carbon atoms which may have a substituent, a heterocyclic thio group having 1 to 60 carbon atoms which may have a substituent, an acyl group, an acyloxy group, an amide group, an acid imide group, an imine residue, a substituted silyl group, a substituted silyloxy group, a substituted silylthio group, a substituted silylamino group, a halogen atom, a cyano group, a carboxyl group, or a trifluoromethyl group; and adjacent substituents may be bonded to form a ring structure.

3. The iridium complex according to claim 1, wherein $R^1$ is a hydrogen atom or a fluorine atom.

4. The iridium complex according to claim 1, wherein $R^2$ is a hydrogen atom, an alkyl group having 1 to 30 carbon atoms which may have a substituent, or an aryl group having 6 to 60 carbon atoms which may have a substituent.

5. The iridium complex according to claim 1, wherein $R^2$ is a trifluoromethyl group.

6. The iridium complex according to claim 1, wherein $R^3$ is a hydrogen atom, an alkyl group having 1 to 30 carbon atoms which may have a substituent, or an aryl group having 6 to 60 carbon atoms which may have a substituent.

7. The iridium complex according to claim 1, wherein $R^3$ is a fluorine atom.

8. The iridium complex according to claim 1, wherein any of $R^1$ to $R^4$ is a dendron.

9. The iridium complex according to claim 1, wherein $R^a$ is an alkyl group having 2 to 30 carbon atoms.

10. The iridium complex according to claim 1, wherein $R^a$ is an n-decyl group.

11. The iridium complex according to claim 1, wherein m=3 and n=0.

12. The iridium complex according to claim 1, wherein m=2 and n=1.

13. The iridium complex according to claim 1, wherein m=1 and n=2.

14. The iridium complex according to claim 1, wherein any of $R^1$ to $R^4$ is a dendron selected from a group consisting of Chemical Formula [09], Chemical Formula [10] and Chemical Formula [11]:

[Chemical Formula 09]

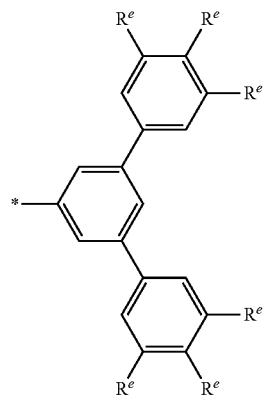

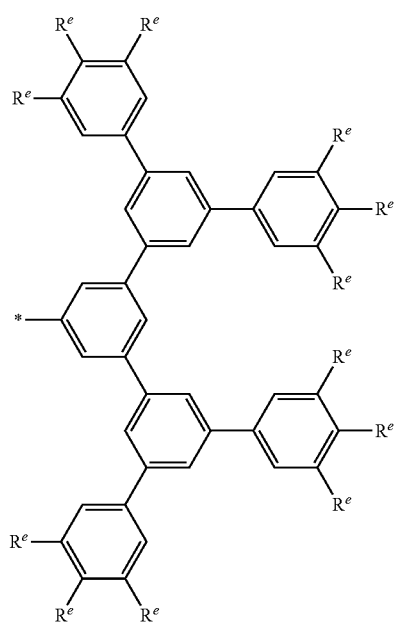

[Chemical Formula 10]

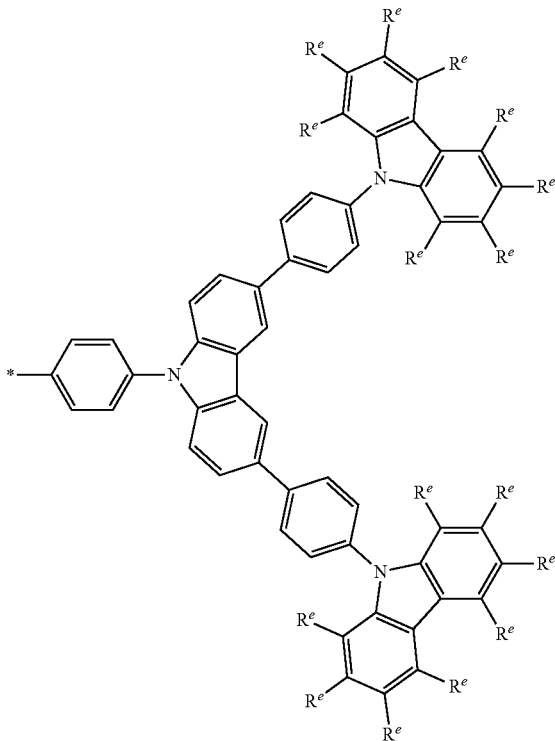

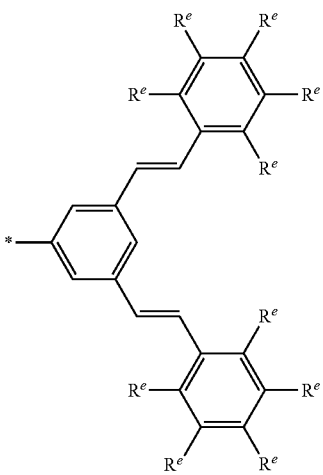

119
-continued
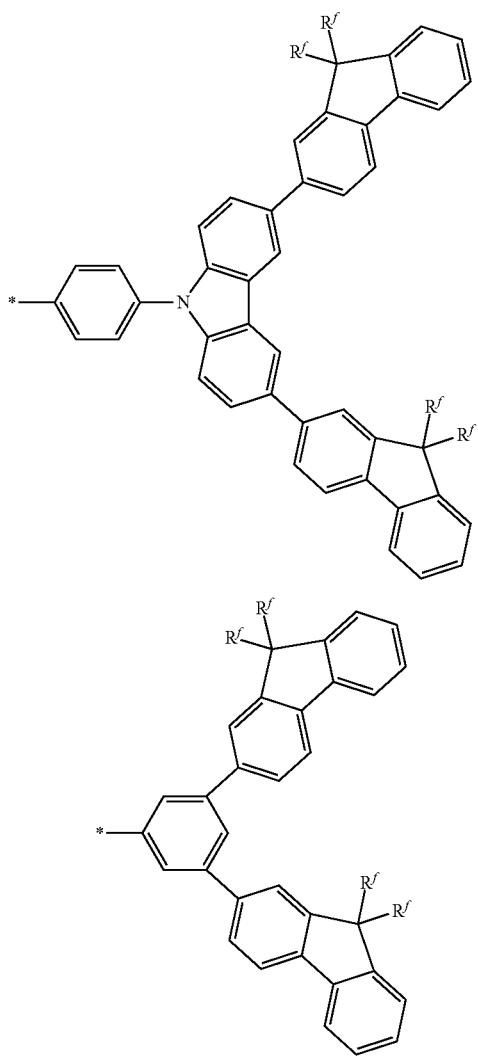
120
-continued
[Chemical Formula 11]
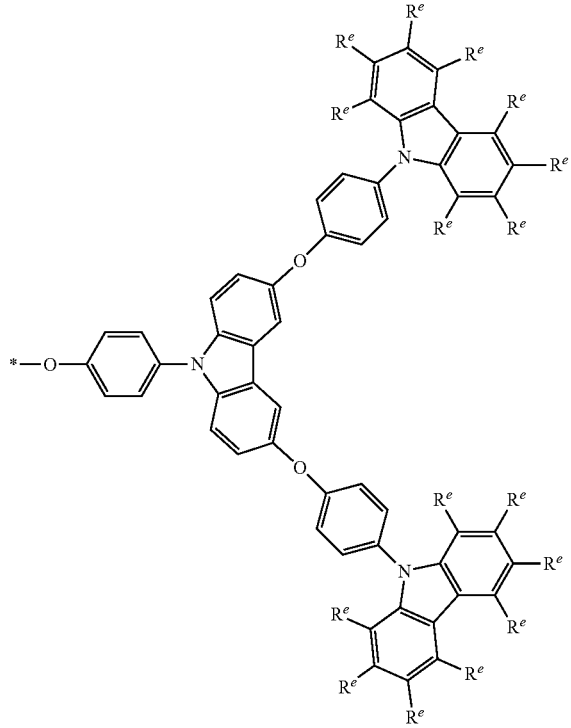
wherein $R^e$ is selected from a group consisting of a hydrogen atom, an alkyl group comprising 1-10 carbon atoms or an alkoxy group comprising 1 to 10 carbon atoms, $R^f$ represents an alkyl group having 1 to 10 carbon atoms, and * represents a binding site for any of $R^1$ to $R^{76}$.
* * * * *